(12) United States Patent
Berg et al.

(10) Patent No.: US 6,410,530 B1
(45) Date of Patent: Jun. 25, 2002

(54) SUBSTITUTED 1,2,3,4-TETRAHYDRONAPHTHALENE DERIVATIVES

(75) Inventors: Stefan Berg, Ekerö; Lennart Florvall; Svante Ross, both of Södertälje; Seth-Olov Thorberg, Strängnäs, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/653,427

(22) Filed: Aug. 31, 2000

Related U.S. Application Data

(62) Division of application No. 08/836,004, filed as application No. PCT/SE97/00469 on Mar. 20, 1997, now Pat. No. 6,124,283.

(30) Foreign Application Priority Data

Mar. 22, 1996 (SE) ................................. 9601110

(51) Int. Cl.[7] ............................................. A61K 31/535
(52) U.S. Cl. ..................... 514/235.5; 544/392; 544/395; 514/255.03; 514/319; 546/206
(58) Field of Search ................................. 544/392, 395; 544/130; 514/255.03, 319, 235.5; 546/206

(56) References Cited

U.S. PATENT DOCUMENTS 5,426,226 A * 6/1995 Hoechstetter et al. ........ 564/342

FOREIGN PATENT DOCUMENTS

| EP | 0402923 | 12/1990 |
|---|---|---|
| EP | 0533266 | 3/1993 |
| EP | 0533267 | 3/1993 |
| EP | 0533268 | 3/1993 |
| GB | 2273930 | 7/1994 |
| WO | 9413659 | 6/1994 |
| WO | 9421619 | 9/1994 |
| WO | 9426703 | 11/1994 |
| WO | 9511243 | 4/1995 |
| WO | 9905134 | 3/1999 |
| WO | 9913876 | 3/1999 |
| WO | 9913877 | 3/1999 |
| WO | 9913878 | 3/1999 |

OTHER PUBLICATIONS

Saxena, Serotonin Receptors: Subtypes, Functional Response and Therapeutic Relevvance, Jan. 1995.*

* cited by examiner

Primary Examiner—Richard L. Raymond
Assistant Examiner—Hong Liu
(74) Attorney, Agent, or Firm—White & Case LLP

(57) ABSTRACT

New piperidinyl- or piperazinyl-substituted-1,2,3,4-tetrahydronaphthalene derivatives having the formula

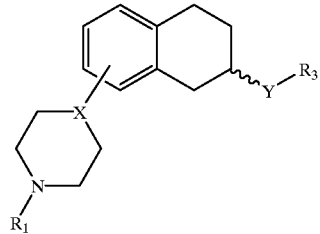

(I)

wherein
X is N or CH;
Y is $NR_2CH_2$, $CH_2—NR_2$, $NR_2—CO$, $CO—NR_2$ or $NR_2SO_2$;
$R_1$ is H, $C_1–C_6$ alkyl or $C_3–C_6$ cycloalkyl;
$R_3$ is $C_1–C_6$ alkyl, $C_3–C_6$ cycloalkyl or $(CH_2)_n$-aryl, where aryl is phenyl or a heteroaromatic ring containing one or two heteroatoms selected from N, O and S and which may be mono- or di-substituted;
n is 0–4;
as (R)-enantiomer, (S)-enantiomer or a racemate in the form of the free base or a pharmaceutically acceptable salt or hydrate thereof; a pharmaceutical formulation containing the compounds, use of the compounds in the treatment of 5-hydroxytryptamine mediated disorders, processes for the preparation of the compounds and intermediates for the preparation of the compounds.

30 Claims, 1 Drawing Sheet

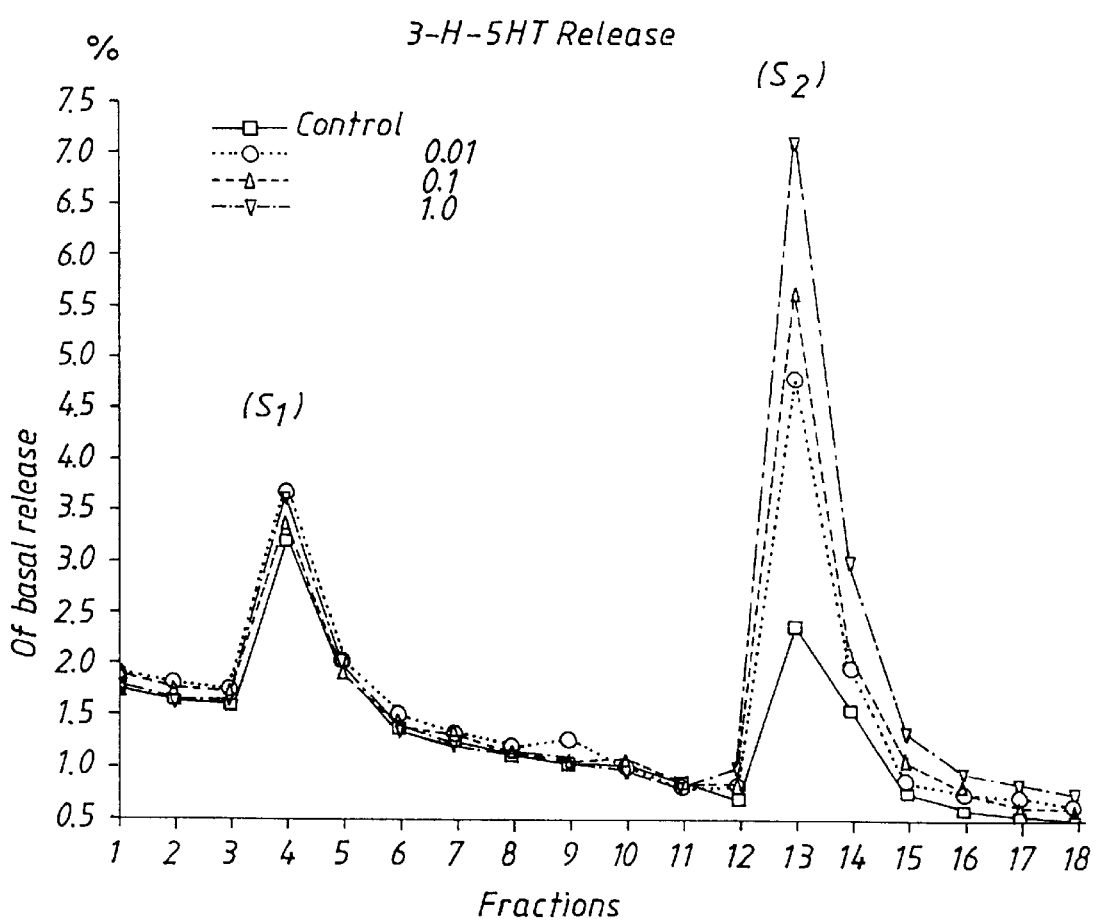

SUBSTITUTED 1,2,3, 4-TETRAHYDRONAPHTHALENE DERIVATIVES

This application is a divisional of application Ser. No. 08/836,004, filed Apr. 25, 1997, U.S. Pat. No. 6,124,283 which was the National Stage of International Application No. PCT/SE97/00469, filed Mar. 20, 1997.

FIELD OF THE INVENTION

The present invention relates to the new compounds, piperidinyl- or piperazinyl-substituted-1,2,3,4-tetrahydronaphthalene derivatives as (R)-enantiomers, (S)-enantiomers or racemates in the form of a free base or pharmaceutically acceptable salts thereof, a process for their preparation, pharmaceutical compositions containing said therapeutically active compounds and to the use of said active compounds in therapy.

An object of the invention is to provide compounds for therapeutic use, especially compounds having a selective effect at a subgroup of 5-hydroxy-tryptamine receptors, designated the $5\text{-}HT_{1D}$-receptor in mammals including man.

It is also an object of the invention to provide compounds with a therapeutic effect after oral administration.

PRIOR ART

Different classes of piperazinyl substituted benzanilide derivatives as $5\text{-}HT_{1D}$ antagonists are disclosed in inter alia EP 533266, EP 533267, EP 533268, GB 2273930 and WO 95/11243.

WO 94/13659 discloses an extremely broad class of fused benzo compounds having a para substituted piperidinyl or piperazinyl radical in the aromatic ring. Said class of compounds is stated to bind to the $5\text{-}HT_{1A}$ receptor.

WO 94/21619 discloses a fully aromatic naphthalene ring system which may be substituted with a piperidinyl or piperazinyl group, said compounds are also stated to be potent serotonin ($5HT_1$) agonists and antagonists.

EP 402923 discloses 2-aminoalkyl or alkylenaromatic substituted 1,2,3,4-tetrahydronaphthalene derivatives having a further nitrogen substitution in the 5 position in the tetraline ring. Said compounds act as dopamine agonists.

BACKGROUND OF THE INVENTION

Various central nervous system disorders such as depression, anxiety, etc. appear to involve the disturbance of the neurotransmitters noradrenaline (NA) and 5-hydroxytryptamine (5-HT), the latter also known as serotonin. The drugs most frequently used in the treatment of depression are believed to act by improving the neurotransmission of either or both of these physiological agonists. It appears that the enhancement of 5-HT neurotransmission primarily affects the depressed mood and anxiety, whereas the enhancement of noradrenaline neurotransmission affects the retardation symptoms occurring in depressed patients. The invention concerns compounds which have an effect on 5-HT neurotransmission.

Serotonin, or 5-HT, activity is thought to be involved in many different types of psychiatric disorders. For instance it is thought that an increase in 5-HT activity is associated with anxiety, while a decrease in 5-HT release has been associated with depression. Serotonin has in addition been implicated in such diverse conditions as eating disorders, gastrointestinal disorders, cardiovascular regulation and sexual behavior.

The 5-HT Receptors

The various effects of 5-HT may be related to the fact that serotoninergic neurons stimulate the secretion of several hormones, e.g. cortisol, prolactin, β-endorphin, vasopressin and others. The secretion of each of these other hormones appears to be regulated on a specific basis by several different 5-HT (serotonin) receptor subtypes. With the aid of molecular biology techniques, to date these receptors have been classified as $5\text{-}HT_1$, $5\text{-}HT_2$, $5\text{-}HT_3$, $5\text{-}HT_4$, $5\text{-}ht_5$, $5\text{-}ht_6$ and $5\text{-}ht_7$ with the $5\text{-}HT_1$ receptor further divided into the $5\text{-}HT_{1A}$, $5\text{-}HT_{1B}$, $5\text{-}HT_{1D}$, $5\text{-}HT_{1E}$ and $5\text{-}HT_{1F}$ subtypes. Each receptor subtype is involved in a different serotonin function and has different properties.

Regulation of the 5-HT Transmission

The release of 5-HT at the nerve terminals is feedback-regulated by two different subtypes of 5-HT receptors. Inhibitory $5\text{-}HT_{1A}$ autoreceptors are located on the cell bodies in the raphé nuclei which upon stimulation by 5-HT decrease the impulse propagation in the 5-HT neurons and thereby reduce the 5-HT release at the nerve terminals. Another subtype of inhibitory 5-HT receptors is located on the 5-HT nerve terminals, the $5\text{-}HT_{1D}$ receptors (in rodents the $5\text{-}HT_{1B}$ receptors) which regulate the synaptic concentration of 5-HT by controlling the amount of 5-HT that is released. An antagonist of these terminal autoreceptors thus increases the amount of 5-HT released by nerve impulses, as has been shown in both in vitro and in vivo experiments.

The use of an antagonist of the terminal $5\text{-}HT_{1D}$ autoreceptor will accordingly increase the synaptic 5-HT concentration and enhance the transmission in the 5-HT system. The antagonist would thus produce an antidepressant effect making it useful as a medication for depression.

Other localizations of $5\text{-}HT_{1D}$ receptor subtype also exist. A large part of these receptors appear to be located on nerve terminals of other neuronal systems (so called heteroreceptors). Since the $5\text{-}HT_{1D}$ receptor mediates inhibitory responses, an antagonist of this receptor subtype might also increase the release of other neurotransmitters than 5-HT.

Compounds having $5\text{-}HT_{1D}$ activity may according to well known and recognized pharmacological tests be divided into full agonists, partial agonists and antagonists.

DISCLOSURE OF THE INVENTION

The primary object of the present invention is to provide compounds having a selective effect at the $5\text{-}HT_{1D}$ receptor, preferably antagonistic properties, as well as having a good bioavailability. The effect on the other receptors chosen from, for example, the $5\text{-}HT_{1A}$, $5\text{-}HT_{2A}$, $D_1$, $D_{2A}$, $D_3$, $\alpha_1$ and $\alpha_2$ receptor has been investigated.

Accordingly, the present invention provides compounds of the formula I

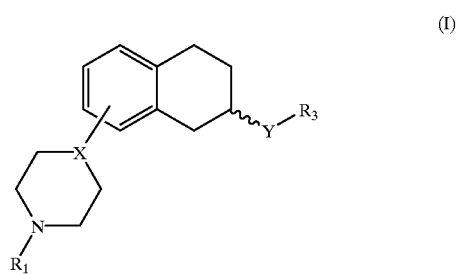

(I)

wherein

X is N or CH;

Y is $NR_2CH_2$, $CH_2-NR_2$, $NR_2-CO$, $CO-NR_2$ or $NR_2SO_2$;

$R_1$ is H, $C_1-C_6$ alkyl or $C_3-C_6$ cycloalkyl;

$R_2$ is H or $C_1-C_6$ alkyl;

$R_3$ is $C_1-C_6$ alkyl, $C_3-C_6$ cycloalkyl or $(CH_2)_n$-aryl, where aryl is phenyl or a heteroaromatic ring containing one or two heteroatoms selected from N, O and S and which may be mono- or di-substituted with $R_4$ and/or $R_5$;

$R_4$ is H, $C_1-C_6$ alkyl, $C_3-C_6$ cycloalkyl, halogen, CN, $CF_3$, OH, $C_1-C_6$ alkoxy, $NR_6R_7$, $OCF_3$, $SO_3CH_3$, $SO_3CF_3$, $SO_2NR_6R_7$, phenyl, phenyl-$C_1-C_6$ alkyl, phenoxy, $C_1-C_6$ alkyl, phenyl, $C_1-C_6$ alkyl-heterocyclic ring containing one or two heteroatoms or substituted heteroatoms selected from N, O, S, SO and $SO_2$, an optionally substituted heterocyclic or heteroaromatic ring containing one or two heteroatoms or substituted heteroatoms selected from N, O, S, SO and $SO_2$, wherein the optional substituent(s) is(are) selected from $C_1-C_6$ alkyl, $C_3-C_6$ cycloalkyl and phenyl-$C_1-C_6$ alkyl; or $COR_8$;

$R_5$ is H, OH, $CF_3$, $OCF_3$, halogen, $C_1-C_6$ alkyl or $C_1-C_6$ alkoxy, $R_6$ is H, $C_1-C_6$ alkyl or $C_3-C_6$ cycloalkyl;

$R_7$ is H, $C_1-C_6$ alkyl or $C_3-C_6$ cycloalkyl;

$R_8$ is $C_1-C_6$ alkyl, $C_3-C_6$ cycloalkyl, $CF_3$, $NR_6R_7$, phenyl, or a heterocyclic ring containing one or two heteroatoms or substituted heteroatoms selected from N, O, S, SO and $SO_2$;

n is 0–4;

as (R)-enantiomer, (S)-enantiomer or a racemate in the form of the free base or a pharmaceutically acceptable salt or hydrate thereof which possesses a high selective effect at the 5-$HT_{1D}$ receptor and also shows sufficient bioavailability after oral administration.

In the present context $C_1-C_6$ alkyl may be straight or branched. $C_1-C_6$ alkyl may be methyl, ethyl, n-propyl, i-propyl, n-butyl, i-butyl, s-butyl, t-butyl, n-pentyl, i-pentyl, t-pentyl, neo-pentyl, n-hexyl or i-hexyl.

In the present context $C_1-C_6$ alkoxy may be straight or branched. $C_1-C_6$ alkoxy may be methoxy, ethoxy, n-propoxy, i-propoxy, n-butoxy, i-butoxy, s-butoxy, t-butoxy, n-pentyloxy, i-pentyloxy, t-pentyloxy, neo-pentyloxy, n-hexyloxy or i-hexyloxy.

In the present context $C_3-C_6$ cycloalkyl may be cyclopropyl, cyclobutyl, cyclopentyl or cyclohexyl, preferably cyclohexyl.

In the present context halogen may be fluoro, chloro, bromo or iodo.

In the present context the heteroaromatic ring containing one or two heteroatoms selected from N, O and S preferably is a 5- or 6-membered heteroaromatic ring and may be furyl, imidazolyl, isoxazolyl, isothiazolyl, oxazolyl, pyrazinyl, pyrazolyl, pyridazinyl, pyridyl, pyrimidyl, pyrrolyl, thiazolyl or thienyl. The heteroaromatic ring can be either substituted or unsubstituted.

In the present context the heterocyclic ring containing one or two heteroatoms or substituted heteroatoms selected from N, O, S, SO and $SO_2$ may optionally contain a carbonyl function and is preferably a 5-, 6- or 7-membered heterocyclic ring and may be imidazolidinyl, imidazolinyl, morpholinyl, piperazinyl, piperidinyl, piperidonyl, pyrazolidinyl, pyrazolinyl, pyrrolidinyl, pyrrolinyl, tetrahydropyranyl, thiomorpholinyl, preferably piperidino, 1-piperazinyl, morpholino, thiomorpholino and 4-piperidon-1-yl.

A preferred embodiment of the invention relates to compounds of formula I wherein the piperidinyl or piperazinyl is in the 5 position. The most preferred embodiment of the invention relates to compounds of formula I wherein the piperidinyl or piperazinyl is in the 8 position. Another possibility is that the piperidinyl or piperazinyl is in the 6 or 7 position.

Another preferred embodiment of the invention relates to compounds of formula I wherein Y is NHCO or CONH i.e. amides. Of those compounds, the compounds wherein $R_3$ is unsubstituted phenyl, or mono- or di-substituted phenyl, and especially ortho-, meta- or para-substituted phenyl, and particularly those wherein the substituent $R_4$ is phenyl, phenyl-$C_1-C_6$ alkyl, cyclohexyl, piperidino, 1-piperazinyl, morpholino, $CF_3$, 4-piperidon-1-yl, n-butoxy or $COR_8$ wherein $R_8$ is phenyl, cyclohexyl, 4-piperidon-1-yl, 1-piperazinyl, morpholino, $CF_3$, piperidino or $NR_6R_7$, are preferred.

Examples of suitable combinations of substituents are:

X is N, Y is $CONR_2$, $R_1$ is H, $CH_3$, $C_2H_5$ or $C_3H_7$, $R_2$ is H, $R_3$ is $(CH_2)_2$-phenyl, $R_4$ is piperidinyl, $R_5$ is H;

X is N, Y is $NR_2CO$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ is H;

X is N, Y is $NR_2CO$, $R_1$ is H, $CH_3$, $C_2H_5$ or $C_3H_7$, $R_2$ is H, $R_3$ is phenyl, $R_4$ is piperidinyl, $R_5$ is H;

X is CH, Y is $CONR_2$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H;

X is CH, Y is $NR_2CO$, $R_1$ is H, $CH_3$, $C_2H_5$ or $C_3H_7$, $R_2$ is H, $R_3$ is phenyl, $R_4$ is piperidinyl, $R_5$ is H;

X is N, Y is $NR_2CO$, $R_1$ is H, $CH_3$, $C_2H_5$ or $C_3H_7$, $R_2$ is H, $R_3$ is $(CH_2)_2$-phenyl;

X is CH, Y is $CONR_2$, $R_1$ is H, $CH_3$, $C_2H_5$ or $C_3H_7$, $R_2$ is H, $R_3$ is $(CH_2)$-phenyl;

X is N, Y is $NR_2CO$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H;

X is CH, Y is $NR_2CO$, $R_1$ is H, $CH_3$, $C_2H_5$ or $C_3H_7$, $R_2$ is H, $R_3$ is phenyl, $R_4$ is morpholinyl, $R_5$ is H;

X is CH, Y is $CONR_2$, $R_1$ is H, $CH_3$, $C_2H_5$ or $C_3H_7$, $R_2$ is H, $R_3$ is phenyl, $R_4$ is morpholinyl, $R_5$ is H;

X is CH, Y is $CONR_2$, $R_1$ is H, $CH_3$, $C_2H_5$ or $C_3H_7$, $R_2$ is H, $R_3$ is phenyl, $R_4$ is piperidinyl, $R_5$ is H;

X is N, Y is $CONR_2$, $R_1$ is H, $CH_3$, $C_2H_5$ or $C_3H_7$, $R_2$ is H, $R_3$ is $CH_2$-phenyl, $R_4$ is morpholinyl, $R_5$ is H;

X is N, Y is $NR_2CO$, $R_1$ is H, $CH_3$, $C_2H_5$ or $C_3H_7$, $R_2$ is H, $R_3$ is $CH_2$-phenyl, $R_4$ is morpholinyl, $R_5$ is H;

X is CH, Y is $NR_2CO$, $R_1$ is H, $CH_3$, $C_2H_5$ or $C_3H_7$, $R_2$ is H, $R_3$ is $(CH_2)_2$-phenyl, $R_4$ is piperidinyl, $R_5$ is H;

X is CH, Y is $CONR_2$, $R_1$ is H, $CH_3$, $C_2H_5$ or $C_3H_7$, $R_2$ is H, $R_3$ is phenyl;

X is N, Y is $CONR_2$, $R_1$ is H, $CH_3$, $C_2H_5$ or $C_3H_7$, $R_2$ is H, $R_3$ is phenyl, $R_4$ is morpholinyl, $R_5$ is H;

X is N, Y is $CONR_2$, $R_1$ is H, $CH_3$, $C_2H_5$ or $C_3H_7$, $R_2$ is H, $R_3$ is phenyl, $R_4$ is piperidinyl, $R_5$ is H;

X is CH, Y is $NR_2CO$, $R_1$ is H, $CH_3$, $C_2H_5$ or $C_3H_7$, $R_2$ is H, $R_3$ is $(CH_2)$-phenyl;

X is CH, Y is $NR_2CO$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H;

X is N, Y is CONR$_2$, R$_1$ is H, CH$_3$, C$_2$H$_5$ or C$_3$H$_7$, R$_2$ is H, R$_3$ is (CH$_2$)$_2$-phenyl;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is piperidinyl, R$_5$ is H;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is piperidinyl, R$_5$ is H;

X is N, Y is CONR$_2$, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H;

X is N, Y is NR$_2$CO, R$_1$ is H, CH$_3$, C$_2$H$_5$ or C$_3$H$_7$, R$_2$ is H, R$_3$ is phenyl, R$_4$ is morpholinyl, R$_5$ is H;

X is CH, Y is CONR$_2$, R$_1$ is H, CH$_3$, C$_2$H$_5$ or C$_3$H$_7$, R$_2$ is H, R$_3$ is CH$_2$-phenyl R$_4$ is piperidinyl, R$_5$ is H;

X is N, Y is CONR$_2$, R$_1$ is H, CH$_3$, C$_2$H$_5$ or C$_3$H$_7$, R$_2$ is H, R$_3$ is CH$_2$-phenyl;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is morpholinyl, R$_5$ is H;

X is N, Y is CONR$_2$, R$_1$ is H, CH$_3$, C$_2$H$_5$ or C$_3$H$_7$, R$_2$ is H, R$_3$ is phenyl, R$_4$ is COR$_8$, R$_8$ is morpholinyl;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is morpholinyl, R$_5$ is H;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H;

X is N, Y is NR$_2$CO, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is piperidinyl, R$_5$ is H;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is COR$_8$, R$_8$ is NR$_6$R$_7$, R$_6$R$_7$CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is phenyl, R$_4$ is phenyl, R$_4$ is phenyl, phenylmethyl or phenylethyl, R$_5$ is H;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is morpholinyl, R$_5$ is H;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is morpholinyl, R$_5$ is H;

X is N, Y is NR$_2$CO, R$_1$ is H, CH$_3$, C$_2$H$_5$ or C$_3$H$_7$, R$_2$ is H, R$_3$ is phenyl, R$_4$ is COR$_8$, R$_8$ is morpholinyl;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H;

X is CH, Y is CONR$_2$, R$_1$ is H, CH$_3$, C$_2$H$_5$ or C$_3$H$_7$, R$_2$ is H, R$_3$ is CH$_2$-phenyl, R$_4$ is morpholinyl, R$_5$ is H;

X is CH, Y is NR$_2$CO, R$_1$ is H, CH$_3$, C$_2$H$_5$ or C$_3$H$_7$, R$_2$ is H, R$_3$ is phenyl;

X is N, Y is NR$_2$CO, R$_1$ is H, CH$_3$, C$_2$H$_5$ or C$_3$H$_7$, R$_2$ is H, R$_3$ is phenyl;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is piperidinyl, R$_5$ is H;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is piperidinyl, R$_5$ is H;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is morpholinyl, R$_5$ is H;

X is N, Y is CONR$_2$, R$_1$ is H, CH$_3$, C$_2$H$_5$ or C$_3$H$_7$, R$_2$ is H, R$_3$ is phenyl, R$_4$ is COR$_8$, R$_8$ is cyclohexyl;

X is N, Y is CONR$_2$, R$_1$ is H, CH$_3$, C$_2$H$_5$ or C$_3$H$_7$, R$_2$ is H, R$_3$ is phenyl;

X is N, Y is NR$_2$CO, R$_1$ is H, CH$_3$, C$_2$H$_5$ or C$_3$H$_7$, R$_2$ is H, R$_3$ is CH$_2$-phenyl.

Preferred compounds are:

(R)-N-[8-(4-Methylpiperazin-1-yl)-1,2,3,4-tetrahydro-2-naphthyl]-4-(trifluoroacetyl)benzamide,
(R)-N-[8-(1-Methylpiperidin-4-yl)-1,2,3,4-tetrahydro-2-naphthyl]-4-morpholinobenzamide,
(R)-N-[8-(4-Methylpiperazin-1-yl)-1,2,3,4-tetrahydro-2-naphthyl]-4-piperidinobenzamide,
(S)-N-[8-(4-Methylpiperazin-1-yl)-1,2,3,4-tetrahydro-2-naphthyl]-4-N,N-diethylaminobenzamide,
(R)-N-[8-(4-Propylpiperazin-1-yl)-1,2,3,4-tetrahydro-2-naphthyl]-4-morpholinobenzamide,
(R)-N-[8-(4-Methylpiperazin-1-yl)-1,2,3,4-tetrahydro-2-naphthyl]-4-ethylbenzamide,
(R)-N-[8-(4-Methylpiperazin-1-yl)-1,2,3,4-tetrahydro-2-naphthyl]-4-morpholinocarbonylbenzamide,
(R)-N-[8-(4-Methylpiperazin-1-yl)-1,2,3,4-tetrahydro-2-naphthyl]-4-morpholinobenzarnide,
(R)-N-[8-(4-Methylpiperazin-1-yl)-1,2,3,4-tetrahydro-2-naphthyl]-4-butoxybenzamide,
(R)-N-[8-(4-Methylpiperazin-1-yl)-1,2,3,4-tetrahydro-2-naphthyl]-4-(1H-pyrrol-1-yl)benzamide,
(R)-N-[8-(4-Methylpiperazin-1-yl)-1,2,3,4-tetrahydro-2-naphthyl]-3-methyl-4-morpholinobenzamide,
(R)-N-[8-(4-Methylpiperazin-1-yl)-1,2,3,4-tetrahydro-2-naphthyl]-4-(4-ethylphenyl)benzamide,
(R)-N-[8-(4-Methylpiperazin-1-yl)-1,2,3,4-tetrahydro-2-naphthyl]-4-trifluoromethylbenzamide,
(R)-N-[8-(4-Methylpiperazin-1-yl)-1,2,3,4-tetrahydro-2-naphthyl]-4-(N,N-dipropylaminosulphony)benzamide,
(R)-N-[8-(4-Ethylpiperazin-1-yl)-1,2,3,4-tetrahydro-2-naphthyl]-4-morpholinobenzamide,
(R)-N-[8-(1-Methylpiperidin-4-yl)-1,2,3,4-tetrahydro-2-naphthyl]-4-trifluoromethylbenzamide,
(R)-N-[8-(1-Methylpiperidin-4-yl)-1,2,3,4-tetrahydro-2-naphthyl]-4-butoxybenzamide,
(R)-N-[8-(4-Methylpiperazin-1-yl)-1,2,3,4-tetrahydro-2-naphthyl]-4-cyclohexylbenzamide,
(R)-N-[8-(Methylpiperazin-1-yl)-1,2,3,4-tetrahydro-2-naphthyl]-4-(4-piperidon-1-yl)benzamide,
(R)-N-8-(Piperazin-1-yl)-1,2,3,4-tetrahydro-2-naphthyl]-4-morpholinobenzamide,
N-(4-Morpholinocarbonylphenyl)-8-[4-(methylpiperazin-1-yl)]-1,2,3,4-tetrahydronaphthalene-2-carboxamide,
(R)-N-[8-(4-Methylpiperazin-1-yl)-1,2,3,4-tetrahydro-2-naphthyl]-4-(4-morpholinomethyl)benzamide,
(R)-N-[8-(4-Methylpiperazin-1-yl)-1,2,3,4-tetrahydro-2-naphthyl]-4-(N,N-dimethylaminocarbonyl)benzamide,
(R)-N-[8-(4-Methylpiperazin-1-yl)-1,2,3,4-tetrahydro-2-naphthyl]-4-morpholinocarbonylbenzamide or
(R)-N-[8-(4-Methylpiperazin-1-yl)-1,2,3,4-tetrahydro-2-naphthyl]-4-thiomorpholinobenzamide Another preferred group of compounds is:

(R)-N-[8-(4-Methylpiperazin-1-yl)-1,2,3,4-tetrahydro-2-naphthyl]-2-methylbenzamide
(R)-N-[8-(4-Methylpiperazin-1-yl)-1,2,3,4-tetrahydro-2-naphthyl]-4-cyanobenzamide
(R)-N-[8-(4-Methylpiperazin-1-yl)-1,2,3,4-tetrahydro-2-naphthyl]-4-fluorobenzamide
(R)-N-[8-(4-Methylpiperazin-1-yl)-1,2,3,4-tetrahydro-2-naphthyl]-4-(4-hydroxyphenyl)benzamide and
(R)-N-[8-(4-Methylpiperazin-1-yl)-1,2,3,4-tetrahydro-2-naphthyl]-3-phenoxybenzamide The compounds of the present invention are in the form of the racemate or the (R)- or (S)-enantiomer in the form of a free base or a pharmaceutically acceptable salt or hydrate thereof. Compounds in the form of the (R)-enantiomer are preferred ones.

Both organic and inorganic acids can be employed to form non-toxic pharmaceutically acceptable acid addition salts of the compounds of this invention. Illustrative acids are sulfuric, nitric, phosphoric, oxalic, hydrochloric, formic, hydrobromic, citric, acetic, lactic, tartaric, dibenzoyltartaric, diacetyltartaric, palmoic, ethanedisulfonic, sulfamic, succinic, propionic, glycolic, malic, gluconic, pyruvic, phenylacetic, 4-aminobenzoic, anthranilic, salicylic, 4-aminosalicylic, 4-hydroxybenzoic, 3,4-dihydroxybenzoic, 3,5-dihydroxybenzoic, 3-hydroxy-2-naphthoic, nicotinic, methanesulfonic, ethanesulfonic, hydroxyethanesulfonic, benzenesulfonic, p-toluenesulfonic, sulfanilic, naphthalenesulfonic, ascorbic, cyclohexylsulfamic, fumaric, maleic and benzoic acids. These salts are readily prepared by methods known in the art.

Pharmaceutical Formulations

In a second aspect the present invention provides a pharmaceutical formulation comprising as active ingredient a therapeutically effective amount of the compound of formula I as an enantiomer or a racemate in the form of a free base or a pharmaceutically acceptable salt or hydrate thereof, optionally in association with diluents, excipients or inert carriers.

According to the present invention the compound of the invention will normally be administered orally, rectally or by injection, in the form of pharmaceutical formulations comprising the active ingredient either as a free base or a pharmaceutically acceptable non-toxic acid addition salt, e.g. the hydrochloride, hydrobromide, lactate, acetate, phosphate, sulfate, sulfamate, citrate, tartrate, oxalate and the like in a pharmaceutically acceptable dosage form. The dosage form may be a solid, semisolid or liquid preparation. Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical formulations containing the compound of the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatin or polyvinylpyrrolidone, or a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatin, talcum, titanium dioxide, and the like. Alternatively, the tablet can be coated with a polymer known to the person skilled in the art, dissolved in a readily volatile organic solvent or mixture of organic solvents. Dyestuffs may be added to these coatings in order to readily distinguish among tablets containing different active substances or different amounts of the active compound.

For the preparation of soft gelatin capsules, the active substance may be admixed with e.g. a vegetable oil or poly-ethylene glycol. Hard gelatin capsules may contain granules of the active substance using either the above mentioned excipients for tablets e.g. lactose, saccharose, sorbitol, mannitol, starches (e.g. potato starch, corn starch or amylopectin), cellulose derivatives or gelatin. Also liquid or semisolid forms of the drug can be filled into hard gelatin capsules.

Dosage units for rectal application can be solutions or suspensions or can be prepared in the form of suppositories comprising the active substance in a mixture with a neutral fatty base, or in the form of gelatin rectal capsules comprising the active substance in admixture with vegetable oil or paraffin oil. Liquid preparations for oral application may be in the form of syrups or suspensions, for example solutions containing from about 0.1% to about 20% by weight of the active substance herein described, the balance being sugar and a mixture of ethanol, water, glycerol and propylene glycol. Optionally such liquid preparations may contain colouring agents, flavouring agents, saccharin and carboxymethyl-cellulose as thickening agent or other excipients known to the person skilled in the art.

Solutions for parenteral applications by injection can be prepared in an aqueous solution of a water-soluble pharmaceutically acceptable salt of the active substance, preferably in a concentration of from about 0.1% to about 10% by weight. These solutions may also contain stabilizing agents and/or buffering agents and may conveniently be provided in various dosage unit ampoules.

Suitable daily doses of the compound of the invention in therapeutical treatment of humans are about 0.01–100 mg/kg body weight for peroral administration and 0.001–100 mg/kg body weight for parenteral administration.

Medical and Pharmaceutical Use

In a further aspect the present invention provides the use of the compounds of formula I in therapy as $5\text{-HT}_{1D}$ antagonists, partial agonists or full agonists, preferably as antagonists and the use in the treatment of 5-hydroxytryptamine mediated disorders. Examples of such disorders are disorders in the CNS such as mood disorders (depression, major depressive episodes, dysthymia, seasonal affective disorder, depressive phases of bipolar disorder), anxiety disorders (obsessive compulsive disorder, panic disorder with/without agoraphobia, social phobia, specific phobia, generalized anxiety disorder, posttraumatic stress disorder), personality disorders (disorders of impulse control, trichotellomania), obesity, anorexia, bulimia, premenstrual syndrome, sexual disturbances, alcoholism, tobacco abuse, autism, attention deficit, hyperactivity disorder, migraine, memory disorders (age associated memory impairment, presenile and senile dementia), pathological aggression, schizophrenia, endocrine disorders (e g hyperprolactinaemia), stroke, dyskinesia, Parkinson's disease, thermoregulatory disorders, pain and hypertension. Other examples of 5-hydroxytryptamine mediated disorders are urinary incontinence, vasospasm and growth control of tumors (e g lung carcinoma).

Methods of Preparation

The present invention also relates to processes for preparing the compounds of formula (I). Throughout the following description of such processes it is understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis" T. W. Greene, Wiley-Interscience, New York, 1991.

The below described methods for substitution in the 8-position are also applicable to substitution in the 5-position.

Methods of Preparation of Intermediates 1.
(i) Benzylation of the compound of the formula (II), either as a racemate or as an enantiomer,

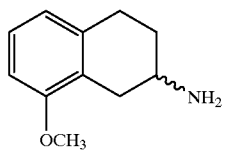
(II)

to obtain a compound of formula (III) may be carried out by reaction with a suitable benzylation agent e.g. a benzyl halide such as benzyl bromide or benzyl chloride or an activated alcohol e.g. benzylmesylate or benzyltosylate. The reaction may be carried out using a salt or the base of compound (II) in a suitable solvent e.g. N,N-dimethylformamide, acetone or acetonitrile with a suitable base e.g. NaOH, NaHCO$_3$, K$_2$CO$_3$ or a trialkylamine such as triethylamine at a temperature within the range of +20° C. to +150° C. The presence of a suitable catalyst e.g. potassium iodide or sodium iodide, may increase the speed of the reaction. The nitrogen in compound (II) may also be protected by reductive alkylation with an arylaldehyde in the presence of a reductive agent such as sodium cyanoborohydride, sodium borohydride or catalytically with H$_2$ and a suitable catalyst containing palladium, platinium, rhodium or nickel in a suitable solvent e.g. tetrahydrofuran, dioxane, methanol or ethanol. A proton donor such as p-toluenesulfonic acid can be used to catalyze the formation of the imine/enarnine, and adjustment of pH to slightly acidic by an appropriate acid such as acetic acid may speed up the reaction, resulting in compound (III).

(ii) Demethylation of the compound of formula (III)

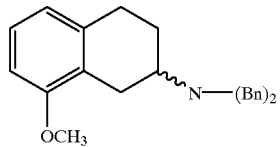
(III)

to obtain a compound of formula (IV) may be carried out by treating the compound with an acidic reagent such as aqueous HBr, HI, HBr/CH$_3$COOH, BBr$_3$, AlCl$_3$, pyridine-HCl or with a basic nucleophilic reagent such as CH$_3$C$_6$H$_4$S$^-$ or C$_2$H$_5$S$^-$ in a suitable solvent. Suitable solvents may be methylene chloride or chloroform and the reaction may occur between −78° C. and +60° C.

(iii) Conversion of the compound of formula (IV) to a compound of formula (V)

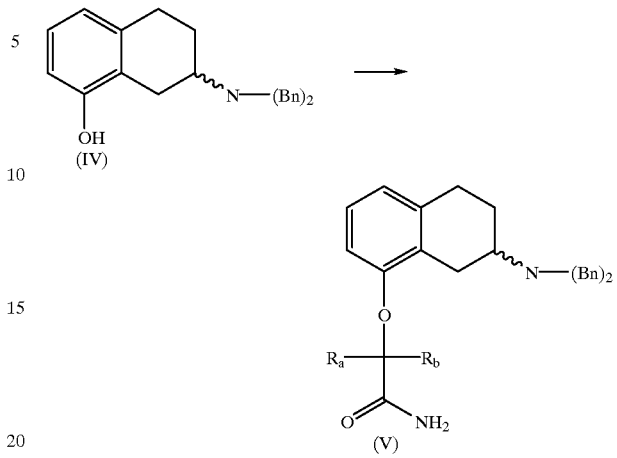

may be carried out by the reaction with a compound of formula (VI)

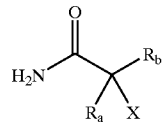
(VI)

where X stands for a leaving group, e.g. a halogen such as chlorine, bromine or iodine or an alkane- or arenesulfonyloxy group such as a p-toluenesulfonyloxy group and R$_a$ and R$_b$ are hydrogen or a lower alkyl group e.g. methyl. The process may be carried out with a salt of the compound of formula (IV) obtained by reaction with a base such as K$_2$CO$_3$, Na$_2$CO$_3$, KOH, NaOH, BuLi or NaH. The reaction may be conducted in a suitable solvent e.g. an aprotic solvent such as dioxane, N,N-dimethylformamide, tetrahydrofuran, toluene, benzene or petroleum ether and the reaction may occur between +20° C. and +150° C.

(iv) Rearrangement of a compound of formula (V) to a compound of formula (VII)

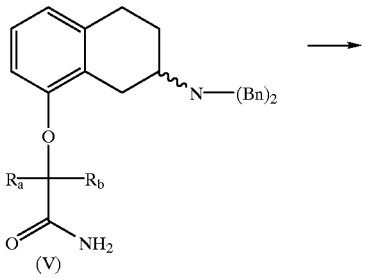
(V)

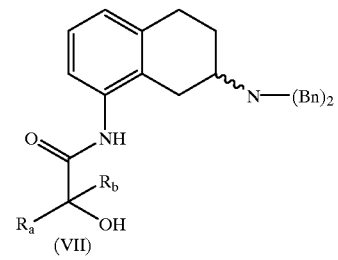
(VII)

may be carried out in a suitable solvent e.g. aprotic solvent such as N,N dimethylformamide, dioxane, 1,1,3,3-tetramethylurea, tetrahydrofuran or hexamethylphosphoric triamide with a suitable base e.g. $K_2CO_3$, KOH, potassium tert-butoxide or NaH at a temperature within the range of +20° C. to +150° C. The presence of a cosolvent such as 1,3-dimethyl-3,4,5,6-tetrahydro-2(1H)-pyrimidone or hexamethylphosphoric triamide in appropriate concentration in the solvent may increase the speed of the reaction.

(v) Hydrolysis of a compound of formula (VII) to a compound (VIII) may be carried out under acidic conditions using acids such as $H_2SO_4$, HCl or HBr in a suitable solvent e.g. $H_2O$, ethanol, methanol or mixtures thereof and the reaction may occur between +20° C. and +100° C. or under basic conditions using bases such as NaOH or KOH in a suitable solvent e.g. $H_2O$, ethanol, methanol or mixtures thereof and the reaction may occur between +20° C. and +100° C.

(vi) Conversion of compound of formula (VIII) to a compound of formula (IX)

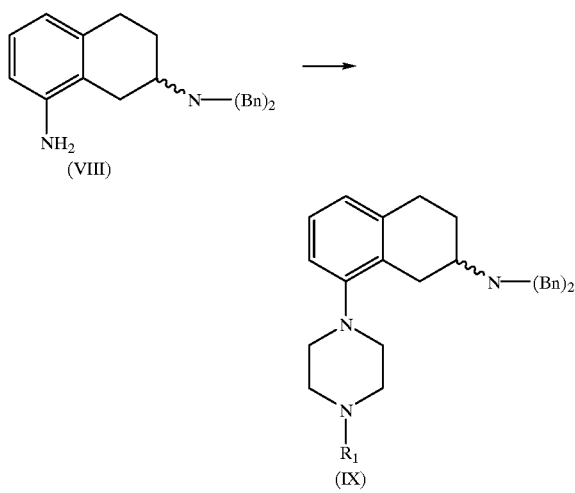

may be carried out by a) reaction with a compound of formula (X)

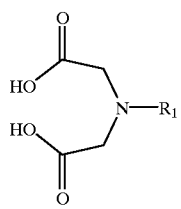

where $R_1$ is $C_1$–$C_6$ alkyl or $C_3$–$C_6$ cycloalkyl. The process may be carried out in a suitable solvent e.g. an aprotic/anhydrous solvent such as tetrahydrofuran or N,N-dimethylformamide in the presence of coupling reagent such as N,N'-carbonyldiimidazole and the reaction may occur between +20° C. and +130° C. The reaction is followed by the reduction of the imide with a suitable reducing agent e.g. $LiAlH_4$ in a suitable solvent e.g. diethyl ether or tetrahydrofuran at a temperature between +20° C. and reflux, or b) by reaction with a compound of formula (XI)

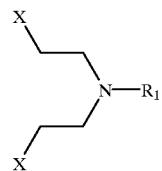

where X stands for a leaving group, e.g. a halogen such as chlorine or bromine or an alkane- or arenesulfonyloxy group such as p-toluenesulfonyloxy group and $R_1$ is $C_1$–$C_6$-alkyl or $C_3$–$C_6$ cycloalkyl. The process may be carried out in a suitable solvent such as ethanol, buthanol, N,N-dimethylformamide, acetonitrile or a mixture of water and acetonitrile with a suitable base e.g. $K_2CO_3$, $NaHCO_3$ or KOH and the reaction may occur between +20° C. and +150° C.

Alternatively, a compound of formula (IX) may be prepared by, (vii) Benzylation of the compound of the formula (XV), either as a racemate or as an enantiomer,

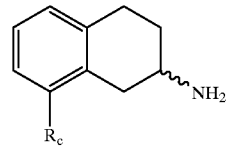

where $R_c$ stands for a halogen such as bromine, iodine or a trifluoromethylsulfonyloxy group, to obtain a compound of formula (XVI) by reaction with a suitable benzylating agent e.g. benzyl halide such as benzyl bromide or benzyl chloride or an activated alcohol e.g. benzylmesylate or benzyltosylate. The reaction may be carried out by using the salt or the base of compound (XV) in a suitable solvent e.g. N,N-dimethylformamide, acetone or acetonitrile with a suitable base e.g. NaOH, $NaHCO_3$, $K_2CO_3$ or a trialkylamine such as triethylamine at a temperature within the range of +20° C. to +150° C. The presence of suitable catalyst e.g. alkali metal iodide such as potassium iodide or sodium iodide may increase the speed of the reaction.

The nitrogen in compound (XV) may also be protected by reductive alkylation with an arylaldehyde in the presence of a reductive agent such as sodium cyanoborohydride, sodium borohydride or catalytically with $H_2$ and a suitable catalyst containing palladium, platinium, rhodium or nickel in a suitable solvent e.g. tetrahydrofuran, dioxane, methanol or ethanol. A proton donor such as p-toluenesulfonic acid can be used to catalyze the formation of the imine/enamine and adjustment of pH to slightly acidic by an appropriate acid such as acetic acid may speed up the reaction, resulting in compound (XVI).

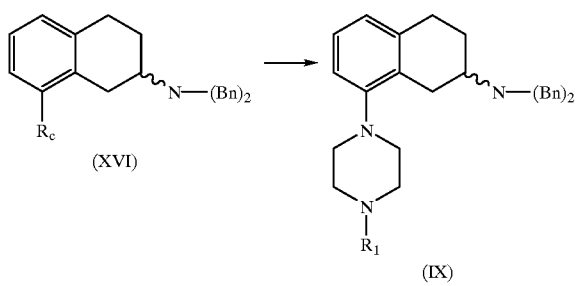

(viii) Conversion of the compound of formula (XVI) to a compound of formula (IX), where $R_1$ is $C_1$–$C_6$ alkyl or $C_3$–$C_6$ cycloalkyl, may be carried out by reaction with a compound of formula (XVII).

The process may be carried out in a suitable solvent e.g. an aprotic solvent such as benzene, toluene, dioxane, tetrahydrofuran or N,N-dimethylforinamide with a suitable base such as sodium tert-butoxide or lithium bis(trimethylsilyl)amide in the presence of a suitable palladium catalyst such as $PdX_2$, $L_2Pd(0)$ or $L_2PdX_2$ where X stands for a halogen such as chlorine or bromine and L stands for a suitable ligand such as triphenylphosphine, tri-o-tolylphosphine, trifurylphosphine, triphenylarsine or dibenzylidenacetone and with or without an addition of a ligand L' such as triphenylphosphine, tri-o-tolylphosphine, trifurylphdsphine, 2,2'-bis(diphenylphosphino)-1,1'-binaphthalene (either as a racemate or as an enantiomer) or triphenylarsine and the reaction may occur at a temperature between +20° C. and +150° C., resulting in the compound of the formula (IX).

The conversion of (XVI) to (IX) can also proceed via the tranformation of (XVII) to an aminostannane or aminoborane using agents such as (N,N-diethylamino)tributyltin and tris(dimethylamino)borane in a suitable solvent e.g an aprotic solvent such as benzene, toluene, dioxan, tetrahydrofuran or N,N-dimethylformamide and then using similar conditions as described in the above description, resulting in the compound of the formula (IX).

Compound of formula (IX) may also be prepared by, (ix) Alkylation of a compound of formula (XIII), wherein $R_1$ is hydrogen, with a suitable alkylation reagent such as $R_1$—L where L is a suitable leaving group e.g. a halogen such as chlorine, bromine or iodine or an alkane- or arenesulfonyloxy group such as a p-toluenesulfonyloxy group and $R_1$ is $C_1$–$C_6$ alkyl. The reaction may be carried out in a suitable solvent such as N,N-dimethylformamide, acetone, acetonitrile or tetrahydrofuran with a suitable base such as $K_2CO_3$, $NaHCO_3$, NaOH or a trialkylamine such as triethylamine. The reaction may be conducted at a temperature between +20° C. and +120° C.

Alternatively, (x) conversion of a compound of formula (XIII), wherein $R_1$ is hydrogen, to a compound of formula (IX) may be carried out by reductive alkylation with a compound $R_1$—CHO, where $R_1$ is hydrogen or $C_1$–$C_5$ alkyl, or with a $C_3$–$C_6$ cyclic ketone, in the presence of a reductive agent such as sodium cyanoborohydride, sodium borohydride or catalytically with $H_2$ and a suitable catalyst containing palladium, platinum, rhodium or nickel in a suitable solvent e.g. tetrahydrofuran, dioxane, methanol or ethanol. A proton donor such as p-toluenesulfonic acid can be used to catalyze the formation of the imine/enamine and adjustment of pH to slightly acidic by an appropriate acid such as acetic acid may speed up the reaction, resulting in compound (IX).

(xi) In the case where $R_1$ is methyl, conversion of a compound of formula (XIII) to a compound of formula (IX) may be carried out by

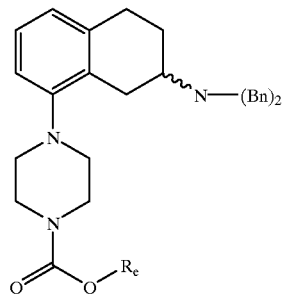

a) conversion of the compound of formula (XIII) to a compound of formula (XLVI), where $R_e$ is $C_1$–$C_6$ alkyl, with a reagent such as an alkyl chloroformate e.g. ethyl chloroformate in a solvent such as methylene chloride, chloroform, dioxane or diethyl ether with a suitable base such as $K_2CO_3$, $NaHCO_3$, NaOH or a trialkylamine such as triethylamine at a reaction temperature between −20° C. and +60° C. followed by, b) reduction of the compound of formula (XLVI) to a compound of formula (IX) with an appropriate reductive agent such as lithium aluminum hydride in a suitable solvent e.g. diethyl ether or tetrahydrofuran at a temperature between +20° C. and reflux.

(xii) Conversion of the compound of formula (IX) to a compound of formula (XII)

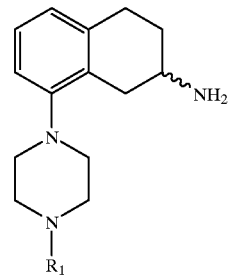

where $R_1$ is $C_1$–$C_6$ alkyl or $C_3$–$C_6$ cycloalkyl may be carried out by a) hydrogenation using a catalyst containing palladium, platinum, rhodium or nickel in a suitable solvent e.g. acetic acid or ethanol and at a reaction temperature between +20° C. and +120° C., or b) debenzylation in a suitable solvent such as methanol in the presence of ammonium formate and Pd/C and at a reaction temperature between +20° C. and reflux.

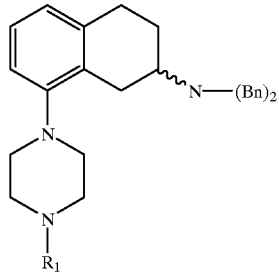

(XIII)

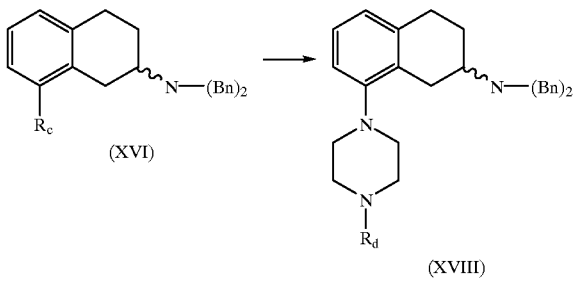

(xiii) In the case when $R_1$ is hydrogen, conversion of compound of formula (VIII) to a compound of formula (XIII) may be carried out by reaction with a compound of formula (XI) where X stands for a leaving group, e.g. a halogen such as chlorine or bromine or an alkane- or arenesulfonyloxy group such as p-toluenesulfonyloxy group and $R_1$ is hydrogen. The process may be carried out in a suitable solvent such as ethanol, butanol, N,N-dimethylformamide, acetonitrile or a mixture of water and acetonitrile with a suitable base e.g. $K_2CO_3$, $NaHCO_3$ or KOH and the reaction may occur between +20° C. and +150° C.

(xiv) Conversion of a compound of formula (XIII), where $R_1$ is hydrogen, to a compound of formula (XIV), (xv) Conversion of the compound of formula (XVI) to a compound of formula (XVIII), where $R_d$ is a suitable protecting group such as a benzyl or tert-butyloxycarbonylgroup, may be carried out by the reaction with a compound of formula (XIX).

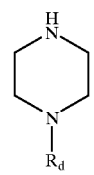

(XIX)

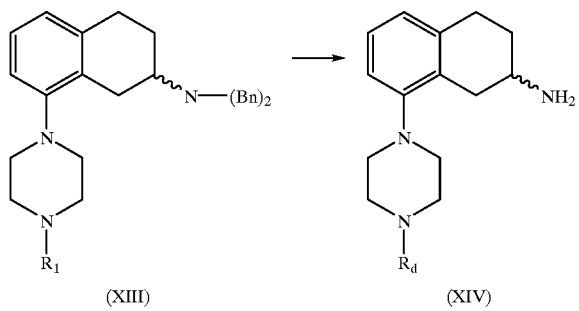

(XIII)          (XIV)

where $R_d$ stands for a suitable protecting group, may be carried out by a) hydrogenation using a catalyst containing palladium, platinum, rhodium or nickel in a suitable solvent e.g. acetic acid or ethanol at a reaction temperature between +20° C. and +120° C., or b) debenzylation in a suitable solvent such as methanol in the presence of ammonium formate and Pd/C at a reaction temperature between +20° C. and reflux.

Said reaction is followed by the protection of the piperazine ring in a suitable solvent e.g. methylene chloride or chloroform with an appropriate protecting reagent e.g. di-tert-butyl dicarbonate with a suitable base e.g. triethylamine or $K_2CO_3$ and at a temperature between −20° C. and +60° C., resulting in compound of formula (XIV).

Alternatively, a compound of formula (XIV) may be prepared by,

The process may be carried out in a suitable solvent e.g. an aprotic solvent such as benzene, toluene, dioxane, tetrahydrofuran or N,N-dimethylformamide with a suitable base such as sodium tert-butoxide or lithium bis (trimethylsilyl)amide in the presence of a suitable palladium catalyst such as $PdX_2$, $L_2Pd(0)$ or $L_2PdX_2$ where X stands for a halogen such as chlorine or bromine and L stands for a suitable ligand such as triphenylphosphine, tri-o-tolylphosphine, trifurylphosphine, triphenylarsine or dibenzylidenacetone and with or without an addition of a ligand L' such as triphenylphosphine, tri-o-tolylphosphine, trifurylphosphine, 2,2'-bis(diphenylphosphino)-1,1'-binaphthalene (either as a racemate or as an enantiomer) or triphenylarsine and the reaction may occur at a temperature between +20° C. and +150° C., resulting in the compound of the formula (XVIII).

The conversion of (XVI) to (XVIII) can also proceed via the tranformation of (XIX) to an aminostannane or aminoborane using agents such as (N,N-diethylamino) tributyltin and tris(dimethylamino)borane in a suitable solvent e.g an aprotic solvent such as benzene, toluene, dioxane, tetrahydrofuran or N,N-dimethylformamide and then using similar conditions as described in the above description, resulting in the compound of the formula (XVIII).

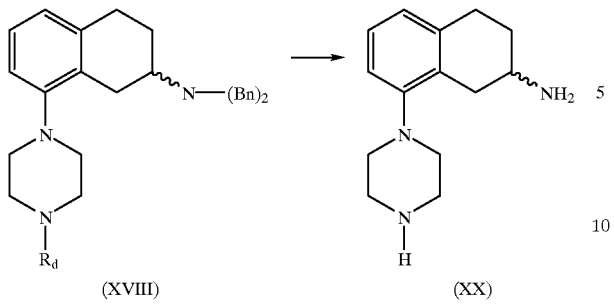

(XVIII)　　　　　　　　(XX)

(xvi) Conversion of the compound of formula (XVII) to a compound of formula (XX) may be carried out by removal of the protecting group $R_d$ of the compound of formula (XVIII) by methods known in the art such as a) hydrolysis of a tert-butyloxycarbonylgroup in a suitable solvent e.g. methylene chloride or chloroform with a suitable acid such as trifluoroacetic acid at a temperature between +20° C. and +60° C., followed by b) cleavage of the benzyl groups by hydrogenation over a suitable catalyst containing palladium, rhodium, platinum or nickel, in a suitable solvent e.g. acetic acid or ethanol at a temperature between +20° C. and +120° C., or alternatively by, c) debenzylation in a suitable solvent such as methanol in the presence of ammonium formate and Pd/C and at a reaction temperature between +20° C. and reflux.

Said reaction is followed by the protection of the piperazine ring in a suitable solvent such as methylene chloride or chloroform with an appropriate protecting reagent e.g. di-tert-butyl dicarbonate with a suitable base such as triethylamine or $K_2CO_3$ at a temperature between −20° C. and +60° C., resulting in in the compound of formula (XIV).

2.

(i) Halogenation of the compound of formula (XXI), either as a racemate or as an enantiomer

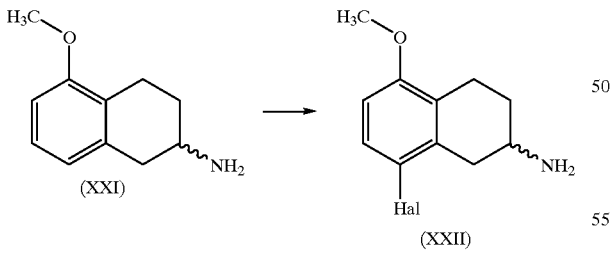

(XXI)　　　　　　　　(XXII)

to obtain a compound of formula (XXII) may be performed by aromatic electrophilic substitution using a suitable halogenation agent such as $Br_2$, $Cl_2$, $I_2$, ICl, or $SO_2Cl_2$. The reaction may be carried out using the salt or the base of the compound (XXI) in an appropriate solvent e.g. acetic acid, HCl/ethanol or water with or without a suitable base e.g. an alkali metal acetate such as sodium acetate and at a reaction temperature between −20° C. and room temperature.

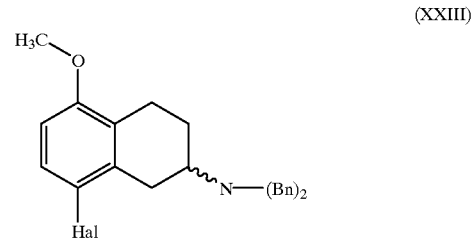

(XXIII)

(ii) Benzylation of the compound of the formula (XXII), either as a racemate or as an enantiomer, to obtain a compound of the formula (XXIII) may be carried out by reaction with a suitable benzylation agent e.g. benzyl halide such as benzyl bromide or benzyl chloride. The reaction may be carried out using the salt or the base of compound (XXII) in a suitable solvent e.g. N,N-dimethylformamide, acetone or acetonitrile with a suitable base such as triethylamine, NaOH, $NaHCO_3$ or $K_2CO_3$ at a temperature within the range of +20° C. to +150° C. The presence of a suitable catalyst e.g. an alkali metal halide such as potassium iodide or sodium iodide may increase the speed of the reaction. The nitrogen in compound (XXII) may also be protected by reductive alkylation with an arylaldehyde in the presence of a reductive agent such as sodium cyanoborohydride, sodium borohydride or catalytically with $H_2$ and a suitable catalyst containing palladium, platinum, rhodium or nickel in a suitable solvent e.g. tetrahydrofuran, dioxane, methanol or ethanol. A proton donor such as p-toluenesulfonic acid can be used to catalyze the formation of the imine/enamine and adjustment of pH to slightly acidic by an appropriate acid such as acetic acid may speed up the reaction, resulting in compound (XXIII).

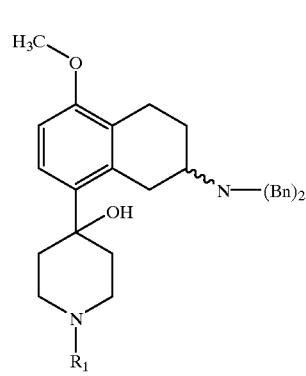

(XXIV)

iii) The conversion of the compound of the formula (XXIII) to the compound of the formula (XXIV), where $R_1$ is $C_1$–$C_6$ alkyl or $C_3$–$C_6$ cycloalkyl, may be performed by a metal-halogen exchange, in an appropriate anhydrous solvent such as tetrahydrofuran or diethyl ether using a suitable alkyl-lithium or metal e.g. butyllithium, lithium or magnesium turnings, followed by treatment with an appropriate piperidone such as N-methyl-4-piperidone and a subsequent suitable workup. The reaction may be performed at a reaction temperature within the range of −78° C. to room temperature.

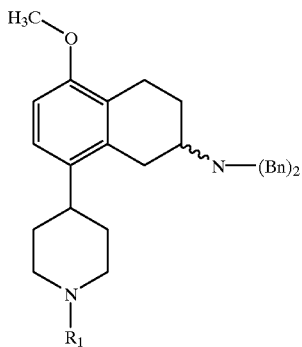

(XXV)

(iv) The compound of the (XXIV) may be reduced to the compound of the formula (XXV) by treatment with a suitable reducing agent such as sodium borohydride and a protonating agent such as $CF_3COOH$, $CF_3SO_3H$ or HCOOH in an appropriate solvent such as tetrahydrofuran or diethyl ether. The reaction may be performed at reaction temperature between 0° C. and reflux.

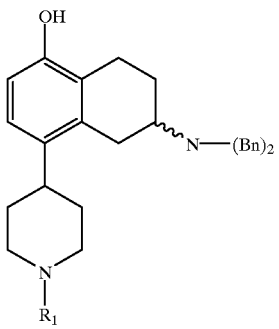

(XXVI)

(v) Demethylation of the compound of the formula (XXV) to obtain a compound of formula (XXVI) may be performed by treating the compound with an acidic reagent such as aqueous HBr, HI, HBr/acetic acid, $BBr_3$, $AlCl_3$, pyridine-HCl or with a basic nucleophilic reagent such as $C_2H_5S^-$ or $CH_3C_6H_4S^-$ in a suitable solvent. Suitable solvents may be methylene chloride or chloroform and the reaction may occur between −78° C. and +60° C.

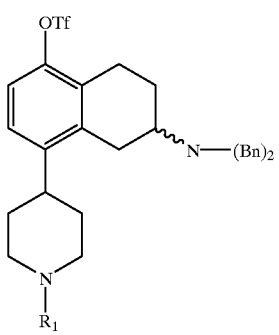

(XXVII)

(vi) Conversion of the compound of formula (XXVI) to a compound of formula (XXVII) may be carried out with a compound such as trifluoromethanesulfonic anhydride in a suitable solvent such as methylene chloride or carbon tetrachloride in the presence of a base such as 2,4,6-collidine, triethylamine or pyridine at a reaction temperature within the range of −78° C. to room temperature.

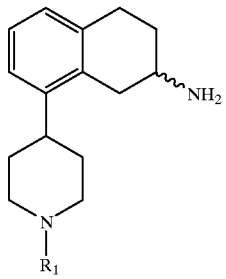

(XXVIII)

vii) Conversion of the compound of formula (XXVII) to a compound of formula (XXVIII) may be performed by a) hydrogenation using a catalyst such as palladium, platinum, rhodium or nickel in a suitable solvent such as acetic acid or ethanol at a reaction temperature between +20° C. and +120° C., or b) reaction in a suitable solvent such as methanol in the presence of ammonium formate and Pd/C at a reaction temperature between +20° C. and reflux.

Alternatively, a compound of formula (XXVIII) may be prepared by,

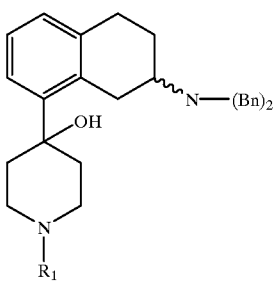

(XXIX)

(viii) The conversion of a compound of the formula (XVI), where $R_c$ is a halogen such as bromine, to a compound of the formula (XXIX), where $R_1$ is $C_1$–$C_6$ alkyl or $C_3$–$C_6$ cycloalkyl. This may be performed by a metal-halogen exchange, in an appropriate anhydrous solvent such as tetrahydrofuran or diethyl ether using a suitable alkyllithium or metal e.g. butyllithium, lithium or magnesium turnings, followed by treatment with appropriate piperidone such as N-methyl-4-piperidone and a subsequent suitable workup. The reaction may be performed at a reaction temperature within the range of −78° C. to room temperature.

(XXX)

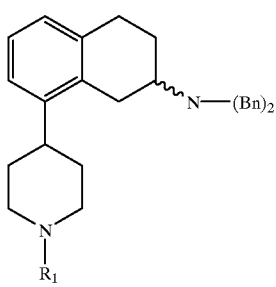

(ix) A compound of the formula (XXIX) may be reduced to a compound of the formula (XXX) by treatment with a suitable reducing agent such as sodium borohydride and a protonating agent such as $CF_3COOH$, $CF_3SO_3H$ or HCOOH in an appropriate solvent such as tetrahydrofuran or diethyl ether. The reaction may be performed at a reaction temperature between 0° C. and reflux.

(x) Conversion of a compound of formula (XXX) to a compound of formula (XXVIII), where $R_1$ is $C_1$–$C_6$ alkyl or $C_3$–$C_6$ cycloalkyl, may be performed by a) hydrogenation using a catalyst containing palladium, platinum, rhodium or nickel in a suitable solvent e.g. acetic acid or ethanol at a reaction temperature between +20° C. and +120° C., or b) debenzylation in a suitable solvent such as methanol in the presence of ammonium formate and Pd/C and at a reaction temperature between +20° C. and reflux.

3.

(i) Conversion of the compound of formula (XXXI) described in Sunkyung L.; Stewart P. F.; David E. N. *Synth. Commun.* 1995, 25(18), 2775–2780, where the protected ketone may be protected as other ketals, cyclic or acyclic, or by other protective groups known by a person skilled in the art (see T. W. Greene, Wiley-Interscience, New York, 1991), to a compound of formula (XXXII)

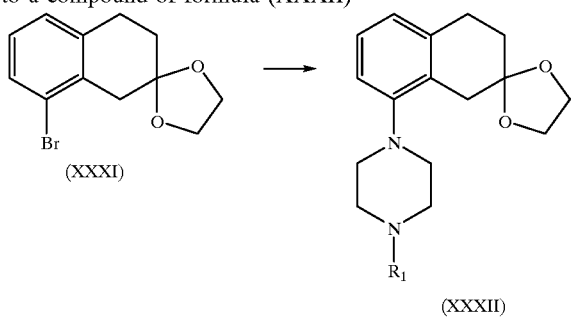

where $R_1$ is $C_1$–$C_6$ alkyl or $C_3$–$C_6$ cycloalkyl, may be carried out by the reaction with a compound of formula (XVII).

(XVII)

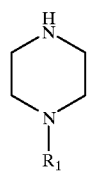

The process may be carried out in a suitable solvent e.g. an aprotic solvent such as benzene, toluene, dioxane, tetrahydrofuran or N,N-dimethylformamide with a suitable base such as sodium tert-butoxide or lithium bis (trimethylsilyl)amide in the presence of a suitable palladium catalyst such as $PdX_2$, $L_2Pd(0)$ or $L_2PdX_2$ where X stands for a halogen such as chlorine or bromine and L stands for a suitable ligand such as triphenylphosphine, tri-o-tolylphosphine, trifurylphosphine, triphenylarsine or dibenzylidenacetone and with or without an addition of a ligand L' such as triphenylphosphine, tri-o-tolylphosphine, trifulrylphosphine, 2,2'-bis(diphenylphosphino)-1,1'-binaphthalene (either as a racemate or as an enantiomer) or triphenylarsine and the reaction may occur at a temperature between 20° C. and +150° C., resulting in the compound of the formula (XXXII).

The conversion of (XXXI) to (XXXII) can also proceed via the tranformation of (XVII) to an aminostannane or aminoborane using agents such as (N,N-diethylamino) tributyltin and tris(dimethylamino)borane in a suitable solvent e.g an aprotic solvent such as benzene, toluene, dioxan, tetrahydrofuran or N,N-dimethylformamride and then using similar conditions as described in the above description, resulting in a compound of the formula (XXXII).

(XXXIII)

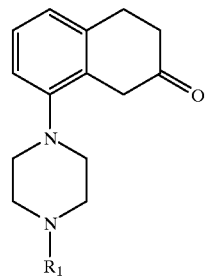

(ii) Conversion of a compound of formula (XXXII) to a compound of formula (XXXIII) may be carried out by using a suitable aqueous acid such as HCl, HBr or acetic acid at a reaction temperature between +20° C. and reflux or by other methods known by a person skilled in the art (see T. W. Greene, Wiley-Interscience, New York, 1991).

(XXXIV)

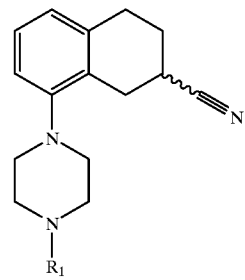

The above reaction is followed by the conversion of the ketone of the formula (XXXIII) to compound of formula (XXXIV) by the reaction with an appropriate cyanation reagent such as tosylmethyl isocyanide in the presence of suitable base e.g. potassium tert-butoxide in a suitable solvent such as 1,2-dimethoxyethane, dimethyl sulfoxide or hexamethylphosphoric triamide containing small amounts of an alcohol such as methanol, ethanol or tert-butanol at a temperature between 0° C. and +100° C. or via cyanohydrin formation and then conversion to a compound of formula (XXXIV).

(XXXV)

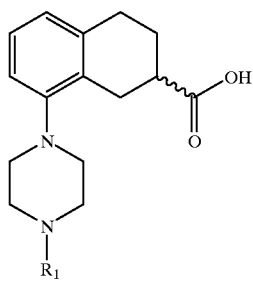

(iii) Hydrolysis of a compound of formula (XXXIV) to a compound (XXXV) may be carried out under acidic conditions using acids such as $H_2SO_4$, HCl, HBr, in a suitable solvent such as $H_2O$, ethanol, methanol, acetic acid or mixtures thereof and the reaction may occur at a temperature between +20° C. and reflux or under basic conditions using bases such as NaOH or KOH in a suitable solvent such as $H_2O$, ethanol, methanol or mixtures thereof at a temperature between +20° C. and reflux.

4.
i) Nitration of a compound of formula (XXXVI), described in Johnson D. W.; Mander L. N. *Aust. J. Chem* 1974, 27,1277–1286, either as racemate or as an enantiomer, to obtain a compound of formula (XXXVII),

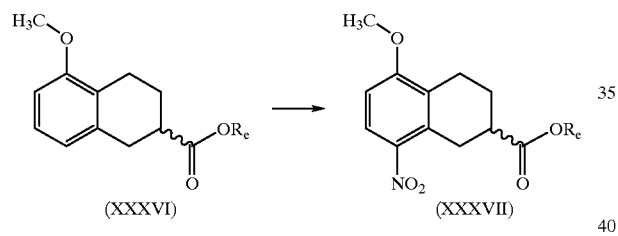

(XXXVI)      (XXXVII)

where $R_e$ is $C_1$–$C_6$ alkyl, may be carried out by aromatic electrophilic substitution using a suitable nitration reagent such as nitric acid or nitric acid and sulfuric acid in a suitable solvent e.g. acetic acid, acetic anhydride or water at a reaction temperature between –20° C. and room temperature.

(ii) Demethylation of the compound of the formula (XXXVII) to obtain a compound of formula (XXXVIII)

(XXXVIII)

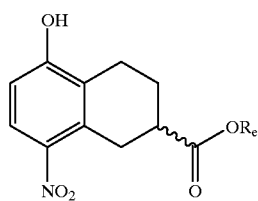

may be carried out by treating the compound with an acidic reagent such as aqueous HBr, HI, HBr/$CH_3COOH$, $BBr_3$, $AlCl_3$, pyridine-HCl or with a basic nucleophilic reagent such as $CH_3C_6H_4S^-$ or $C_2H_5S^-$. Suitable solvents may be methylene chloride or chloroform and the reaction may occur between –78° C. and +60° C.

During the demethylation of (XXXVII), hydrolysis of the ester may occur and the acid function could then be converted back to the ester by methods known by a person skilled in the art (See T. W. Greene, Wiley-Interscience, New York, 1991).

(iii) Conversion of the compound of formula (XXXVIII) to a compound of formula (XXXIX)

(XXXIX)

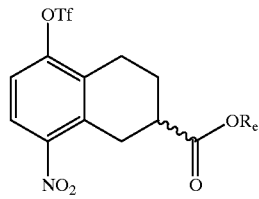

may be carried out by the reaction with an activated trifluoromethanesulfonic reagent e.g. trifluoromethanesulfonic anhydride in a suitable solvent such as methylene chloride, chloroform or carbon tetrachloride in the presence of a suitable base such as triethylamine, pyridine or 2,4,6-collidine at a reaction temperature between –78° C. and room temperature.

(iv) Conversion of the compound of formula (XXXIX) to a compound of formula (XL) may be carried out by (XL)

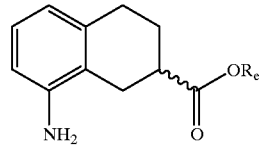

a) hydrogenation using a catalyst containing palladium, platinum or nickel in a suitable solvent such as ethanol, methanol or acetic acid and at a reaction temperature between +20° C. and +120° C. or b) reaction in a suitable solvent such as methanol in the presence of a ammonium formate such as triethyl ammonium formate and Pd/C and at a reaction temperature between +20° C. and reflux.

(v) Conversion of the compound of formula (XL) to a compound of formula (XLI)

(XLI)

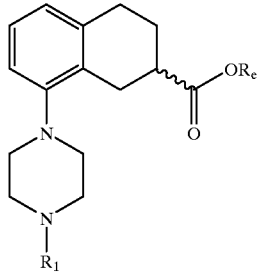

may be carried out by reaction of compound (XI)

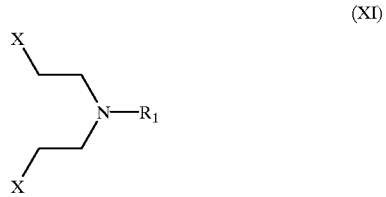

where X stands for a leaving group, e.g. a halogen such as chlorine or bromine or an alkane- or arenesulfonyloxy group such as p-toluene-sulfonyloxy group and $R_1$ is hydrogen, $C_1$–$C_6$ alkyl or $C_3$–$C_6$ cycloalkyl. The process may be carried out in a suitable solvent such as ethanol, buthanol, N,N-dimethylformamide, acetonitrile or a mixture of water and acetonitrile with a suitable base e.g. $K_2CO_3$, $NaHCO_3$ or KOH and the reaction may occur between +20° C. and +150° C. During the cyclization reaction of (XL), hydrolysis of the ester may occur.

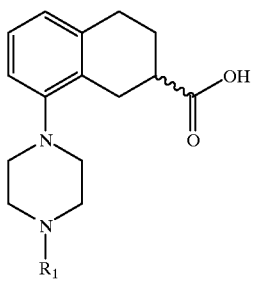

(vi) Hydrolysis of a compound of formula (XLI) may be carried out under acidic conditions using acids such as $H_2SO_4$, HCl, HBr, in a suitable solvent such as $H_2O$, ethanol, methanol, acetic acid or mixtures thereof at a temperature between +20° C. and reflux or under basic conditions using bases such as NaOH or KOH in a suitable solvent such as as $H_2O$, ethanol, methanol or mixtures thereof at a temperature between +20° C. and reflux, resulting in a compound of formula (XXXV), where $R_1$ is hydrogen, $C_1$–$C_6$ alkyl or $C_3$–$C_6$ cycloalkyl.

(vii) When $R_1$ is hydrogen, protection of a compound of formula (XXXV) as a compound of formula (XLII) where $R_d$ is a protecting group

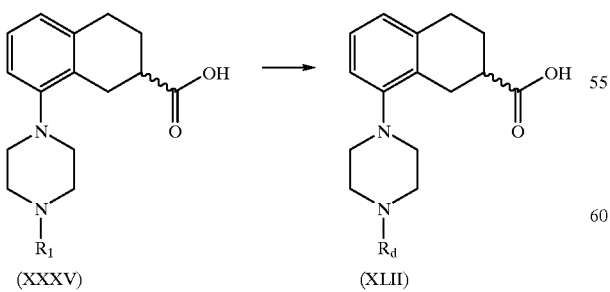

may be carried out by the reaction with a suitable protecting reagent such as di-tert-butyl dicarbonate in a suitable solvent e.g methylene chloride or chloroform with a suitable base such as triethylamine or $K_2CO_3$ and at a temperature between –20° C. and +60° C.

5.

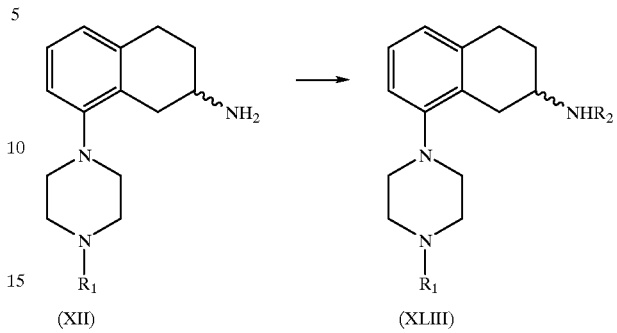

(i) Conversion of a compound of formula (XII), where $R_1$ is $C_1$–$C_6$ alkyl or $C_3$–$C_6$ cycloalkyl, to a compound of formula (XLIII) may be carried out by the alkylation of compound of formula (XII) with a suitable alkylation reagent such as $R_2$—Z where Z is a suitable leaving group e.g. a halogen such as chlorine, bromine or iodine or an alkane- or arenesulfonyloxy group such as p-toluenesulfonyloxy group and $R_2$ is $C_1$–$C_6$ alkyl. The reaction may be carried out in a suitable solvent such as N,N-dimethylformamide, acetone, acetonitrile or tetrahydrofuran with a suitable base such as $K_2CO_3$, $NaHCO_3$, NaOH or a trialkylamine such as triethylamine. The reaction may be conducted at a temperature between +20° C. and +120° C.

(ii) In the case where $R_2$ is methyl, conversion of compound of formula (XII) to a compound of formula (XLIII) may be carried out by

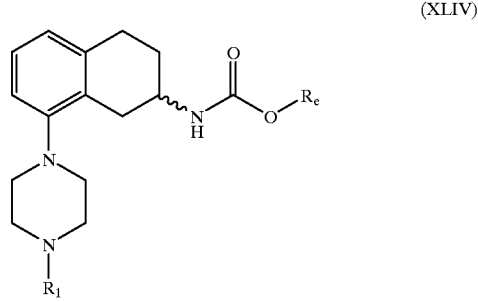

a) conversion of the compound of formula (XII) to a compound of formula (XLIV), where $R_1$ is $C_1$–$C_6$ alkyl or $C_3$–$C_6$ cycloalkyl and $R_e$ is $C_1$–$C_6$ alkyl, with a reagent such as an alkyl chloroformate e.g. ethyl chloroformate in a solvent such as methylene chloride, chloroform, dioxane or diethyl ether with a suitable base such as $K_2CO_3$, $NaHCO_3$, NaOH or a trialkylamine such as triethylamine at a reaction temperature between –20° C. and +60° C. followed by, b) reduction of compound of formula (XLIV) to a compound of formula (XLIII) with an appropriate reductive agent such as lithium aluminum hydride in a suitable solvent e.g. diethyl ether or tetrahydrofiran at a temperature between +20° C. and reflux.

Methods of Preparation of End Products
Method A(i):

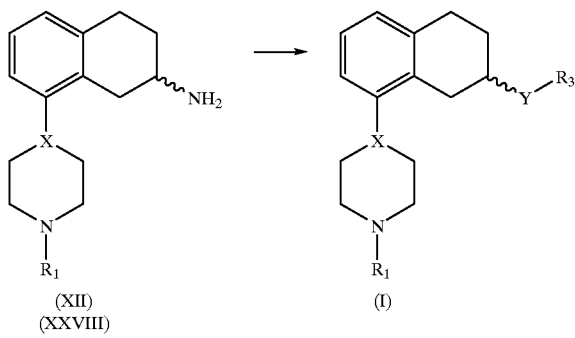

(XII)
(XXVIII)

(I)

Acylation of the compound of formula (XII) wherein X is N or (XXVIIII) wherein X is CH and $R_1$ is $C_1$–$C_6$ alkyl or $C_3$–$C_6$ cycloalkyl, may be carried out with an appropriate activated is carboxylic acid, $R_3$—COL where $R_3$ is as defined in claim 1 and L is a leaving group such as a halogen e.g. chlorine, in a suitable solvent such as methylene chloride or chloroform with a suitable base e.g. trialkylamine such as triethylamine at a temperature between –20° C. and reflux temperature or by using a carboxylic acid, $R_3$—COOH, where $R_3$ is as defined in claim 1 with an activating reagent e.g. N,N'-carbonyldiimidazole or N,N'-dicyclohexylcarbodiimide in a suitable solvent such as N,N-dimethylformamide or tetrahydrofuran and the reaction may be conducted at a temperature between +20° C. and +150° C., resulting in the compound of the formula (I) according to the invention, wherein Y is $NR_2CO$, where $R_2$ is hydrogen, and X is N or CH and $R_1$ is $C_1$–$C_6$ alkyl or $C_3$–$C_6$ cloalkyl, and $R_3$ is as in claim 1.

Method A(ii):

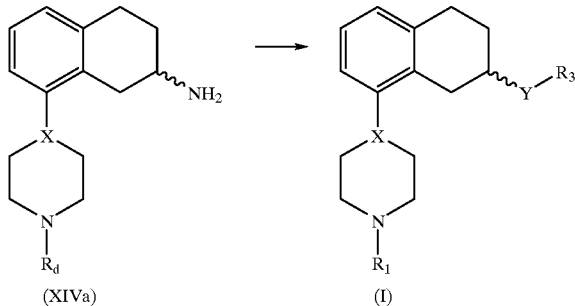

(XIVa)

(I)

Acylation of the compound of formula (XIVa), wherein X is N or CH and $R_d$ is a protecting group, may be carried out with an appropriate activated carboxylic acid $R_3$—COL, where $R_3$ is as defined in claim 1 and L is a leaving group such as a halogen e.g. chlorine, in a suitable solvent such as methylene chloride or chloroform with a suitable base e.g. trialkyl amine such as triethylamine at a temperature between –20° C. and reflux temperature or by using a carboxylic acid, $R_3$—COOH, where $R_3$ is as defined in claim 1 with an activating reagent e.g. N,N'-carbonyldiimidazole or N,N'-dicyclohexylcarbodiimide in a suitable solvent such as N,N-dimethylformamide or tetrahydrofuran at a temperature between +20° C. and +150° C., followed by removal of the protecting group $R_d$ by hydrolyzis in a suitable solvent such as methylene chloride or chloroform with a suitable acid such as trifluoroacetic acid at a temperature between +20° C. and +60° C., resulting in a compound of the formula (I) according to the invention, wherein Y is $NR_2CO$, $R_1$ and $R_2$ are hydrogen, X and $R_3$ are as in claim 1.

Method A(iii)

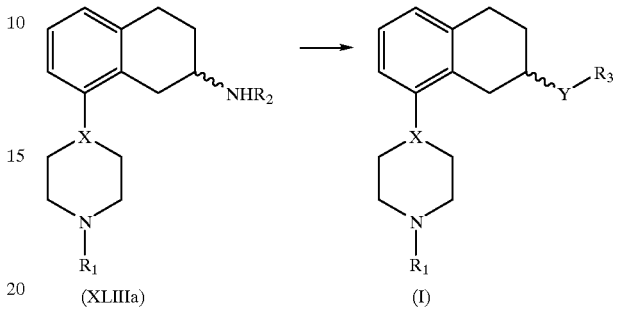

(XLIIIa)

(I)

Acylation of the compound of formula (XLIIIa), wherein X is N or CH, $R_1$ is $C_1$–$C_6$ alkyl or $C_3$–$C_6$ cycloalkyl, $R_2$ is $C_1$–$C_6$ alkyl may be carried out with an appropriate activated carboxylic acid $R_3$—COL, where $R_3$ is as defined in claim 1 and L is a leaving group such as a halogen e.g. chlorine, in a suitable solvent such as methylene chloride or chloroform with a suitable base e.g. trialkyl amine such as triethylamine at a temperature between –20° C. and reflux temperature by using a carboxylic acid, $R_3$—COOH, where $R_3$ is as defined in claim 1 or by using an activating reagent e.g. N,N'-carbonyldiimidazole or N,N'-dicyclohexylcarbodiirnide in a suitable solvent such as N,N-dimethylformamide or tetrahydrofuran at a temperature between +20° C. and +150° C., resulting in a compound of the formula (I) according to the invention, wherein Y is $NR_2CO$, $R_2$ is $C_1$–$C_6$ alkyl, $R_1$ is $C_1$–$C_6$ alkyl or $C_3$–$C_6$ cycloalkyl and X and $R_3$ are as in claim 1.

Method B(i)

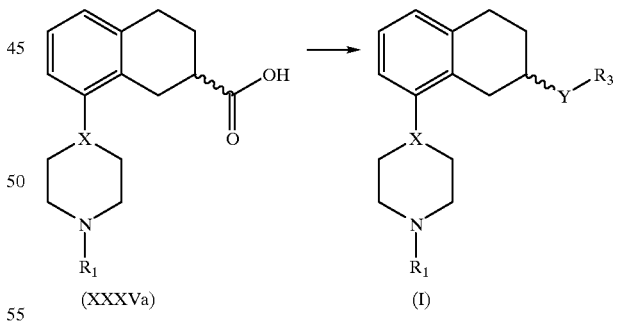

(XXXVa)

(I)

Conversion of a compound of formula (XXXVa), wherein X is N or CH and $R_1$ is $C_1$–$C_6$ alkyl or $C_3$–$C_6$ cycloalkyl, to a compound of formula (I) according to the invention, wherein Y is $CONR_2$, $R_2$ is hydrogen or $C_1$–$C_6$ alkyl, $R_1$ is $C_1$–$C_6$ alkyl or $C_3$–$C_6$ cycloalkyl and X and $R_3$ are as in claim 1, may be carried out by activation of the acid function of a compound of formula (XXXVa) as an acid halide such as an acid chloride or by using an activating reagent such as N,N'-carbonyldiimidazole or N,N-dicyclohexylcarbodiimide in a suitable solvent e.g. methylene chloride, chloroform, toluene, N,N-dimethylformamide, dioxane or tetrahydrofuran followed by the addition of an appropriate amine or aniline $HNR_2R_3$ and the reaction may occur between 0° C. and +120° C.

Method B(ii)

Conversion of a compound of formula (XLIIa), wherein X is N or CH and $R_d$ is a protecting group, to a compound of formula (I) according to the invention, wherein Y is $CONR_2$, $R_2$ is hydrogen or $C_1$–$C_6$ alkyl, $R_1$ is hydrogen and X and $R_3$ are as in claim 1, may be carried out by activation of the acid function of a compound of formula (XLIIa) as an acid halide such as an acid chloride or by using an activating reagent such as N,N'-carbonyldiimidazole or N,N-dicyclohexylcarbodiimide in a suitable solvent e.g. methylene chloride, chloroform, toluene, N,N-dimethylformamide, dioxane or tetrahydrofuran followed by the addition of an appropriate amine or aniline $HNR_2R_3$ and the reaction may occur between 0° C. and +120° C., followed by removal of the protecting group $R_d$ by methods known by a person skilled in the art such as hydrolysis in a suitable solvent such as methylene chloride or chloroform with a suitable acid e.g. trifluoroacetic acid at a temperature between +20° C. and +60° C.

Method C

Conversion of a compound of formula (XIIa), wherein X is N or CH and $R_1$ is $C_1$–$C_6$ alkyl or $C_3$–$C_6$ cycloalkyl, to a compound of formula (I) according to the invention, wherein Y is $NR_2SO_2$, $R_2$ is hydrogen, $R_1$ is $C_1$–$C_6$ alkyl or $C_3$–$C_6$ cycloalkyl and X and $R_3$ are as in claim 1, may be carried out by reaction with an appropriate activated sulfonic acid $R_3SO_2L$, where L is a leaving group such as a halogen e.g. a chlorine in a suitable solvent such as methylene chloride or chloroform with a suitable base e.g. trialkyl amine such as triethylamine and the reaction may be conducted at a temperature between −20° C. and +60° C.

Method D(i)

Reduction of a compound of formula (I), according to the invention wherein X is N or CH, Y is $NR_2CO$, $R_2$ is hydrogen or $C_1$–$C_6$ alkyl, $R_1$ is hydrogen, $C_1$–$C_6$ alkyl or $C_3$–$C_6$ cloalkyl and X and $R_3$ are as in claim 1 (above denoted (Ia)) obtained by method A(i), A(ii) or A(iii) above, to a compound of formula (I) according to the invention where Y is $NR_2CH_2$ and X, $R_1$, $R_2$ and $R_3$ are as defined above (above denoted (Ib)) may be carried out with an appropriate reductive agent such as lithium aluminum hydride in a suitable solvent e.g. diethyl ether or tetrahydrofuran at a temperature between +20° C. and reflux temperature.

Method D(ii)

Reduction of a compound of formula (I) according to the invention wherein X is N or CH, Y is $CONR_2$, $R_2$ is hydrogen or $C_1$–$C_6$ alkyl, $R_1$ is hydrogen, $C_1$–$C_6$ alkyl or $C_3$–$C_6$ cycloalkyl and X and $R_3$ are as in claim 1, (above denoted (Ic)) and obtained by method B(i) or B(ii) above, to a compound of formula (I) according to the invention wherein Y is $CH_2NR_2$, X, $R_1$, $R_2$ and $R_3$ are as defined in claim 1 (above denoted (Id)) may be carried out with an appropriate reductive agent such as lithium aluminum hydride in a suitable solvent e.g. diethyl ether or tetrahydrofuran at a temperature between +20° C. and reflux temperature.

Method E

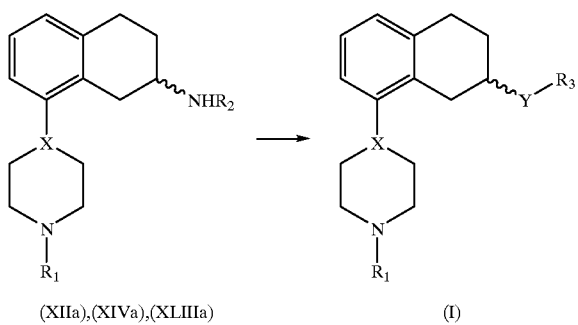

(XIIa),(XIVa),(XLIIIa)     (I)

Alkylation of compound of formula (XIIa), wherein X is N or CH, $R_1$ is $C_1$–$C_6$ alkyl or $C_3$–$C_6$ cycloalkyl, $R_2$ is hydrogen, or a compound of formula (XIVa), wherein X is N or CH, $R_1$ is $R_d$, where $R_d$ is a protecting group, and $R_2$ is hydrogen, or a compound of formula (XLIIIa), wherein X is N or CH, $R_1$ is $C_1$–$C_6$ alkyl or $C_3$–$C_6$ cycloalkyl and $R_2$ is $C_1$–$C_6$ alkyl to a compound of formula (I), according to the invention, wherein Y is $NR_2CH_2$, X, $R_1$ and $R_2$ are as above, and $R_3$ is as in claim 1 may be carried out with a suitable alkylation reagent such as $R_3CH_2$—L, where L is a suitable leaving group e.g. a halogen such as chlorine, bromine or iodine or an alkyl- or arylsulfonyloxy group such as p-toluene sulfonyloxy group. The reaction may be carried out in a suitable solvent such as N,N-dimethylformamide, acetone, acetonitrile or tetrahydrofuran with a suitable, base such as $K_2CO_3$, $NaHCO_3$, NaOH or a trialkylamine such as triethylamine. The reaction may be conducted at a temperature between +20° C. and +120° C. In the case when $R_1$ is $R_d$, the alkylation is followed by removal of the protecting group $R_d$ by hydrolysis in a suitable solvent such as methylene chloride or chloroform with a suitable acid such as trifluoroacetic acid at a temperature between +20° C. and +60° C.

Method F

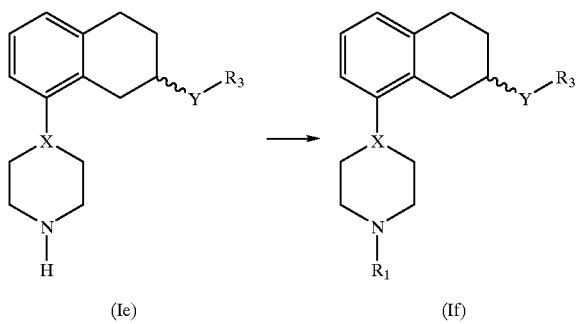

(Ie)     (If)

Alkylation of a compound of formula (Ie), according to the invention wherein X is N or CH, Y is $NR_2CO$, $R_2$ is hydrogen or $C_1$–$C_6$ alkyl and $R_3$ is as in claim 1, and obtained by method A(ii), to a compound of formula (If) according to the invention wherein Y is $NR_2CO$, $R_2$ is hydrogen or $C_1$–$C_6$ alkyl, $R_1$ is $C_1$–$C_6$ alkyl and X and $R_3$ are as in claim 1 may be carried out with a suitable alkylation reagent such as $R_1$—L where L is a suitable leaving group e.g. a halogen such as chlorine, bromine or iodine or an alkyl- or arylsulfonyloxy group such as p-toluenesulfonyloxy group and $R_1$ is $C_1$–$C_6$ alkyl. The reaction may be carried out in a suitable solvent such as N,N-dimethylformamide, acetone, acetonitrile or tetrahydrofuran with a suitable base such as $K_2CO_3$, $NaHCO_3$, NaOH or a trialkylamine such as triethylamine. The reaction may be conducted at a temperature between +20° C. and +120° C.

Intermediates

The present invention also refers to new intermediates, namely intermediates of formula

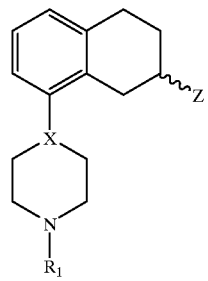

wherein
$Z=NH_2$ or COOH,
X=CH or N, and
$R_1$=H, $C_1$–$C_6$ alkyl or $C_3$–$C_6$ cycloalkyl.

The invention is illustrated by but not restricted to the following working examples.

Except where otherwise indicated, the necessary starting materials for all Preparations and Examples were purchased commercially.

WORKING EXAMPLES

Example 1

(R)-2-N,N-Dibenzylamino-8-methoxy-1,2,3,4-tetrahydronaphthalene

To a solution of (R)-8-methoxy-2-amino-1,2,3,4-tetrahydronaphthalene hydrochloride (24 g, 0.11 mol) in acetonitrile (600 mL) were added potassium carbonate (53 g, 0.39 mol), potassium iodide (catalytic amount) and benzyl bromide (34 mL, 0.28 mol). The reaction mixture was stirred at reflux for a period of 35 h.

After the precipitate was filtered off and the acetonitrile removed in vacuo, the residue was partitioned between diethyl ether and water. The organic phase was separated, dried ($Na_2SO_4$) and evaporated in vacuo to give a crude product which was purified on a silica gel column using hexane/ethyl acetate, (3:1) as the eluent. Yield: 36 g (91%) of the title compound as a white solid: mp 105–107° C.; $[\alpha]^{21}_D$ +124° (c 1.0, chloroform); EIMS (70 eV) m/z (relative intensity) 357 (100, M$^+$).

Example 2

(S)-2-N,N-Dibenzylamino-8-methoxy-1,2,3,4-tetrahydronaphthalene

The title compound was synthesized according to the procedure of Example 1 using the (S)-form: mp 106–107° C.; $[\alpha]^{21}_D$ −118° (c 1.0, chloroform); EIMS (70 eV) m/z (relative intensity) 357 (100, M$^+$).

Example 3

(R)-7-N,N-Dibenzylamino-5,6,7,8-tetrahydro-1-naphthol (R)-2-N,N-Dibenzylamino-8-methoxy-1,2,3,4-tetrahydronaphthalene (43 g, 0.12 mol) was dissolved in diethyl ether (800 mL) and an excess of an ethereal HCl solution was added dropwise. The precipitate was filtered and dried in vacuo to give a white solid. This crude product (42 g, 0.11 mol) was dissolved in anhydrous methylene chloride (1 L) and cooled to −60° C. To the solution was boron tribromide (16 mL, 0.15 mol), dissolved in anhydrous methylene chloride (100 mL), added dropwise. The reaction temperature was allowed to reach −5° C. and was kept there overnight.

To the ice-cooled solution was a 2 M aqueous ammonium hydroxide solution added dropwise and the mixture was extracted, twice, with methylene chloride. The combined organic phases were dried ($Na_2SO_4$), filtered and the solvent removed in vacuo to give a crude residue. Chromatography on silica (eluent: methylene chloride) gave 34 g (93% yield) of the title compound as a viscous clear oil: $[\alpha]^{21}_D$ +118° (c 1.5, chloroform); EIMS (70 eV) m/z (relative intensity) 343 (53, M$^+$).

Example 4

(S)-7-N,N-Dibenzylamino-5,6,7,8-tetrahydro-1-naphthol

The title compound was synthesized according to the procedure of Example 3 using the (S)-form: $[\alpha]^{21}_D$ −116° (c 1.0, chloroform), EIMS (70 eV) m/z (relative intensity) 343 (100, M$^+$).

Example 5

(R)-2-(7-N,N-Dibenzylamino-5,6,7,8-tetrahydro-1-naphthyloxy)-2-methylpropanamide (R)-2-N,N-Dibenzylamino-5,6,7,8-tetrahydro-1-naphthol (10 g, 29 mmol) was stirred in anhydrous dioxane (150 mL) with sodium hydride (80% in oil, 0.96 g, 32 mmol) for 1 h. 2-Bromo-2-methylpropanaride (4.8 g, 29 mmol; described in: Coutts, I. G. C.; Southcott, M. R. *J. Chem. Soc. Perkin Trans.* 1 1990, 767–770) was added and the reaction mixture was heated at 100° C. for 2.5 h. After cooling, the precipitated sodium bromide was filtered off, the filtrate evaporated in vacuo and the residue was partitioned between water and methylene chloride. The organic phase was separated, dried ($Na_2SO_4$), filtered and evaporated to give a crude product which was purified on a silica gel column using methylene chloride as the eluent. Yield: 9.6 g (76%) of the title compound as white crystals: mp 125–126° C.; $[\alpha]^{21}_D$ +98° (c 1.1, chloroform); EIMS (70 eV) m/z (relative intensity) 428 (13, M$^+$).

Example 6

(S)-2-(7-N,N-Dibenzylamino-5,6,7,8-tetrahydro-1-naphthyloxy)2-methylpropanamide

The title compound was synthesized according to the procedure of Example 5 using the (S)-form: mp 124–125° C.; $[\alpha]^{21}_D$ −100° (c 0.52, chloroform); EIMS (70 eV) m/z (relative intensity) 428 (4, M$^+$).

Example 7

(R)-N-(7-N,N-Dibenzylamino-5,6,7,8-tetrahydro-1-naphthyl)-2-hydroxy-2-methylpropanamide To a solution of (R)-2-(7-N,N-dibenzylamino-5,6,7,8-tetrahydro-1-naphthyloxy)-2-methylpropanamide (9.1 g, 21 mmol) in anhydrous 1,3-dimethyl-3,4,5,6-tetrahydro-2(1H)-pyrimidone (10 mL) and dry N,N-dimethylformamide (100 mL) was added sodium hydride (80% in oil, 1.4 g, 47 mmol) and the reaction was heated at 130° C. for 8 h. The solution was poured into a mixture of ice and water and extracted three times with ethyl acetate. The combined organic phases were dried ($Na_2SO_4$), filtered and evaporated in vacuo. Chromatography on silica (eluent: chloroform/ethanol saturated with $NH_3$; 100:0.5) gave 7.6 g (84% yield) as white crystals: mp 134–135° C.; $[\alpha]^{21}_D$ +130° (c 1.1, chloroform); EIMS (70 eV) m/z (relative intesity) 428 (1, M$^+$).

Example 8

(S)-N-(7-N,N-Dibenzylamino-5,6,7,8-tetrahydro-1-naphthyl)-2-hydroxy-2-methylpropanamide The title compound was synthesized according to the procedure of Example 7 using the (S)-form: mp 132–134° C.; $[\alpha]^{21}_D$ −132° (c 0.53, chloroform); EIMS (70 eV) m/z (relative intesity) 428 (<1, M$^+$).

Example 9

(R)-2-N,N-Dibenzylamino-8-amino-1,2,3,4-tetrahydronaphthalene (R)-N-(7-N,N-Dibenzylamino-5,6,7,8-tetrahydro-1-naphthyl)-2-hydroxy-2-methylpropionarnide (7.4 g, 17 mmol) was dissolved in a mixture of ethanol (200 mL) and a 20% HCl aqueous solution (300 mL) and heated to reflux for 8 h. The ethanol was evaporated in vacuo and the remaining solution was washed twice with diethyl ether and cooled on ice-bath. After alkalization with a 45% aqueous solution of sodium hydroxide the mixture was extracted with methylene chloride. The combined organic phases were dried ($Na_2SO_4$), filtered and evaporated in vacuo. Purification on a silica gel column using chloroform as the eluent gave 3.8 g (76% yield) of the title compound as a light-brown oil: $[\alpha]^{21}_D$ +124° (c 0.9, chloroform); EIMS (70 eV) m/z (relative intensity) 342 (92, M$^+$).

Example 10

(S)-2-N,N-Dibenzylamino-8-amino-1,2,3,4-tetrahydronaphthalene

The title compound was synthesized according to the procedure of Example 9 using the (S)-form: $[\alpha]^{21}_D$ −127° (c 0.53, chloroform); EIMS (70 eV) m/z (relative intensity) 342 (89, M$^+$).

Example 11

(R)-1-(7-N,N-Dibenzylamino-5,6,7,8-tetrahydro-1-naphthyl)-4-N-methylpiperazine-2,6-dione 1,1'-Carbonyldiimidazole (6.0 g, 37 mmol) was added to a stirred suspension of methyliminodiacetic acid (2.7 g, 18 mmol) in anhydrous tetrahydrofaran (250 mL). The reaction mixture was heated at reflux for 1.5 h. (R)-2-N,N-Dibenzylamino-8-amino-1,2,3,4-tetrahydronaphthalene (5.7 g, 17 mmol) was then added and stirring at reflux was continued for 17 h. An additional amount of 1,1'-carbonyldiimidazole (2.9 g, 18 mmol) was added and heating at reflux was continued for another 17 h. The solvent was evaporated in vacuo and the crude product was purified on a silica gel column using chloroform/ethanol saturated with $NH_3$ (100:0.5) as the eluent. Yield: 6.6 g (87%) of the title compound as an oil: $[\alpha]^{21}_D$ +90° (c 0.52, chloroform); EIMS (70 eV) m/z (relative intensity) 453 (8, M$^+$).

Example 12

(R)-2-N,N-Dibenzylamino-8-(4-methylpiperazin-1-yl)-1,2,3,4-tetrahydronaphthalene (R)-1-(7-N,N-Dibenzylaamino-5,6,7,8-tetrahydro-1-naphthyl)-4-methylpiperazine-2,6-dione (1.4 g, 3.1 mmol)

was added to a suspension of lithium aluminum hydride (0.57 g, 15 mmol) in anhydrous diethyl ether (70 mL). The reaction mixture was heated at reflux for 7 h. The reaction was quenched by the addition of water (0.60 mL), 15% aqueous sodium hydroxide (0.60 mL) and again water (1.8 mL). The mixture was filtered, dried ($Na_2SO_4$) and evaporated in vacuo. Purification on a silica gel column using chloroform/ethanol saturated with $NH_3$ (100:2) as the eluent gave 1.0 g (79% yield) of the title compound as a viscous oil: $[\alpha]^{21}_D$ +53° (c 0.5, chloroform); EIMS (70 eV) m/z (relative intensity) 425 (2, $M^+$).

Example 13

(S)-2-N,N-Dibenzylamino-8-(4-methylpiperazin-1-yl)-1,2,3,4-tetrahydronaphthalene (S)-2-N,N-Dibenzylamino-8-amino-1,2,3,4-tetrahydronaphthalene (3.0 g, 8.8 mmol), potassium iodide (73 mg, 0.4 mmol) and N-methylbis(2-chloroethyl)amine hydrochloride (3.4 g, 17.6 mmol) were mixed with acetonitrile (100 mL) and water (17 mL) under nitrogen atmosphere. The mixture was refluxed for 7 h. The temperature of the reaction mixture was allowed to reach room temperature before 2 M sodium hydroxide (20 mL) was added. The solvent was removed in vacuo until ca 70 mL remained. The residue was extracted with ethyl acetate twice. The organic layers were combined and dried ($Na_2SO_4$). Removal of solvent in vacuo gave a crude product which was purified on a silica gel column using methylene chloride/ethanol/concentrated ammonium hydroxide (90:9.5:0.5) as the eluent. Yield: 2 g (53%) of the title compound as an oil: $[\alpha]^{21}_D$ −60° (c 1, MeOH); EIMS (70 eV) m/z (relative intensity) 425 (0.2, $M^+$).

Example 14

(R)-2-Amino-8-(4-methylpiperazin-1-yl)-1,2,3,4-tetrahydronaphthalene

To a solution of (R)-2-N,N-dibenzylamino-8-(4-methylpiperazin-1-yl)-1,2,3,4-tetrahydronaphthalene (4.0 g, 9.4 mmol) in methanol (250 mL) were added ammonium formate (14 g, 56 mmol) and palladium (10%) on activated carbon (1.4 g). The mixture was refluxed for 3 h and the palladium was then filtered off. The solvent was evaporated in vacuo and the residue was partitioned between methylene chloride and a 2 M ammonium hydroxide solution. The organic phase was separated, dried ($Na_2SO_4$), filtered and evaporated in vacuo to give a crude product which was purified on a silica gel column using chloroform/methanol/concentrated ammonium hydroxide (90:9:0.5) as the eluent. Yield: 1.9 g (83%) as an oil: $[\alpha]^{21}_D$ −2.7° (c 1.0, chloroform); EIMS (70 eV) m/z (relative intensity) 245 (5, $M^+$).
Alternative Method
(R)-2-N,N-Dibenzylamino-8-(4-methylpiperazin-1-yl)-1,2,3,4-tetrahydronaphthalene (1.0 g, 2.4 mmol) was dissolved in glacial acetic acid (70 mL) and palladium (10%) on activated carbon (100 mg) was added and the mixture was hydrogenated at 50–55° C. The catalyst was filtered off and the solvent was evaporated in vacuo. The residue was dissolved in water (20 mL) and cooled on ice-bath. After alkalization with a 2 M aqueous sodium hydroxide solution the mixture was extracted, twice, with methylene chloride. The phases were separated and the organic phase was dried ($Na_2SO_4$), filtered and evaporated in vactio. The crude product was purified on a silica gel column using chloroformn/methano/concentrated ammonium hydroxide (90:9:0.5) as the eluent to give 330 mg (57% yield) of the title compound.

Example 15

(S)-2-Amino-8-(4-methylpiperazin-1-yl)-1,2,3,4-tetrahydronaphthalene (S)-2-N,N-Dibenzylamino-8-(4-methylpiperazin-1-yl)-1,2,3,4-tetrahydronaphthalene (0.8 g, 1.9 mmol), palladium on activated carbon (10%, 400 mg), ammonium formate (1.8 g, 28 mmol), methanol (25 mL) and water (10 mL) were mixed under nitrogen atmosphere. The mixture was refluxed for 2 h. The catalyst was filtered off and ethyl acetate and sodium hydroxide (2 M) were added. The layers were separated and the aqueous phase was extracted three times with ethyl acetate. The organic layers were combined and dried ($Na_2SO_4$). The solvent was removed in vacuo to give 0.35 g of the title compound as an oil (75% yield): $[\alpha]^{21}_D$ −22° (c 1, MeOH) EIMS (70 eV) m/z (relative intensity) 245 (5, $M^+$).

Example 16

(R)-2-N,N-Dibenzylamino-8-(piperazin-1-yl)-1,2,3,4-tetrahydronaphthalene (R)-2-N,N-Dibenzylamino-8-amino-1,2,3,4-tetrahydronaphthalene (9.8 g, 39 mmol) and bis-(2-chloroethyl)amine hydrochloride (5.5 g, 32 mmol) was dissolved in n-butanol (80 mL). The reaction mixture was stirred at 100° C. and after 65 h the mixture was filtered and the solvent evaporated in vacuo. Purification on a silica gel column using chloroformn/methanol/concentrated ammonium hydroxide (95:5:0.5) as the eluent gave 6.0 g (51% yield) of the title compound as a viscous oil: $[\alpha]^{21}_D$ +72° (c 1.0, chloroform), EIMS (70 eV) m/z (relative intensity) 411 (2, $M^+$).

Example 17

(R)-2-Amino-8-(piperazin-1-yl)-1,2,3,4-tetrahydronaphthalene

To a solution of (R)-2-N,N-dibenzylamino-8-(piperazin-1-yl)-1,2,3,4-tetrahydronaphthalene (5.5 g, 13 mmol) in methanol (400 mL) were added ammonium formate (20 g, 0.32 mol) and palladium (10%) on activated carbon (1.9 g). The mixture was refluxed for 1 h and the palladium was then filtered off. The solvent was evaporated in vacuo and the residue was partitioned between methylene chloride and a 2 M ammonium hydroxide solution. The organic phase was separated, dried ($Na_2SO_4$), filtered and evaporated in vacuo to give a crude product which was purified on a silica gel column using chloroform/ethanol/concentrated ammonium hydroxide (80:20:2.5) as the eluent. Yield: 2.4 g (76%) of the title compound as an oil: $[\alpha]^{21}_D$ +9.9° (c 1.0, chloroform); EIMS (70 eV) m/z (relative intensity) 231 (24, $M^+$).

Example 18 tert-Butyl (R)-4-(7-Amino-5,6,7,8-tetrahydro-1-naphthyl)piperazine-1-carboxylate To an ice-cooled solution of (R)-2-amino-8-(piperazin-1-yl)-1,2,3,4-tetrahydronaphthalene (1.5 g, 6.5 mmol) and triethylamine (1.0 mL, 7.5 mmol) in methylene chloride (400 mL) was di-tert-butyl dicarbonate (1.5 mL, 6.5 mmol) in methylene chloride (50 mL) added dropwise. After the addition the reaction was allowed to stir at ambient tem-

Example 19

(R)-N-[8-(4-Methylpiperazin-1-yl)-1,2,3,4-tetrahydro-2-naphthyl]acetamide

To an ice-cooled solution of (R)-2-amino-8-(4-methylpiperazin-1-yl)-1,2,3,4-tetrahydronaphthalene (100 mg, 0.41 mmol) and triethylamine (110 µL, 0.82 mmol) in methylene chloride (25 mL) was added acetyl chloride (31 µL, 0.43 mmol) in methylene chloride (10 mL). After the addition the reaction was allowed to reach room temperature and then washed with water. The phases were separated, the combined organic phases were dried ($Na_2SO_4$), filtered and evaporated in vacuo to give a crude product which was purified on a silica get column using chloroform/methanol/concentrated ammonium hydroxide (95:4:0.5) as the eluent. Yield: 110 mg (90%) of the title compound as an oil. Crystallization from ethyl acetate/hexane gave 52 mg (44% yield) of white crystals: mp 152–154° C.; $[\alpha]^{21}_D$ +66° (c 0.13, chloroform); EIMS (70 eV) m/z (relative intensity) 287 (9, M$^+$).

Example 20

(R)-N-[8-(Piperazin-1-yl)-1,2,3,4-tetrahydro-2-naphthyl]acetamide

To an ice-cooled solution of tert-butyl (R)-4-(7-amino-5,6,7,8-tetrahydro-1-naphthyl)piperazine-1-carboxylate (120 mg, 0.36 mmol) and triethylamine (100 µL, 0.72 mmol) in methylene chloride (30 mL) acetyl chloride (26 µL, 0.36 mmol) in methylene chloride (5 mL) was added dropwise. After the addition the reaction was allowed to stir at ambient temperature for 20 min and was then washed with water. The methylene chloride phase was dried ($Na_2SO_4$), filtered and evaporated in vacuo and the crude product was purified on a silica gel column using chloroform/methanol/concentrated ammonium hydroxide (95:5:0.5) as the eluent to afford 130 mg (92% yield) of a viscous oil: EIMS (70 eV) m/z (relative intensity) 373 (40, M$^+$). This oil was dissolved in methylene chloride (25 mL), without further characterization and trifluoroacetic acid (1.0 mL) was added. The reaction was stirred for 7 h at ambient temperature, water was added and the mixture was cooled on an ice-bath. After alkalization with 2 M aqueous sodium hydroxide solution the mixture was extracted, twice, with methylene chloride. The combined organic phases were dried ($Na_2SO_4$), filtered and evaporated in vacuo. Purification on a silica gel column using chloroform/methanol/concentrated ammonium hydroxide (95:5:0.5) as the eluent gave 60 mg (61% yield from tert-butyl (R)-4-(7-amino-5,6,7,8-tetrahydro-1-naphthyl)piperazine-1-carboxylate) of the title compound as a viscous oil: $[\alpha]^{21}_D$ +31° (c 0.50, chloroform); EIMS (70 eV) m/z (relative intensity) 273 (100, M$^+$).

Example 21

(R)-N-[8-(4-Ethylpiperazin-1-yl)-1,2,3,4-tetrahydro-2-naphthyl]acetamide

To a mixture of (R)-N-[8-(piperazin-1-yl)-1,2,3,4-tetrahydro-2-naphthyl]acetamide (100 mg, 0.37 mmol), potassium carbonate (76 mg, 0.54 mmol) and potassium iodide (15 mg, 0.10 mmol) in acetone (20 mL) was added ethyl bromide (56 µL, 0.74 mmol) added and the reaction mixture was vigorously stirred over night. The reaction was filtered and the solvent was evaporated in vacuo. The residue was purified on a silica gel column using chloroform/methanol/concentrated ammonium hydroxide (95:5:0.5) as the eluent. This gave 87 mg (78% yield) of the title compound as an oil which was crystallized from ethyl acetate/hexane. Yield: 55 mg (50%) as white crystals: mp 142–143° C.; $[\alpha]^{21}_D$ +27° (c 0.50, chloroform); EIMS (70 eV) m/z (relative intensity) 301 (100, M$^+$).

Example 22

(R)-2-N,N-Dibenzylamino-8-(4-propylpiperazin-1-yl)-1,2,3,4-tetrahydronaphthalene To a mixture of (R)-2-N,N-dibenzylamino-8-(piperazin-1-yl)-1,2,3,4-tetrahydronaphthalene (200 mg, 0.49 mmol) and potassium carbonate (100 mg, 0.74 mmol) in acetone (15 mL) was added propyl iodide (72 µL, 0.74 mmol) and the reaction mixture was vigorously stirred overnight at 50° C. The reaction was filtered and the solvent was evaporated in vacuo. The residue was purified on a silica gel column using chloroform/ethanol saturated with $NH_3$ (100:1) as the eluent. This gave 180 mg (81% yield) of the title compound as an oil: EIMS (70 eV) m/z (relative intensity) 453 (5, M$^+$).

Example 23

(R)-2-Amino-8-(4-propylpiperazin-1-yl)-1,2,3,4-tetrahydronaphthalene

To a solution of (R)-2-N,N-dibenzylamino-8-(4-propylpiperazin-1-yl)-1,2,3,4-tetrahydronaphthalene (180 mg, 0.4 mmol) in methanol (15 mL) were added ammonium formate (0.60 g, 2.4 mmol) and palladium (10%) on activated carbon (60 mg). The mixture was refluxed for 2 h and the palladium was then filtered off. The solvent was evaporated in vacuo and the residue was partitioned between methylene chloride and a 2 M ammonium hydroxide solution. The organic phase was separated, dried ($Na_2SO_4$), filtered and evaporated in vacuo to give the title compound as an oil. Yield: 85 mg (78%): EIMS (70 eV) m/z (relative intensity) 273 (4, M$^+$).

Example 24

(R)-N-[8-(4-Propylpiperazin-1-yl)-1,2,3,4-tetrahydro-2-naphthyl]acetamide

To an ice-cooled solution of (R)-2-amino-8-(4-propylpiperazin-1-yl)-1,2,3,4-tetrahydronaphthalene (85 mg, 0.31 mmol) and triethylamine (38 µL, 0.37 mmol) in methylene chloride (15 mL) was added acetyl chloride (23 µL, 0.31 mmol) in methylene chloride (5 mL) dropwise. After the addition the reaction was allowed to stir at ambient temperature for 15 min and was then washed with water. The methylene chloride phase was dried ($Na_2SO_4$), filtered and evaporated in vacuo. The residue was purified on a silica gel column using chloroform/ethanol saturated with ($NH_3$) (100:3) as the eluent. This gave 91 mg (93% yield) of the title compound as an oil which was crystallized from ethyl acetate/hexane. Yield: 61 mg (62%) as white crystals: mp 139–140° C.; $[\alpha]^{21}_D$ +26° (c 0.50, chloroform); EIMS (70 eV) m/z (relative intensity) 315 (78, M$^+$).

Example 25

(R)-2-N,N-Dibenzylamino-8-(4-butylpiperazin-1-yl)-1,2,3,4-tetrahydronaphthalene

To a mixture of (R)-2-N,N-dibenzylamino-8-(piperazin-1-yl)-1,2,3,4-tetrahydronaphthalene (300 mg, 0.73 mmol), potassium carbonate (150 mg, 1.1 mmol) and potassium iodide (catalytic amount) in N,N-dimethylformamide (25 mL) was added butyl bromide (130 mg, 0.95 mmol) and the reaction mixture was vigorously stirred overnight at 60° C. The reaction was filtered and the solvent was evaporated in vacuo. The residue was purified on a silica gel column using chloroform/ethanol saturated with $NH_3$ (100:1) as the eluent. This gave 300 mg (86% yield) of the title compound as an oil: $[\alpha]^{21}_D$ +68° (c 0.72, chloroform); EIMS (70 eV) m/z (relative intensity) 467 (5, M$^+$).

Example 26

(R)-2-Amino-8-(4-butylpiperazin-1-yl)-1,2,3,4-tetrahydronaphthalene

To a solution of (R)-2-N,N-dibenzylamino-8-(4-butylpiperazin-1-yl)-1,2,3,4-tetrahydronaphthalene (300 mg, 0.63 mmol) in methanol (20 mL) were added ammonium formate (0.95 g, 3.8 mmol) and palladium (10%) on activated carbon (90 mg). The mixture was refluxed for 2 h and the palladium was then filtered off. The solvent was evaporated in vacuo and the residue was partitioned between methylene chloride and a 2 M ammonium hydroxide solution. The organic phase was separated, dried ($Na_2SO_4$), filtered and evaporated in vacuo to give the title compound as an oil. Yield: 100 mg (56%): $[\alpha]^{21}_D$ −4.6° (c 1.3, chloroform); EIMS (70 eV) m/z (relative intensity) 287 (10, M$^+$).

Example 27

(R)-N-[8-(4-Butylpiperazin-1-yl)-1,2,3,4-tetrahydro-2-naphthyl]acetamide

To an ice-cooled solution of (R)-2-amino-8-(4-butylpiperazin-1-yl)-1,2,3,4-tetrahydronaphthalene (100 mg, 0.35 mmol) and triethylamine (53 μL, 0.53 mmol) in methylene chloride (25 mL) was added dropwise acetyl chloride (25 μL, 0.35 mmol) in methylene chloride (10 mL). After the addition the reaction was allowed to stir at ambient temperature for 15 min and was then washed with water. The methylene chloride phase was dried ($Na_2SO_4$), filtered and evaporated in vacuo. The residue was purified on a silica gel column using chloroform/ethanol saturated with $NH_3$ (100:3) as the eluent. This gave, after crystalization from diethyl ether, 100 mg (89% yield) of the title compound as white crystals: mp 118–120° C.; $[\alpha]^{21}_D$ +25° (c 0.54, chloroform); EIMS (70 eV) m/z (relative intensity) 329 (41, M$^+$).

Example 28

(R)-2-N,N-Dibenzylamino-8-(4-pentylpiperazin-1-yl)-1,2,3,4-tetrahydronaphthalene To a mixture of (R)-2-N,N-dibenzylamino-8-(piperazin-1-yl)-1,2,3,4-tetrahydronaphthalene (500 mg, 1.2 mmol), potassium carbonate (250 mg, 1.8 mmol) and potassium iodide (catalytic amount) in N,N-dimethylformamide (30 mL) was added pentyl bromide (220 mg, 1.5 mmol) and the reaction mixture was vigorously stirred overnight at 60° C. The reaction was filtered and the solvent was evaporated in vacuo. The residue was purified on a silica gel column using chloroform/ethanol saturated with $NH_3$ (100:1) as the eluent. This gave 460 mg (79% yield) of the title compound as an oil: $[\alpha]^{21}_D$ +55.4° (c 1.1, chloroform); EIMS (70 eV) m/z (relative intensity) 481 (3, M$^+$).

Example 29

(R)-2-Amino-8-(4-pentylpiperazin-1-yl)-1,2,3,4-tetrahydronaphthalene

To a solution of (R)-2-N,N-dibenzylamino-8-(4-pentylpiperazin-1-yl)-1,2,3,4-tetrahydronaphthalene (450 mg, 0.94 mmol) in methanol (20 mL) were added ammonium formate (1.4 g, 5.6 mmol) and palladium (10%) on activated carbon (0.14 g). The mixture was refluxed for 2 h and the palladium was then filtered off. The solvent was evaporated in vacuo and the residue was partitioned between methylene chloride and a 2 M ammonium hydroxide solution. The organic phase was separated, dried ($Na_2SO_4$), filtered and evaporated in vacuo to give the title compound as an oil. Yield: 180 mg (64%): $[\alpha]^{21}_D$ −3.7° (c 0.57, chloroform); EIMS (70 eV) m/z (relative intensity) 301 (47, M$^+$).

Example 30

(R)-N-[8-(4-Pentylpiperazin-1-yl)-1,2,3,4-tetrahydro-2-naphthyl]acetamide

To an ice-cooled solution of (R)-2-amino-8-(4-pentylpiperazin-1-yl)-1,2,3,4-tetrahydronaphthalene (170 mg, 0.57 mmol) and triethylamine (86 μL, 0.86 mmol) in methylene chloride (30 mL) was added dropwise acetyl chloride (41 μL, 0.57 mmol) in methylene chloride (10 mL). After the addition the reaction was allowed to stir at ambient temperature for 15 min and was then washed with water. The methylene chloride phase was dried ($Na_2SO_4$), filtered and evaporated in vacuo. The residue crystallized from diethyl ether/hexane. This gave 120 mg (62% yield) of the title compound as white crystals: mp 119–120° C. $[\alpha]^{21}_D$ +25° (c 0.97, chloroform); EIMS (70 eV) m/z (relative intensity) 343 (49, M$^+$).

Example 31

(R)-2-N,N-Dibenzylamino-8-(4-hexylpiperazin-1-yl)-1,2,3,4-tetrahydronaphthalene

To a mixture of (R)-2-N,N-dibenzylarino-8-(piperazin-1-yl)-1,2,3,4-tetrahydronaphthalene (440 mg, 1.1 mmol), potassium carbonate (220 mg, 1.8 mmol) and potassium iodide (catalytic amount) in N,N-dimethylformamide (25 mL) was added hexyl bromide (320 μg, 2.3 mmol) and the reaction mixture was vigorously stirred overnight at 60° C. The reaction was filtered and the solvent was evaporated in vacuo. The residue was purified on a silica gel column using chloroform/ethanol saturated with $NH_3$ (100:1) as the eluent. This gave 460 mg (79% yield) of the title compound as an oil: $[\alpha]^{21}_D$ +37° (c 1.2, chloroform); EIMS (70 eV) m/z (relative intensity) 495 (3, M$^+$)

Example 32

(R)-2-Amino-8-(4-hexylpiperazin-1-yl)-1,2,3,4-tetrahydronaphthalene

To a solution of (R)-2-N,N-dibenzylamino-8-(4-hexylpiperazin-1-yl)-1,2,3,4-tetrahydronaphthalene (300 mg, 0.60 mmol) in methanol (30 mL) were added ammonium formate (0.90 g, 3.6 mmol) and palladium (10%) on activated carbon (90 mg). The mixture was refluxed for 2 h and the palladium was then filtered off. The solvent was evaporated in vacuo and the residue was partitioned between methylene chloride and a 2 M ammonium. hydroxide solution. The organic phase was separated, dried ($Na_2SO_4$), filtered and evaporated in vacuo to give the title compound as an oil. Yield: 130 mg (68%): $[\alpha]^{21}_D$ −2.3° (c 1.0, chloroform); EIMS (70 eV) m/z (relative intensity) 315 (91, M$^+$).

Example 33

(R)-N-[8-(4-Hexylpiperazin-1-yl)-1,2,3,4-tetrahydro-2-naphthyl]acetamide

To an ice-cooled solution of (R)-2-amino-8-(4-hexylpiperazin-1-yl)-1,2,3,4-tetrahydronaphthalene (97 mg, 0.31 mmol) and triethylamine (51 μL, 0.37 mmol) in methylene chloride (15 mL) was added dropwise acetyl chloride (23 μL, 0.32 mmol) in methylene chloride (5 mL). After the addition the reaction was allowed to stir at ambient temperature for 15 min and was then washed with water. The methylene chloride phase was dried ($Na_2SO_4$), filtered and evaporated in vacuo. The residue was purified on a silica gel column using chloroform/ethanol saturated with $NH_3$ (100:3) as the eluent. This gave after crystallization from diethyl ether/hexane 92 mg (83% yield) of the title compound as white crystals: mp 117–118° C.; $[\alpha]^{21}_D$ +19° (c 1.0, chloroform); EIMS (70 eV) m/z (relative intensity) 357 (43, M$^+$).

Example 34

(R)-N-[8-(4-Methylpiperazin-1-yl)-1,2,3,4-tetrahydro-2-naphthyl]trifluoroacetamide To an ice-cooled solution of (R)-2-amino-8-(4-methylpiperazin-1-yl)-1,2,3,4-tetrahydronaphthalene (120 mg, 0.49 mmol), pyridine (100 μL, 1.2 mmol) and 4-dimethylaminopyridine (20 mg, 0.16 mmol) in methylene chloride (10 mL) was added dropwise trifluoroacetic anhydride (72 μL, 0.51 mmol). After the addition the reaction was allowed to stir at ambient temperature for 1 h and was then washed with water. The methylene chloride phase was dried ($Na_2SO_4$), filtered and evaporated in vacuo. The residue was purified on a silica gel column using ethyl acetate/methanol/concentrated ammonium hydroxide (96:4:0.5) as the eluent. This gave after crystallization from diethyl ether/hexane 41 mg (24% yield) of the title compound as white crystals: mp 158–159° C.; $[\alpha]^{21}_D$ +39° (c 0.25, chloroform); EIMS (70 eV) m/z (relative intensity) 341 (82, M$^{30}$).

Example 35

(R)-N-[8-(4-methylpiperazin-1-yl)-1,2,3,4-tetrahydro-2-naphthyl]methanesulfonamide To an ice-cooled solution of (R)-2-amino-8-(4-methylpiperazin-1-yl)-1,2,3,4-tetrahydronaphthalene (120 mg, 0.49 mmol) and triethylamine (0.50 mL, 3.6 mmol) in pyridine (15 mL) was added dropwise methanesulfonyl chloride (62 μL, 0.54 mmol). After the addition the reaction was allowed to stir at ambient temperature for 1 h. The solvent was evaporated in vacuo and the residue was purified on a silica gel column using chloroform/methanol/concentrated ammonium hydroxide (95:5:0.5) as the eluent. This gave, after crystallization from diethyl ether, 100 mg (63% yield) of the title compound as white crystals: mp 135–137° C.; $[\alpha]^{21}_D$ +22° (c 0.50, chloroform); EIMS (70 eV) m/z (relative intensity) 323 (59, M$^+$).

Example 36

(R)-N-[8-(4-Methylpiperazin-1-yl)-1,2,3,4-tetrahydro-2-naphthyl]cyclohexanecarboxamide To an ice-cooled solution of (R)-2-amino-8-(4-methylpiperazin-1-yl)-1,2,3,4-tetrahydronaphthalene (110 mg, 0.46 mmol) and triethylamine (92 μL, 0.66 mmol) in methylene chloride (20 mL) was added dropwise cyclohexanecarbonyl chloride (67 μL, 0.46 mmol) in methylene chloride (5 mL). After the addition the reaction was allowed to stir at ambient temperature for 10 min and then washed with dilute aqueous sodium hydrogen carbonate. The organic phase was separated, dried ($Na_2SO_4$), filtered and evaporated in vacuo and the residue was purified on a silica gel column using chloroform/ethanol saturated with $NH_3$ (100:3) as the eluent. This gave 71 mg (45% yield) of the title compound as white crystals: mp 183–184° C.; $[\alpha]^{21}_D$ +12° (c 1.0, chloroform); EIMS (70 eV) m/z (relative intensity) 355 (56, M$^+$).

Example 37

(R)-N-[8-(4-Methylpiperazin-1-yl)-1,2,3,4-tetrahydro-2-naphthyl]butanamide

To an ice-cooled solution of (R)-2-amino-8-(4-methylpiperazin-1-yl)-1,2,3,4-tetrahydronaphthalene (300 mg, 1.2 mmol) and triethylamine (260 μL, 1.8 mmol) in methylene chloride (50 mL) was added dropwise butyryl chloride (140 μL, 1.3 mmol) in methylene chloride (10 mL). After the addition the reaction was allowed to stir at ambient temperature for 1 h and then washed with a dilute aqueous sodium hydrogen carbonate solution. The phases were separated and the combined organic phases were dried ($Na_2SO_4$), filtered and evaporated in vacuo to give a crude product which was purified on a silica gel column using chloroform/methano/concentrated ammonium hydroxide (95:4:0.5) as the eluent. Yield: 330 mg (86%) of the title compound as white crystals: mp 131–132° C.; $[\alpha]^{21}_D$ +24° (c 0.05, chloroform); EIMS (70 eV) m/z (relative intensity) 315 (39, M$^+$).

Example 38

(R)-2-N-Butylamino-8-(4-methylpiperazin-1-yl)-1,2,3,4-tetrahydronaphthalene

To a solution of (R)-N-[8-(4-methylpiperazin-1-yl)-1,2,3,4-tetrahydro-2-naphthyl]butanamide (290 mg, 0.92 mmol) in anhydrous diethyl ether (35 mL) was added lithium aluminum hydride (100 mg, 2.8 mmol). The reaction mixture was heated at reflux for 7 h, then cooled and quenched by the addition of water (100 μL), 15% aqueous sodium hydroxide (100 μL) and again water (530 μL). The mixture was filtered, dried ($Na_2SO_4$) and evaporated in vacuo. Purification on a silica gel column using chloroform/methanol/concentrated ammonium hydroxide (95:5:0.5) as the eluent gave 170 mg (63% yield) of the title compound as a viscous oil. $[\alpha]^{21}_D$ +3.1° (c 1.0, chloroform); EIMS (70 eV) m/z (relative intensity) 301 (52, M$^+$). The oxalate salt was precipitated out of diethyl ether from 70 mg of the base. The crude salt was recrystallized from absolute ethanol and 77 mg (69% yield) of white crystals were isolated: mp 167–168° C.

Example 39

(R)-N-Butyl-N-[8-(4-methylpiperazin-1-yl)-1,2,3,4-tetrahydro-2-naphthyl]acetamide To an ice-cooled solution of (R)-2-N-butylamino-8-(4-methylpiperazin-1-yl)-1,2,3,4-tetrahydronaphthalene (91 mg, 0.30 mmol) and triethylamine (50 μL, 0.36 mmol) in methylene chloride (15 mL) was added dropwise acetyl chloride (23 μL, 0.36 mmol) in methylene chloride (5 mL). After the addition the reaction was allowed to stir at ambient temperature for 15 min and was then washed with water. The methylene chloride phase was dried ($Na_2SO_4$), filtered and evaporated in vacuo. Purification on a silica gel column using chloroform/methanol/concentrated ammonium hydroxide (95:5:0.5) as the eluent gave 99 mg (96% yield) of the title compound as a viscous oil. $[\alpha]^{21}_D$ +14° (c 1.0, chloroform); EIMS (70 eV) m/z (relative intensity) 343 (30, M$^+$).

Example 40

(R)-2-N-Methylamino-8-(4-methylpiperazin-1-yl)-1,2,3,4-tetrahydronaphthalene

To a solution of (R)-2-amino-8-(4-methylpiperazin-1-yl)-1,2,3,4-tetrahydronaphthalene (250 mg, 1.0 mmol) and triethylamine (210 µL, 1.5 mmol) in anhydrous 1,4-dioxane was added dropwise ethyl chloroformate (110 µL, 1.2 mmol) and the reaction was stirred for 15 min ar room temperature. The slightly yellow, cloudy solution was evaporated in vacuo and the residue was partitioned between chloroform and water. The organic phase was separated, dried ($Na_2SO_4$), filtered and evaporated in vacuo to give a crude oily product which was dissolved in diethyl ether (30 mL) and a small amount of terahydrofuran (8.0 mL). Lithium aluminum hydride (230 mg, 6.3 mmol) was added and the reaction mixture was heated at reflux for 20 h, cooled and then quenched by the addition of water (240 µL), 15% aqueous sodium hydroxide (240 µL) and again water (720 µL). The mixture was filtered, dried ($Na_2SO_4$) and evaporated in vacuo Purification on a silica gel column using chloroform/methanol/concentrated ammonium hydroxide (95:5:0.5) as the eluent gave 120 mg (47% yield) of the title compound as a viscous oil: $[\alpha]^{21}_D$ +20° (c 1.0, chloroform); EIMS (70 eV) m/z (relative intensity) 259 (64, M$^+$).

Example 41

(R)-N-Methyl-N-[8-(4-methylpiperazin-1-yl)-1,2,3,4-tetrahydro-2-naphthyl]acetamide To an ice-cooled solution of (R)-2-N-methylamino-8-(4-methylpiperazin-1-yl)-1,2,3,4-tetrahydronaphthalene (85 mg, 0.33 mmol) and triethylamine (55 µL, 0.4 mmol) in methylene chloride (20 mL) was added dropwise acetyl chloride (25 µL, 0.35 mmol) in methylene chloride (5 mL). After the addition the reaction was allowed to stir at ambient temperature for 15 min and then washed with water. The phases were separated and the combined organic phases were dried ($Na_2SO_4$), filtered and evaporated in vacuo to give a crude product which was purified on a silica gel column using chloroform/methanol/concentrated ammonium hydroxide (95:5:0.5) as the eluent. Yield: 61 mg (66%) of the title compound as an oil: $[\alpha]^{21}_D$ +54° (c 1.0, chloroform); EIMS (70 eV) m/z (relative intensity) 301 (18, M$^+$).

Example 42

(R)-2-N-Isopropylamino-8-(4-methylpiperazin-1-yl)-1,2,3,4-tetrahydronaphthalene (R)-2-Amino-8-(4-methylpiperazin-1-yl)-1,2,3,4-tetrahydronaphthalene (200 mg, 0.81 mmol) and aceton (0.20 mL, 2.7 mmol) was dissolved in methanol (5.0 mL). The pH was adjusted to 6 with acetic acid and sodium cyanoborohydride (66 mg, 1.1 mmol) was added. After 3 h at ambient temperature the solvent was evaporated in vacuo and the residue was partitioned between chloroform and water. The water phases was alkalized with 2 M aqueous sodium hydroxide solution and the phases were separated. The organic phase was dried ($Na_2SO_4$) and evaporated in vacuo. Chromatography on silica (eluent: chloroform/methanol/concentrated ammonium hydroxide (95:5:0.5)) gave 110 mg (47% yield) of the title compound as a viscous clear oil: $[\alpha]^{21}_D$ +3° (c 1.0, chloroform); EIMS (70 eV) m/z (relative intensity) 287 (23, M$^+$).

Example 43

(R)-N-Isopropyl-N-[8-(4-methylpiperazin-1-yl)-1,2,3,4-tetrahydro-2-naphthyl]acetamide To an ice-cooled solution of (R)-2-N-isopropylamino-8-(4-methylpiperazin-1-yl)-1,2,3,4-tetrahydronaphthalene (110 mg, 0.38 mmol) and triethylamine (63 µL, 0.46 mmol) in methylene chloride (20 mL) was added dropwise acetyl chloride (31 µL, 0.40 mmol) in methylene chloride (5 mL). After the addition the reaction was allowed to stir at ambient temperature for 15 min and then washed with water. The phases were separated and the combined organic phases were dried ($Na_2SO_4$), filtered and evaporated in vacuo to give a crude product which was purified on a silica gel column using chloroform/methanol/concentrated ammonium hydroxide (95:5:0.5) as the eluent. Yield: 120 mg (92%) of the title compound as an oil. $[\alpha]^{21}_D$ −24° (c 1.0, chloroform); EIMS (70 eV) m/z (relative intensity) 329 (31, M$^+$). The oxalate salt was precipitated out of diethyl ether and the crude salt was recrystallized from absolute ethanol/diethyl ether and 85 mg (48% yield) of white crystals were isolated: mp 181–183° C.

Example 44

(R)-N-[8-(4-Methylpiperazin-1-yl)-1,2,3,4-tetrahydro-2-naphthyl]-1,1'-biphenyl-4-carboxamide To an ice-cooled solution of (R)-2-amino-8-(4-methylpiperazin-1-yl)-1,2,3,4-tetrahydronaphthalene (100 mg, 0.41 mmol) and triethylamine (62 µL, 0.45 mmol) in methylene chloride (20 mL) was added dropwise 4-biphenylcarbonyl chloride (89 mg, 0.41 mmol) in methylene chloride (5 mL). After the addition the reaction was allowed to stir at ambient temperature for 15 min and then washed with water. The phases were separated and the combined organic phases were dried ($Na_2SO_4$), filtered and evaporated in vacuo to give a crude product which was purified on a silica gel column using chloroform/ethanol saturated with $NH_3$ (100:2.5) as the eluent. Yield: 100 mg (59%) of the title compound as white crystals: mp 232–233° C.; EIMS (70 eV) m/z (relative intensity) 425 (11, M$^+$).

Example 45

(R)-8-(4-Methylpiperazin-1-yl)-2-N-(4-phenyl)benzylamino-1,2,3,4-tetrahydronaphthalene To a solution of (R)-N-[8-(4-methylpiperazin-1-yl)-1,2,3,4-tetrahydro-2-naphthyl]-1,1'-biphenyl-4-carboxamide (210 mg, 0.49 mmol) in anhydrous diethyl ether (75 mL) and tetrahydrofuran (8 mL) was added lithium aluminum hydride (95 mg, 2.5 mmol). The reaction mixture was heated at reflux for 4 h, cooled and then quenched by the addition of water (95 µL), 15% aqueous sodium hydroxide (95 µL) and again water (290 µL). The mixture was filtered, dried ($Na_2SO_4$) and evaporated in vacuo. Purification on a silica gel column using chloroform/methanol/concentrated ammonium hydroxide (95:4:0.5) as the eluent gave 180 mg (87% yield) of the title compound as a viscous oil: $[\alpha]^{21}_D$ +15° (c 1.0, chloroform); EIMS (70 eV) m/z (relative intensity) 411 (7, M$^+$).

Example 46

(R)-N-[8-(4-Methylpiperazin-1-yl)-1,2,3,4-tetrahydro-2-naphthyl]-2-phenylthiazole-4-carboxamide To a solution of 4-carboxy-2-phenylthiazole (88 mg, 0.43 mmol) in anhydrous N,N-dimethylformamide (25 mL) was The oxalate salt was precipitated out of diethyl ether and the crude salt was recrystallized from absolute ethanol/diethyl ether and 97 mg (73% yield) of white crystals were isolated: mp 153–154° C.

added 1,1'-carbonyldiimidazole (73 mg, 0.45 mmol) and the reaction was heated at 75° C. When the carbon dioxide evolution had ceased (after 30 min), the reaction was cooled to room temperature and a solution of (R)-2-amino-8-(4-methylpiperazin-1-yl)-1,2,3,4-tetrahydronaphthalene (100 mg, 0.41 mmol) in anhydrous N,N-dimethylformamide (5 mL) was added. The reaction was allowed to stir at ambient temperature for 17 h and the solvent was evaporated in vacuo. Purification on a silica gel column using chloroform/ethanol saturated with $NH_3$ (100:3) as the eluent gave 99 mg (56% yield) of the title compound as white crystals: mp 175–176° C.; $[\alpha]^{21}_D$ '85° (c 1.0, chloroform); EIMS (70 eV) m/z (relative intensity) 432 (6, M$^+$).

Example 47

(R)-N-[8-(4-Methylpiperazin-1-yl)-1,2,3,4-tetrahydro-2-naphthyl]-2-(4-pyridyl)thiazole-4-carboxamide To a solution of 4-carboxy-2-(4-pyridyl)thiazole (89 mg, 0.43 mmol) in anhydrous N,N-dimethylformamide (25 mL) was added 1,1'-carbonyldiimidazole (73 mg, 0.45 mmol) and the reaction was heated at 75° C. When the carbon dioxide evolution had ceased (after 30 min), the reaction was cooled to room temperature and a solution of (R)-2-amino-8-(4-methylpiperazin-1-yl)-1,2,3,4-tetrahydronaphthalene (100 mg, 0.41 mmol) in anhydrous N,N-dimethylformamide (5 mL) was added. The reaction was allowed to stir at ambient temperature for 17 h and the solvent was evaporated in vacuo. Purification on a silica gel column using chloroform/ethanol saturated with $NH_3$ (100:3) as the eluent gave 110 mg (61% yield) of the title compound as white crystals: mp 187–188° C.; $[\alpha]^{21}_D$ '82° (c 1.0, chloroform); EIMS (70 eV) m/z (relative intensity) 433 (2, M$^+$).

Example 48

(R)-N-[8-(4-Methylpiperazin-1-yl)-1,2,3,4-tetrahydro-2-naphthyl]benzamide

To an ice-cooled solution of (R)-2-amino-8-(4-methylpiperazin-1-yl)-1,2,3,4-tetrahydronaphthalene (210 mg, 0.86 mmol) and triethylamine (180 μL, 1.28 mmol) in methylene chloride (30 mL) was added dropwise benzoyl chloride (130 mg, 0.90 mmol) in methylene chloride (5 mL). After the addition the reaction was allowed to stir at ambient temperature for 15 min and then washed with water. The phases were separated and the combined organic phases were dried ($Na_2SO_4$), filtered and evaporated in vacuo to give a crude product which was purified on a silica gel column using chloroform/ethanol saturated with $NH_3$ (100:3) as the eluent. Yield: 250 mg (84%) of the title compound as white crystals: mp 195–196° C.; $[\alpha]^{21}_D$ −31° (c 1.0, $CHCL_3$); EIMS (70 eV) m/z (relative intensity) 349 (53, M$^+$).

Example 49

(R)-N-[8-(4-Methylpiperazin-1-yl)-1,2,3,4-tetrahydro-2-naphthyl]-4-methoxybenzamide To an ice-cooled solution of (R)-2-amino-8-(4-methylpiperazin-1-yl)-1,2,3,4-tetrahydronaphthalene (130 mg, 0.53 mmol) and triethylamine (110 μL, 0.80 mmol) in methylene chloride (30 mL) was added dropwise 4-methoxybenzoyl chloride (95 mg, 0.56 mmol) in methylene chloride (5 mL). After the addition the reaction was allowed to stir at ambient temperature for 15 min and then washed with water. The phases were separated and the combined organic phases were dried ($Na_2SO_4$), filtered and evaporated in vacuo to give a crude product which was purified on a silica gel column using chloroform/ethanol saturated with $NH_3$ (100:3) as the eluent. Yield: 143 mg (71%) of the title compound as white crystals: mp 186–187° C.; $[\alpha]^{21}_D$ −52° (c 0.50, $CHCL_3$); EIMS (70 eV) m/z (relative intensity) 379 (23, M$^+$).

Example 50

(R)-N-[8-(4-Methylpiperazin-1-yl)-1,2,3,4-tetrahydro-2-naphthyl]-4-cyanobenzamide To an ice-cooled solution of (R)-2-amino-8-(4-methylpiperazin-1-yl)-1,2,3,4-tetrahydronaphthalene (130 mg, 0.53 mmol) and triethylamine (110 μL, 0.80 mmol) in methylene chloride (25 mL) was added dropwise 4-cyanobenzoyl chloride (92 mg, 0.56 mmol) in methylene chloride (5 mL). After the addition the reaction was allowed to stir at ambient temperature for 15 min and then washed with water. The phases were separated and the combined organic phases were dried ($Na_2SO_4$), filtered and evaporated in vacuo to give a crude product which was purified on a silica gel column using chloroform/ethanol saturated with $NH_3$ (100:4) as the eluent. Yield: 120 mg (61%) of the title compound as white crystals: mp 184–186° C.; $[\alpha]^{21}_D$ −47° (c 1.0, $CHCL_3$); EIMS (70 eV) m/z (relative intensity) 374 (54, M$^+$).

Example 51

(R)-N-[8-(4-Methylpiperazin-1-yl)-1,2,3,4-tetrahydro-2-naphthyl]-4-trifluormethylsulfonyloxybenzamide 4-Carboxyphenyl trifluoromethanesulfonate (0.40 g, 1.5 mmol; described in: Looker, J. H.; Hayes, C. H.; Thatcher, D. N. *J. Am. Chem. Soc.* 1957, 79, 741–4) was dissolved in thionyl chloride (10 mL) and heated at 40° C. for 45 min. The excess of thionyl chloride was evaporated in vacuo, the residue was treated with toluene and again the solvent was removed in vacuo. The crude acid chloride (280 mg, 0.96 mmol) was dissolved in methylene chloride (5 mL) and added dropwise to an ice-cooled solution of (R)-2-amino-8-(4-methylpiperazin-1-yl)-1,2,3,4-tetrahydronaphthalene (110 mg, 0.46 mmol) and triethylarine (96 μL, 0.69 mmol) in methylene chloride (20 mL). After the addition the reaction was allowed to stir at ambient temperature for 15 min and then washed with water. The phases were separated and the combined organic phases were dried ($Na_2SO_4$), filtered and evaporated in vacuo to give a crude product which was purified on a silica gel column using chloroform/ethanol saturated with $NH_3$ (100:3) as the eluent. Yield: 100 mg (44%) of the title compound as white crystals: mp 178–180° C.; $[\alpha]^{21}_D$ −31° (c 1.0, chloroform); EIMS (70 eV) m/z (relative intensity) 497 (17, M$^+$).

Example 52

(R)-N-[8-(4-tert-Butyloxycarbonylpiperazin-1-yl)-1,2,3,4-tetrahydro-2-naphthyl]-4-morpholinobenzamide To a solution of 4-morpholinobenzoic acid (0.59 g, 2.8 mmol; described in: Degutis, J.; Rasteikiene, L.; Degutiene, A. *Zh. Org. Khim.* 1978, 14(10), 2060–2064) in anhydrous N,N-dimethylformamide (30 mL) was added 1,1'-carbonyldiimidazole (0.48 g, 3.0 mmol) and the reaction was heated at 75° C. When the carbon dioxide evolution had ceased (after 30 min), the reaction was cooled to room temperature and a solution of tert-butyl (R)-4-(7-amino-5,6,7,8-tetrahydro-1-naphthyl)piperazine-1-carboxylate (0.90 g, 2.7 mmol) in anhydrous N,N-dimethylformamide (15 mL) was added. The reaction was allowed to stir at ambient temperature for 24 h and the solvent was evaporated in vacuo. Purification on a silica gel column using chloroform/ethanol saturated with $NH_3$ (100:2) as the eluent gave 1.5 g (84% yield) of the title compound as a dark-red viscous oil: $[\alpha]^{21}_D$ −45° (c 0.50, chloroform); EIMS (70 eV) m/z (relative intensity) 520 (5, M⁺).

Example 53

(R)-N-[8-(Piperazin-1-yl)-1,2,3,4-tetrahydro-2-naphthyl]-4-morpholinobenzamide

To an ice-cooled solution of (R)-N-[8-(4-tert-butyloxycarbonylpiperazin-1-yl)-1,2,3,4-tetrahydro-2-naphthyl]-4-morpholinophenylcarboxamide (1.0 g, 2 mmol) in methylene chloride (100 mL) was added trifluoroacetic acid (3 mL). The reaction was stirred at ambient temperature for 7 h. The solvent was evaporated in vacuo and the residue was dissolved in water (20 mL), alkalized with a 2 M aqueous sodium hydroxide solution and extracted, twice, with methylene chloride. The phases were separated, the combined organic phases were dried ($Na_2SO_4$), filtered and evaporated in vacuo. Purification on a silica gel column using chloroform/methanol/concentrated ammonium hydroxide (95:5:0.5) as the eluent gave 580 mg (70% yield) of the title compound as white crystals: mp 202–203° C.; $[\alpha]^{21}_D$ −56° (c 1.0, chloroform); EIMS (70 eV) m/z (relative intensity) 420 (5, M⁺).

Example 54

(R)-N-[8-(4-Methylpiperazin-1-yl)-1,2,3,4-tetrahydro-2-naphthyl]-4-morpholinobenzamide To a solution of 4-morpholinobenzoic acid (0.89 g, 4.3 mmol; described in: Degutis, J.; Rasteikiene, L.; Degutiene, A. Zh. Org. Khim. 1978, 14(10), 2060–2064) in anhydrous N,N-dimethylformamide (30 mL) was added 1,1'-carbonyldiimidazole (0.73 g, 4.3 mmol) and the reaction was heated at 75° C. When the carbon dioxide evolution had ceased (after 30 min), the reaction was cooled to room temperature and a solution of (R)-2-amino-8-(4-methylpiperazin-1-yl)-1,2,3,4-tetrahydronaphthalene (1.0 g, 4.1 mmol) in anhydrous N,N-dimethylformamide (5 mL) was added. The reaction was allowed to stir at ambient temperature for 24 h and the solvent was evaporated in vacuo. Purification on a silica gel column using chloroform/methanol/concentrated ammonium hydroxide (95:5:0.5) as the eluent gave 1.5 g (85% yield) of the title compound as white crystals: mp 230–231° C.; $[\alpha]^{21}_D$ −49° (c 1.0, chloroform); EIMS (70 eV) m/z (relative intensity) 434 (10, M⁺).

Example 55

(S)-N-[8-(4-Methylpiperazin-1-yl)-1,2,3,4-tetrahydro-2-naphthyl]-4-morpholinobenzamide The title compound was synthesized according to the procedure of Example 54 using the (S)-form: mp 228–230° C.; $[\alpha]^{21}_D$ +35° (c 1, MeOH); EIMS (70 eV) m/z (relative intensity) 434 (1, M⁺)

Example 56

R)-N-[8-(4-Ethylpiperazin-1-yl)-1,2,3,4-tetrahydro-2-naphthyl]-4-morpholinobenzamide To a solution of (R)-N-8-(piperazin-1-yl)-1,2,3,4-tetrahydro-2-naphthyl]-4-morpholinobenzamide (90 mg, 0.21 mmol) in acetone (20 mL) were added potassium carbonate (44 mg, 0.32 mmol) and iodoethane (26 μL, 0.32 mmol) and the reaction was stirred for 48 h at ambient temperature. The reaction mixture was filtered and the solvent evaporated in vacuo. The residue was partitioned between methylene chloride and water, the phases were separated, and the organic phase was dried ($Na_2SO_4$), filtered and evaporated in vacuo. Purification on a silica gel column using chloroform/ethanol saturated with $NH_3$ (100:3) as the eluent gave 63 mg (66% yield) of the title compound as white crystals: mp: 204–206° C.; $[\alpha]^{21}_D$ −67° (c 1.0, chloroform); EIMS (70 eV) m/z (relative intensity) 448 (21, M⁺).

Example 57

(R)-N-[8-(4-Propylpiperazin-1-yl)-1,2,3,4-tetrahydro-2-naphthyl]-4-morpholinobenzamide To a solution of (R)-N-8-(piperazin-1-yl)-1,2,3,4-tetrahydro-2-naphthyl]4-morpholinobenzamide (120 mg, 0.29 mmol) in acetone (20 mL) were added potassium carbonate (59 mg, 0.43 mmol) and 1-iodopropan (42 μL, 0.43 mmol) and the reaction was stirred for 4 days at ambient temperature. The reaction mixture was filtered and the solvent evaporated in vacuo. The residue was partitioned between methylene chloride and water, the phases separated and the organic phase was dried ($Na_2SO_4$), filtered and evaporated in vacuo. Purification on a silica gel column using chloroform/ethanol saturated with $NH_3$ (100:4) as the eluent gave 58 mg (44% yield) of the title compound as a amorphous solid. Crystallization from ethyl acetate/diethyl ether gave 11 mg (8%) of white crystals: mp 183–185° C.; $[\alpha]^{21}_D$ −60° (c 0.50, chloroform); EIMS (70 eV) m/z (relative intensity) 462 (25, M⁺).

Example 58

(R)-8-(4-Methylpiperazin-1-yl)-2-[N-(4-morpholino)benzylamino]-1,2,3,4-tetrahydronaphthalene To a solution of (R)-N-[8-(4-methylpiperazin-1-yl)-1,2,3,4-tetrahydro-2-naphthyl]-4-morpholinobenzamide (200 mg, 0.46 mmol) in anhydrous tetrahydrofuran (25 mL) was added lithium aluminium hydride (200 mg, 5.3 mmol). The reaction mixture was heated at reflux for 15 h, then cooled and quenched by the addition of water (200 μL), 15% aqueous sodium hydroxide (200 μL) and again water (600 μL). The mixture was filtered, dried ($Na_2SO_4$) and evaporated in vacuo. Purification on a silica gel column using chloroform/methanol/concentrated ammonium hydroxide (95:5:0.5) as the eluent gave 61 mg (32% yield) of the title compound as white crystals: $[\alpha]^{21}_D$ +19° (c 1.0, chloroform); EIMS (70 eV) m/z (relative intensity) 420 (8, M⁺).

Example 59

3-Methyl-4-morpholinobenzonitrile

To a solution of 4-bromo-3-methylbenzonitrile (11 g, 56 mmol) and potassium fluoride (3.3 g, 56 mmol) in anhydrous N,N-dimethylformamide (150 mL) was added morpholine (15 g, 170 mmol) and the reaction was heated at 145° C. for 4 days. The solvent was evaporated in vacuo and the residue was partitioned between diethyl ether and water. The phases was separated and the organic phase was dried ($Na_2SO_4$), filtered and evaporated in vacuo. Purification on a silica gel column using toluene followed by chloroform as eluents gave 1.3 g (11% yield) of the title compound as white crystals: mp 85–86° C.; EIMS (70 eV) m/z (relative intensity) 202 (71, M+).

Example 60

3-Methyl-4-morpholinobenzoic acid

To a solution of 3-methyl-4-morpholinobenzonitrile (1.0 g, 4.9 mmol) in glacial acetic acid (10 mL) was added a 20% aqueous hydrochloric acid solution (60 mL) and the reaction was heated at reflux for 35 h. The acetic acid was evaporated in vacuo and the remaining water solution was alkalized with 2 M aqueous sodium hydroxide solution to pH 8. The solution was washed, twice, with chloroform and the water phase was adjusted to pH 4 with a 2 M aqueous hydrochloric acid solution. The product was filtered off and dried in vacuo to afford 1.0 g (91% yield) of the title compound as white crystals: mp 220–221° C.; EIMS (70 eV) m/z (relative intensity) 221 (100, M+).

Example 61

(R)-N-[8-(4-Methylpiperazin-1-yl)-1,2,3,4-tetrahydro-2-naphthyl]-3-methyl-4-morpholinobenzamide To a solution of 3-methyl-4-morpholinobenzoic acid (110 mg, 0.51 mmol) in anhydrous N,N-dimethylformamide (10 mL) was added 1,1'-carbonyldiimidazole (87 mg, 0.54 mmol) and the reaction was heated at 75° C. When the carbon dioxide evolution had ceased (after 30 min), the reaction was cooled to room temperature and a solution of (R)-2-amino-8-(4-methylpiperazin-1-yl)-1,2,3,4-tetrahydronaphthalene (120 mg, 0.49 mmol) in anhydrous N,N-dimethylformamide (5 mL) was added. The reaction was allowed to stir at ambient temperature for 15 h and the solvent was evaporated in vacuo. Purification on a silica gel column using chloroform/ethanol saturated with $NH_3$ (100:2) as the eluent gave 110 mg (50% yield) of the title compound as white crystals: mp 172–175° C.; $[\alpha]^{21}_D$ '47° (c 1.0, chloroform); EIMS (70 eV) m/z (relative intensity) 448 (5, M+).

Example 62

(R)-[8-(4-methylpiperazin-1-yl)-1,2,3,4-tetrahydro-2-naphthyl]-4-piperidinobenzamide To a solution of 4-piperidinobenzoic acid (88 mg, 0.43 mmol; described in: Weringa, W. D.; Janssen, M. J. *Recl. Trav. Chim. Pays-Bas* 1968, 87(12), 1372–1380) in anhydrous N,N-dimethylformamide (5 mL) was added 1,1'-carbonyldiimidazole (73 mg, 0.45 mmol) and the reaction was heated at 75° C. When the carbon dioxide evolution had ceased (after 30 min), the reaction was cooled to room temperature and a solution of (R)-2-amino-8-(4-methylpiperazin-1-yl)-1,2,3,4-tetrahydronaphthalene (100 mg, 0.41 mmol) in anhydrous N,N-dimethylformamide (5 mL) was added. The reaction was allowed to stir at ambient temperature for 17 h and the solvent was evaporated in vacuo. Purification on a silica gel column using chloroform/ethanol saturated with $NH_3$ (100:2) as the eluent gave 75 mg (42% yield) of the title compound as white crystals: mp 196–198° C.; $[\alpha]^{21}_D$ '63° (c 1.0, chloroform); EIMS (70 eV) m/z (relative intensity) 432 (2, M+).

Example 63

(R)-N-[8-(4-Methylpiperazin-1-yl)-1,2,3,4-tetrahydro-2-naphthyl]-4-cyclohexylbenzamide 4-Cyclohexylbenzoic acid (0.50 g, 2.4 mmol) was dissolved in thionyl chloride (20 mL) and heated at reflux for 30 min. The excess of thionyl chloride was evaporated in vacuo, the residue was treated with toluene and again the solvent was removed in vacuo. Crude acid chloride (96 mg, 0.43 mmol) was dissolved in methylene chloride (5 mL) and added dropwise to an ice-cooled solution of (R)-2-amino-8-(4-methylpiperazin-1-yl)-1,2,3,4-tetrahydronaphthalene (100 mg, 0.41 mmol) and triethylamine (62 μL, 0.45 mmol) in methylene chloride (20 mL). After the addition the reaction was allowed to stir at ambient temperature for 15 min and then washed with water. The phases were separated and the organic phase was dried ($Na_2SO_4$), filtered and evaporated in vacuo to give a crude product which was purified on a silica gel column using chloroform/methanol/concentrated ammonium hydroxide (95:5:0.5) as the eluent. Yield: 150 mg (85%) of the title compound as white crystals: mp 224–226° C.; $[\alpha]^{21}_D$ –43° (c 1.0, chloroform); EIMS (70 eV) m/z (relative intensity) 431 (2, M+).

Example 64

(S)-N-[8-(4Methylpiperazin-1-yl)-1,2,3,4-tetrahydro-2-naphthyl]-4-N,N-diethylaminobenzamide 4-(diethylamino)benzoic acid (94 mg, 0.5 mmol) and 1,1-carbonyldiimidazole (86 mg, 0.5 mmol) were dissolved in N,N-dimethylformamide (4 mL) under nitrogen atmosphere and stirred at 70° C. for 30 minutes. The reaction mixture was allowed to attain room temperature before (S)-2-Amino-8-(4-methylpiperazin-1-yl)-1,2,3,4-tetrahydronaphthalene (0.1 g, 0.4 mmol), dissolved in N,N-dimethylformamide (4 mL), was added. The mixture was stirred at room temperature for 10 days before it was diluted with ethyl acetate, washed with 2 M ammonia and dried ($MgSO_4$). The solvent was removed in vacuo to give a residue which was purified by flash chromatography on silica gel with methylene chloride/ethyl acetate 20:1 (containing 0.5% of ammonia) as eluent. yield 40 mg (23%): mp 168–170° C. (dec); $[\alpha]^{21}_D$ +25° (c 0.25, MeOH) EIMS (70 eV) m/z (relative intensity) 420 (13, M+).

Example 65

(R)-N-[8-(4-Methylpiperazin-1-yl)-1,2,3,4-tetrahydro-2-naphthyl]-4-trifluoromethylbenzamide To an ice-cooled solution of (R)-2-amino-8-(4-methylpiperazin-1-yl)-1,2,3,4-tetrahydronaphthalene (110 mg, 0.44 mmol) and triethyl amine (91 μL, 0.66 mmol) in methylene chloride (20 mL) was added dropwise 4-(trifluoromethyl)benzoyl chloride (96 mg, 0.46 mmol) in methylene chloride (5 mL). After the addition the reaction was allowed to stir at ambient temperature for 15 min and was then washed with diluted aqueous sodium hydrogen carbonate. The phases were separated and the organic phase was dried ($Na_2SO_4$), filtered and evaporated in vacuo to give a crude product which was purified on a silica gel column using chloroform/ethanol saturated with $NH_3$ (100:2) as the eluent. Yield: 150 mg (81%) of the title compound as white crystals: mp 203–204° C.; $[\alpha]^{21}_D$ –20° (c 1.0, chloroform); EIMS (70 eV) m/z (relative intensity) 417 (10, M+).

Example 66

(S)-N-[8-(4-Methylpiperazin-1-yl)-1,2,3,4-tetrahydro-2-naphthyl]-4-trifluoromethylbenzamide The title compound was synthesized according to the procedure of Example 65 using the (S)-form: mp 202–204°

C.; $[\alpha]^{21}_D$ –13° (c 1, MeOH); EIMS (70 eV) m/z (relative intensity) 417 (5, M+).

Example 67

(R)-N-[8-(4-Methylpiperazin-1-yl)-1,2,3,4-tetrahydro-2-naphthyl]-4-methylsulfonyloxybenzamide A suspension of 4-methylsulfonyloxybenzoic acid (0.60 g, 2.8 mmol; described in: Looker, J. H.; Hayes, C. H.; Thatcher, D. N. *J. Am. Chem. Soc.* 1957, 79, 741–4) in thionyl chloride (15 mL) was heated at reflux for 30 min (the mixture became homogeneous). The excess of thionyl chloride was evaporated in vacuo, the residue was treated with toluene and again the solvent was removed in vacuo. Crude acid chloride (110 mg, 0.47 mmol) was dissolved in methylene chloride (5 mL) and added dropwise to an ice-cooled solution of (R)-2-amino-8-(4-methylpiperazin-1-yl)-1,2,3,4-tetrahydronaphthalene (110 mg, 0.45 mmol) and triethylamine (94 µL, 0.68 mmol) in methylene chloride (20 mL). After the addition the reaction was allowed to stir at ambient temperature for 15 min and then washed with dilute aqueous sodium hydrogen carbonate. The phases were separated and the organic phase was dried (Na$_2$SO$_4$), filtered and evaporated in vacuo to give a crude product which was purified on a silica gel column using chloroform/ethanol saturated with NH$_3$ (100:3) as the eluent. Yield: 160 mg (78%) of the title compound as white crystals: mp 199–200° C.; $[\alpha]^{21}_D$ –20° (c 1.0, chloroform); EIMS (70 eV) m/z (relative intensity) 443 (3, M+).

Example 68

(R)-N-[8-(4-Methylpiperazin-1-yl)-1,2,3,4-tetrahydro-2-naphthyl]-4-hydroxybenzamide A suspension of sodium 4-acetoxybenzoate (1.0 g, 5.4 mmol) in thionyl chloride (15 mL) was heated at reflux for 1 h (the mixture became homogeneous). The excess of thionyl chloride was evaporated in vacuo, the residue was treated with toluene and again the solvent was removed in vacuo. Crude acid chloride (150 mg, 0.77 mmol) was dissolved in methylene chloride (5 mL) and added dropwise to an ice-cooled solution of (R)-2-amino-8-(4-methylpiperazin-1-yl)-1,2,3,4-tetrahydronaphthalene (180 mg, 0.73 mmol) and triethylamine (150 µL, 1.1 mmol) in methylene chloride (20 mL). After the addition the reaction was allowed to stir at ambient temperature for 15 min and was then washed with diluted aqueous sodium hydrogen carbonate. The phases were separated and the organic phase was dried (Na$_2$SO$_4$), filtered and evaporated in vacuo. The residue was dissolved in 99.5% ethanol (15 mL) and concentrated hydrochloric acid (5 mL) was added. After 17 h, the pH was adjusted to 8 and the solvent evaporated in vacuo. The residue was partitioned between water and chloroform. The organic phase was separated, dried (Na$_2$SO$_4$), filtered and evaporated in vacuo to give a crude product which was purified on a silica gel column using chloroform/ethanol saturated with NH$_3$ (100:4) as the eluent. Yield: 70 mg (26%) of the title compound as an oil: $[\alpha]^{21}_D$ –17° (c 0.50, chloroform); EIMS (70 eV) m/z (relative intensity) 365 (24, M+).

Example 69

(R)-N-[8-(4-Methylpiperazin-1-yl)-1,2,3,4-tetrahydro-2-naphthyl]-4-ethylbenzamide To an ice-cooled solution of (R)-2-amino-8-(4-methylpiperazin-1-yl)-1,2,3,4-tetrahydronaphthalene (110 mg, 0.46 mmol) and triethylamine (95 µL, 0.68 mmol) in methylene chloride (20 mL) was added dropwise 4-ethylbenzoyl chloride (81 mg, 0.48 mmol) in methylene chloride (5 mL). After the addition the reaction was allowed to stir at ambient temperature for 15 min and then washed with water. The phases were separated and the organic phase was dried (Na$_2$SO$_4$), filtered and evaporated in vacuo to give a crude product which was purified on a silica gel column using chloroform/ethanol saturated with NH$_3$ (100:4) as the eluent. Yield: 120 mg (66%) of the title compound as white crystals: mp 177–178° C.; $[\alpha]^{21}_D$ –43° (c 1.0, chloroform); EIMS (70 eV) m/z (relative intensity) 377 (27, M+).

Example 70

(R)-N-[8-(4-Methylpiperazin-1-yl)-1,2,3,4-tetrahydro-2-naphthyl]-4-butoxybenzamide To an ice-cooled solution of (R)-2-amino-8-(4-methylpiperazin-1-yl)-1,2,3,4-tetrahydronaphthalene (110 mg, 0.41 mmol) and triethylamine (95 µL, 0.69 mmol) in methylene chloride (20 mL) was added dropwise 4-butoxybenzoyl chloride (103 mg, 0.48 mmol) in methylene chloride (5 mL). After the addition the reaction was allowed to stir at ambient temperature for 15 min and was then washed with dilute aqueous sodium hydrogen carbonate. The phases were separated and the organic phase was dried (Na$_2$SO$_4$), filtered and evaporated in vacuo to give a crude product which was purified on a silica gel column using chloroform/ethanol saturated with NH$_3$ (100:2) as the eluent. Yield: 150 mg (75%) of the title compound as white crystals: mp 190–191° C.; $[\alpha]^{21}_D$ –49° (c 1.0, chloroform); EIMS (70 eV) m/z (relative intensity) 421 (0.6, M+).

Example 71

(S)-N-[8-(4-Methylpiperazin-1-yl)-1,2,3,4-tetrahydro-2-naphthyl]-4-butoxybenzamide The title compound was synthesized according to the procedure of Example 70 using the (S)-form: mp 190–192° C.; $[\alpha]^{21}_D$ +8° (c 1, MeOH); EIMS (70 eV) m/z (relative intensity) 421 (1, M+).

Example 72

(R)-N-[8-(4-Methylpiperazin-1-yl)-1,2,3,4-tetrahydro-2-naphthyl]-4-fluorobenzamide To an ice-cooled solution of (R)-2-amino-8-(4-methylpiperazin-1-yl)-1,2,3,4-tetrahydronaphthalene (130 mg, 0.53 mmol) and triethylamine (110 µL, 0.79 mmol) in methylene chloride (25 mL) was added dropwise 4-fluorobenzoyl chloride (89 mg, 0.56 mmol) in methylene chloride (5 mL). After the addition, the reaction was allowed to stir at ambient temperature for 15 min and was then washed with diluted aqueous sodium hydrogen carbonate. The phases were separated and the organic phase was dried (Na$_2$SO$_4$), filtered and evaporated in vacuo to give a crude product which was purified on a silica gel column using chloroform/ethanol saturated with NH$_3$ (100:3) as the eluent. Yield: 130 mg (65%) of the title compound as white crystals: mp 189–190° C.; $[\alpha]^{21}_D$ '30° (c 1.0, chloroform); EIMS (70 eV) m/z (relative intensity) 367 (11, M+).

Example 73

(R)-N-[8-(4-Methylpiperazin-1-yl)-1,2,3,4-tetrahydro-2-naphthyl]-4-bromobenzamide To an ice-cooled solution of (R)-2-amino-8-(4-methylpiperazin-1-yl)-1,2,3,4-tetrahydronaphthalene (130 mg, 0.53 mmol) and triethylamine (110 µL, 0.79 mmol) in methylene chloride (25 mL) was added dropwise 4-bromobenzoyl chloride (122 mg, 0.56 mmol) in methylene chloride (5 mL). After the addition, the reaction was allowed to stir at ambient temperature for 15 min and was then washed with dilute aqueous sodium hydrogen carbonate. The phases were separated and the organic phase was dried ($Na_2SO_4$), filtered and evaporated in vacuo to give a crude product which was purified on a silica gel column using chloroform/ethanol saturated with $NH_3$ (100:4) as the eluent. Yield: 120 mg (51%) of the title compound as white crystals: mp 200–201° C.; $[\alpha]^{21}_D$ −32° (c 1.0, chloroform), EIMS (70 eV) m/z (relative intensity) 427 and 429 (3, M$^+$).

Example 74

(R)-N-[8-(4-Methylpiperazin-1-yl)-1,2,3,4-tetrahydro-2-naphthyl]-4-chlorobenzamide To an ice-cooled solution of (R)-2-amino-8-(4-methylpiperazin-1-yl)-1,2,3,4-tetrahydronaphthalene (110 mg, 0.45 mmol) and triethylamine (93 µL, 0.67 mmol) in methylene chloride (25 mL) was added dropwise 4-chlorobenzoyl chloride (83 mg, 0.47 mmol) in methylene chloride (5 mL). After the addition, the reaction was allowed to stir at ambient temperature for 15 min and was then washed with diluted aqueous sodium hydrogen carbonate. The phases were separated and the organic phase was dried ($Na_2SO_4$), filtered and evaporated in vacuo to give a crude product which was purified on a silica gel column using chloroform/ethanol saturated with $NH_3$ (100:3) as the eluent. Yield: 97 mg (56%) of the title compound as white crystals: mp 204–205° C.; $[\alpha]^{21}_D$ −46° (c 1.0, chloroform); EIMS (70 eV) m/z (relative intensity) 383 (19, M$^+$).

Example 75

(R)-N-[8-(4-Methylpiperazin-1-yl)-1,2,3,4-tetrahydro-2-naphthyl]-4-benzylbenzamide 4-Benzylbenzoic acid (0.50 g, 2.4 mmol) was dissolved in thionyl chloride (10 mL) and heated at reflux for 20 min. The excess of thionyl chloride was evaporated in vacuo, the residue was treated with toluene and again the solvent was removed in vacuo. Crude acid chloride (100 mg, 0.46 mmol) was dissolved in methylene chloride (5 mL) and added dropwise to an ice-cooled solution of (R)-2-amino-8-(4-methylpiperazin-1-yl)-1,2,3,4-tetrahydronaphthalene (110 mg, 0.44 mmol) and triethylamine (90 µL, 0.65 mmol) in methylene chloride (25 mL). After the addition, the reaction was allowed to stir at ambient temperature for 15 min and was then washed with dilute aqueous sodium hydrogen carbonate. The phases were separated and the organic phase was dried ($Na_2SO_4$), filtered and evaporated in vacuo to give a crude product which was purified on a silica gel column using chloroform/ethanol saturated with $NH_3$ (100:3) as the eluent. Yield: 130 mg (62%) of the title compound as white crystals: mp 191–192° C.; $[\alpha]^{21}_D$ −39° (c 1.0, chloroform); EIMS (70 eV) m/z (relative intensity) 439 (28, M$^+$).

Example 76

(R)-N-[8-(4-Methylpiperazin-1-yl)-1,2,3,4-tetrahydro-2-naphthyl]-4-benzoylbenzamide 4-Benzoylbenzoic acid (0.50 g, 2.2 mmol) was dissolved in thionyl chloride (15 mL) and heated at reflux for 15 min. The excess of thionyl chloride was evaporated in vacuo, the residue was treated with toluene and again the solvent was removed in vacuo. Crude acid chloride (150 mg, 0.60 mmol) was dissolved in methylene chloride (5 mL) and added dropwise to an ice-cooled solution of (R)-2-amino-8-(4-methylpiperazin-1-yl)-1,2,3,4-tetrahydronaphthalene (140 mg, 0.57 mmol) and triethylamine (120 µL, 0.86 mmol) in methylene chloride (30 mL). After the addition, the reaction was allowed to stir at ambient temperature for 15 min and was then washed with dilute aqueous sodium hydrogen carbonate. The phases were separated and the organic phase was dried ($Na_2SO_4$), filtered and evaporated in vacuo to give a crude product which was purified on a silica gel column using chloroform/ethanol saturated with $NH_3$ (100:3) as the eluent. Yield: 120 mg (48%) of the title compound as white crystals: mp 194–195° C.; $[\alpha]^{21}_D$ −51° (c 1.0, chloroform); EIMS (70 eV) m/z (relative intensity) 453 (2, M$^+$).

Example 77

(R)-N-[8-(4-Methylpiperazin-1-yl)-1,2,3,4-tetrahydro-2-naphthyl]-4-(trifluoroacetyl)benzamide 4-(Trifluoroacetyl)benzoic acid (0.50 g, 2.4 mmol) was dissolved in thionyl chloride (15 mL) and heated at reflux for 20 min. The excess of thionyl chloride was evaporated in vacuo, the residue was treated with toluene and again the solvent was removed in vacuo. Crude acid chloride (97 mg, 0.43 mmol) was dissolved in methylene chloride (5 mL) and added dropwise to an ice-cooled solution of (R)-2-amino-8-(4-methylpiperazin-1-yl)-1,2,3,4-tetrahydronaphthalene (100 mg, 0.41 mmol) and triethylamine (85 µL, 0.61 mmol) in methylene chloride (35 mL). After the addition, the reaction was allowed to stir at ambient temperature for 15 min and was then washed with dilute aqueous sodium hydrogen carbonate. The phases were separated and the organic phase was dried ($Na_2SO_4$), filtered and evaporated in vacuo to give a crude product which was purified on a silica gel column using chloroform/ethanol saturated with $NH_3$ (100:3) as the eluent. Yield: 98 mg (54%) of the title compound as slightly yellow crystals: mp 91–93° C.; $[\alpha]^{21}_D$ −47° (c 1.0, chloroform); EIMS (70 eV) m/z (relative intensity) 453 (27, M$^+$).

Example 78

(R)-N-[8-(4-Methylpiperazin-1-yl)-1,2,3,4-tetrahydro-2-naphthyl]-4-(1H-pyrrol-1-yl)benzamide To a solution of 4-(1H-pyrrol-1-ylbenzoic acid (96 mg, 0.51 mmol) in anhydrous N,N-dimethylformamide (25 mL) was added 1,1'-carbonyldiimidazole (87 mg, 0.54 mmol) and the reaction was heated at 75° C. When the carbon dioxide evolution had ceased (after 30 min), the reaction was cooled to room temperature and a solution of (R)-2-amino-8-(4-methylpiperazin-1-yl)-1,2,3,4-tetrahydronaphthalene (120 mg, 0.49 mmol) in anhydrous N,N-dimethylformamide (5 mL) was added. The reaction was allowed to stir at ambient temperature for 17 h and the solvent was evaporated in vacuo. Purification on a silica gel column using chloroform/ethanol saturated with $NH_3$ (100:3) as the eluent gave 128 mg (62% yield) of the title compound as white crystals: mp 245–247° C.; $[\alpha]^{21}_D$ −69° (c 1.0, chloroform); EIMS (70 eV) m/z (relative intensity) 414 (15, M$^+$).

Example 79

(R)-N-[8-(4-Methylpiperazin-1-yl)-1,2,3,4-tetrahydro-2-naphthyl]-4-(N,N-dipropylaminosulphonyl)benzamide To a solution of 4-(N,N-dipropylaminosulphonyl)benzoic acid (120 mg, 0.43 mmol) in anhydrous N,N- dimethylformamide (25 mL) was added 1,1'-carbonyldiimidazole (73 mg, 0.45 mmol) and the reaction was heated at 75° C. When the carbon dioxide evolution had ceased (after 30 min), the reaction was cooled to room temperature and a solution of (R)-2-amino-8-(4-methylpiperazin-1-yl)-1,2,3,4-tetrahydronaphthalene (100 mg, 0.41 mmol) in anhydrous N,N-dimethylformamide (5 mL) was added. The reaction was allowed to stir at ambient temperature for 24 h and the solvent was evaporated in vacuo. Purification on a silica gel column using chloroform/ethanol saturated with $NH_3$ (100:3) as the eluent gave 58 mg (27% yield) of the title compound as a viscous oil: $[\alpha]^{21}_D$ –370 (c 0.50, chloroform); EIMS (70 eV) m/z (relative intensity) 512 (11, M$^+$).

Example 80

(R)-N-[8-(4-Methylpiperazin-1-yl)-1,2,3,4-tetrahydro-2-naphthyl]phenylacetamide

To an ice-cooled solution of (R)-2-amino-8-(4-methylpiperazin-1-yl)-1,2,3,4-tetrahydronaphthalene (100 mg, 0.43 mmol) and triethylamine (88 μL, 0.64 mmol) in methylene chloride (20 mL) was added dropwise phenylacetyl chloride (70 mg, 0.45 mmol) in methylene chloride (5 mL). After the addition, the reaction was allowed to stir at ambient temperature for 10 min and then washed with water. The phases were separated and the organic phase was dried ($Na_2SO_4$), filtered and evaporated in vacuo to give a crude product which was purified on a silica gel column using chloroform/ethanol saturated with $NH_3$ (100:3) as the eluent. Yield: 95 mg (61%) of the title compound as white crystals: mp 151–152° C; $[\alpha]^{21}_D$ –4.3° (c 1.0, chloroform); EIMS (70 eV) m/z (relative intensity) 363 (21, M$^+$).

Example 81

(R)-N-[8-(4-Methylpiperazin-1-yl)-1,2,3,4-tetrahydro-2-naphthyl]-3-phenylpropionamide To an ice-cooled solution of (R)-2-amino-8-(4-methylpiperazin-1-yl)-1,2,3,4-tetrahydronaphthalene (99 mg, 0.40 mmol) and triethylamine (83 μL, 0.42 mmol) in methylene chloride (20 mL) was added dropwise 3-phenylpropionyl chloride (72 mg, 0.42 mmol) in methylene chloride (5 mL). After the addition, the reaction was allowed to stir at ambient temperature for 15 min and then washed with water. The phases were separated and the organic phase was dried ($Na_2SO_4$), filtered and evaporated in vacuo to give a crude product which was purified on a silica gel column using chloroform/ethanol saturated with $NH_3$ (100:4) as the eluent. Yield: 120 mg (61%) of the title compound as white crystals: mp 184–186° C.; $[\alpha]^{21}_D$ +6.5° (c 1.0, chloroform); EIMS (70 eV) m/z (relative intensity) 374 (54, M$^+$).

Example 82

(R)-N-[8-(4-Methylpiperazin-1-yl)-1,2,3,4-tetrahydro-2-naphthyl]-4-phenylbutanamide 4-Phenylbutyric acid (1.0 g, 6.1 mmol) was dissolved in thionyl chloride (15 mL) and heated at reflux for 1 h. The excess of thionyl chloride was evaporated in vacuo, the residue was treated with toluene and again the solvent was removed in vacuo. Crude acid chloride (86 mg, 0.47 mmol) was dissolved in methylene chloride (5 mL) and added dropwise to an ice-cooled solution of (R)-2-amino-8-(4-methylpiperazin-1-yl)-1,2,3,4-tetrahydronaphthalene (110 mg, 0.45 mmol) and triethylamine (93 μL, 0.68 mmol) in methylene chloride (15 mL). After the addition, the reaction was allowed to stir at ambient temperature for 15 min and was then washed with water. The phases were separated and the organic phase was dried ($Na_2SO_4$), filtered and evaporated in vacuo to give a crude product which was purified on a silica gel column using chloroform/ethanol saturated with $NH_3$ (100:4) as the eluent. Yield: 150 mg (82%) of the title compound as white crystals: mp 137–139° C.; $[\alpha]^{21}_D$ +8.4° (c 0.50, chloroform); EIMS (70 eV) m/z (relative intensity) 391 (23, M$^+$).

Example 83

(R)-N-[8-(4-Methylpiperazin-1-yl)-1,2,3,4-tetrahydro-2-naphthyl]-5-phenylpentanamide 5-Phenylvaleric acid (1.0 g, 5.6 mmol) was dissolved in thionyl chloride (15 mL) and heated at reflux for 1 h. The excess of thionyl chloride was evaporated in vacuo, the residue was treated with toluene and again the solvent was removed in vacuo. Crude acid chloride (93 mg, 0.47 mmol) was dissolved in methylene chloride (5 mL) and added dropwise to an ice-cooled solution of (R)-2-amino-8-(4-methylpiperazin-1-yl)-1,2,3,4-tetrahydronaphthalene (110 mg, 0.45 mmol) and triethylamine (93 μL, 0.68 mmol) in methylene chloride (15 mL). After the addition, the reaction was allowed to stir at ambient temperature for 15 min and was then washed with water. The phases were separated and the organic phase was dried ($Na_2SO_4$), filtered and evaporated in vacuo to give a crude product which was purified on a silica gel column using chloroform/ethanol saturated with $NH_3$ (100:4) as the eluent. Yield: 120 mg (66%) of the title compound as viscous oil: $[\alpha]^{21}_D$ +7.4° (c 0.50, chloroform); EIMS (70 eV) m/z (relative intensity) 405 (11, M$^+$).

Example 84

(R)-N-[8-(4-Methylpiperazin-1-yl)-1,2,3,4-tetrahydro-2-naphthyl]-4-(4-ethylphenyl)benzamide 4'-Ethyl-4-biphenylcarboxylic acid (1.0 g, 4.4 mmol) was dissolved in thionyl chloride (15 mL) and heated at reflux for 1 h. The excess of thionyl chloride was evaporated in vacuo, the residue was treated with toluene and again the solvent was removed in vacuo. Crude acid chloride (130 mg, 0.53 mmol) was dissolved in methylene chloride (5 mL) and added dropwise to an ice-cooled solution of (R)-2-amino-8-(4-methylpiperazin-1-yl)-1,2,3,4-tetrahydronaphthalene (120 mg, 0.48 mmol) and triethylamine (99 μL, 0.72 mmol) in methylene chloride (20 mL). After the addition, the reaction was allowed to stir at ambient temperature for 15 min and was then washed with water. The phases were separated and the organic phase was dried ($Na_2SO_4$), filtered and evaporated in vacuo to give a crude product which was purified on a silica gel column using chloroform/ethanol saturated with $NH_3$ (100:4) as the eluent. Yield: 140 mg (53%) of the title compound as white crystals: mp 234–235° C.; $[\alpha]^{21}_D$ –73° (c 1.0, chloroform); EIMS (70 eV) m/z (relative intensity) 453 (10, M$^+$)

Example 85

(R)-N-[8-(4-Methylpiperazin-1-yl)-1,2,3,4-tetrahydro-2-naphthyl]-4-(4-hydroxyphenyl)benzamide 4'-Hydroxy-4-biphenylcarboxylic acid (0.40 g, 1.9 mmol) was dissolved in thionyl chloride (10 mL) and heated at reflux for 1 h. The excess of thionyl chloride was evaporated in vacuo, the residue was treated with toluene and again the solvent was removed in vacuo. Crude acid chloride (120 mg, 0.51 mmol) was dissolved in methylene chloride (5 mL) and added dropwise to an ice-cooled solution of (R)-2-amino-8-(4-methylpiperazin-1-yl)-1,2,3,4-tetrahydronaphthalene (120 mg, 0.49 mmol) and triethylamine (100 µL, 0.74 mmol) in methylene chloride (20 mL) . After the addition the reaction was allowed to stir at ambient temperature for 15 min and was then washed with water. The phases were separated and the organic phase was dried ($Na_2SO_4$), filtered and evaporated in vacuo to give a crude product which was purified on a silica gel column using chloroform/methanol/concentrated ammonium hydroxide (95:6:0.5) as the eluent. Yield: 95 mg (44%) of the title compound as white crystals: mp 261–262° C.; EIMS (70 eV) m/z (relative intensity) 441 (2, $M^+$)

Example 86

(R)-N-[8-(4-Methylpiperazin-1-yl)-1,2,3,4-tetrahydro-2-naphthyl]-3-trifluoromethylbenzamide To an ice-cooled solution of (R)-2-amino-8-(4-methylpiperazin-1-yl)-1,2,3,4-tetrahydronaphthalene (100 mg, 0.42 mmol) and triethylamine (88 µL, 0.63 mmol) in methylene chloride (15 mL) was added dropwise 3-(trifluoromethyl)benzoyl chloride (93 mg, 0.44 mmol) in methylene chloride (5 mL). After the addition, the reaction was allowed to stir at ambient temperature for 15 min and was then washed with water. The phases were separated and the organic phase was dried ($Na_2SO_4$), filtered and evaporated in vacuo to give a crude product which was purified on a silica gel column using chloroform/ethanol saturated with $NH_3$ (100:4) as the eluent. Yield: 130 mg (71%) of the title compound as a viscous oil: $[\alpha]^{21}_D$ –25° (c 1.0, chloroform); EIMS (70 eV) m/z (relative intensity) 417 (25, $M^+$).

Example 87

(R)-N-[8-(4-Methylpiperazin-1-yl)-1,2,3,4-tetrahydro-2-naphthyl]-3-phenoxybenzamide 3-Phenoxybenzoic acid (1.0 g, 4.7 mmol) was dissolved in thionyl chloride (15 mL) and heated at reflux for 1 h. The excess of thionyl chloride was evaporated in vacuo, the residue was treated with toluene and again the solvent was removed in vacuo. Crude acid chloride (99 mg, 0.42 mmol) was dissolved in methylene chloride (5 mL) and added dropwise to an ice-cooled solution of (R)-2-amino-8-(4-methylpiperazin-1-yl)-1,2,3,4-tetrahydronaphthalene (99 mg, 0.41 mmol) and triethylamine (83 µL, 0.42 mmol) in methylene chloride (20 mL). After the addition, the reaction was allowed to stir at ambient temperature for 15 min and was then washed with water. The phases were separated and the organic phase was dried ($Na_2SO_4$), filtered and evaporated in vacuo to give a crude product which was purified on a silica gel column using chloroform/ethanol saturated with $NH_3$ (100:3) as the eluent. Yield: 120 mg (68%) of the title compound as an oil. The oil crystallized from diethyl ether/hexane: mp 136–137° C.; $[\alpha]^{21}_D$ –9.0° (c 1.0, chloroform); EIMS (70 eV) m/z (relative intensity) 441 (31, $M^+$).

Example 88

(R)-N-[8-(4-Methylpiperazin-1-yl)-1,2,3,4-tetrahydro-2-naphthyl]-3-hydroxybenzamide A solution of 3-acetoxybenzoic acid (130 g, 0.69 mol) in thionyl chloride (400 mL) was stirred at ambient temperature for 4 days. The excess of thionyl chloride was evaporated in vacuo, the residue was treated with toluene and again the solvent was removed in vacuo. Crude acid chloride (100 mg, 0.52 mmol) was dissolved in methylene chloride (5 mL) and added dropwise to an ice-cooled solution of (R)-2-amino-8-(4-methylpiperazin-1-yl)-1,2,3,4-tetrahydronaphthalene (120 mg, 0.50 mmol) and triethylamine (100 µL, 0.75 mmol) in methylene chloride (20 mL). After the addition, the reaction was allowed to stir at ambient temperature for 15 min and was then washed with dilute aqueous sodium hydrogen carbonate. The phases were separated and the organic phase was dried ($Na_2SO_4$), filtered and evaporated in vacuo. The residue was dissolved in 99.5% ethanol (25 mL) and concentrated hydrochloric acid (5 mL) was added. After 17 h, the pH was adjusted to 8 and the solvent evaporated in vacuo. The residue was partitioned between water and methylene chloride. The organic phase was separated, dried ($Na_2SO_4$), filtered and evaporated in vacuo to give a crude product which was purified on a silica gel column using chloroform/ethanol saturated with $NH_3$ (100:4) as the eluent. Yield: 93 mg (51%) of the title compound as white crystals: mp 117° C. decomp., $[\alpha]^{21}_D$ –10° (c 1.0, chloroform); EIMS (70 eV) m/z (relative intensity) 365 (22, $M^+$).

Example 89

(R)-N-8-(4-Methylpiperazin-1-yl)-1,2,3,4-tetrahydro-2-naphthyl]-3-methylsulfonyloxybenzamide A suspension of 3-methanesulfonyloxybenzoic acid (0.20 g, 0.90 mmol; described in: Looker, J. H.; Hayes, C. H.; Thatcher, D. N. *J. Am. Chem. Soc.* 1957, 79, 741–4) in thionyl chloride (5 mL) was heated at 40° C. for 45 min (the solution became homogeneous). The excess of thionyl chloride was evaporated in vacuo, the residue was treated with toluene and again the solvent was removed in vacuo. Crude acid chloride (120 mg, 0.50 mmol) was dissolved in methylene chloride (5 mL) and added dropwise to an ice-cooled solution of (R)-2-amino-8-(4-methylpiperazin-1-yl)-1,2,3,4-tetrahydronaphthalene (120 mg, 0.48 mmol) and triethylamine (100 µL, 0.72 mmol) in methylene chloride (20 mL). After the addition, the reaction was allowed to stir at ambient temperature for 15 min and was then washed with dilute aqueous sodium hydrogen carbonate. The phases were separated and the organic phase was dried ($Na_2SO_4$), filtered and evaporated in vacuo to give a crude product which was purified on a silica gel column using chloroform/ethanol saturated with $NH_3$ (100:4) as the eluent. Yield: 87 mg (41%) of the title compound as white crystals: mp 159–160° C.; $[\alpha]^{21}_D$ –27° (c 1.0, chloroform); EIMS (70 eV) m/z (relative intensity) 443 (21, $M^+$).

Example 90

(R)-N-[8-(4-Methylpiperazin-1-yl)-1,2,3,4-tetrahydro-2-naphthyl]-2-methylbenzamide To an ice-cooled solution of (R)-2-amino-8-(4-methylpiperazin-1-yl)-1,2,3,4-tetrahydronaphthalene (100 mg, 0.41 mmol) and triethylamine (85 µL, 0.62 mmol) in methylene chloride (15 mL) was added dropwise 2-methylbenzoyl chloride (66 mg, 0.43 mmol) in methylene chloride (5 mL). After the addition, the reaction was allowed to stir at ambient temperature for 15 min and was then washed with water. The phases were separated and the organic phase was dried ($Na_2SO_4$), filtered and evaporated in vacuo to give a crude product which was purified on a silica gel column using chloroform/ethanol saturated with NH$_3$ (100:3.5) as the eluent. Yield: 100 mg (80%) of the title compound as white crystals: mp 179–180° C.; $[\alpha]^{21}_D$ –22° (c 1.0, chloroform); EIMS (70 eV) m/z (relative intensity) 363 (21, M$^+$).

Example 91

(R)-N-[8-(4-Methylpiperazin-1-yl)-1,2,3,4-tetrahydro-2-naphthyl]-2-ethoxybenzamide To an ice-cooled solution of (R)-2-amino-8-(4-methylpiperazin-1-yl)-1,2,3,4-tetrahydronaphthalene (110 mg, 0.43 mmol) and triethylamine (90 µL, 0.65 mmol) in methylene chloride (15 mL) was added dropwise 2-ethoxybenzoyl chloride (84 mg, 0.45 mmol) in methylene chloride (5 mL). After the addition, the reaction was allowed to stir at ambient temperature for 15 min and was then washed with water. The phases were separated and the organic phase was dried (Na$_2$SO$_4$), filtered and evaporated in vacuo to give a crude product which was purified on a silica gel column using chloroform/ethanol saturated with NH$_3$ (100:3) as the eluent. Yield: 110 mg (64%) of the title compound as white solid: $[\alpha]^{21}_D$ –36° (c 1.0, chloroform); EIMS (70 eV) m/z (relative intensity) 393 (15, M$^+$). The hydrochloride salt was precipitated out of diethyl ether and 110 mg (59% yield) of white crystals were isolated; mp sinters at 176° C.

Example 92

(R)-N-[8-(4-Methylpiperazin-1-yl)-1,2,3,4-tetrahydro-2-naphthyl]-2-hydroxybenzamide To an ice-cooled solution of (R)-2-amino-8-(4-methylpiperazin-1-yl)-1,2,3,4-tetrahydronaphthalene (180 mg, 0.74 mmol) and triethylamine (150 µL, 1.1 mmol) in methylene chloride (20 mL) was added dropwise acetylsalicyloyl chloride (160 mg, 0.78 mmol) in methylene chloride (10 mL). After the addition, the reaction was allowed to stir at ambient temperature for 15 min and was then washed with dilute aqueous sodium hydrogen carbonate. The phases were separated and the organic phase was dried (Na$_2$SO$_4$), filtered and evaporated in vacuo. The residue was dissolved in 99.5% ethanol (25 mL) and concentrated hydrochloric acid (3 mL) was added. After 17 h, the pH was adjusted to 8 and the solvent was evaporated in vacuo. The residue was partitioned between water and methylene chloride. The organic phase was separated, dried (Na$_2$SO$_4$), filtered and evaporated in vacuo to give a crude product which was purified on a silica gel column using chloroform/ethanol saturated with NH$_3$ (100:3) as the eluent. Yield: 170 mg (63%) of the title compound as white crystals: mp 87° C. decomp; $[\alpha]^{21}_D$ –18° (c 1.0, chloroform); EIMS (70 eV) m/z (relative intensity) 365 (33, M$^+$).

Example 93

(R)-N-[8-(4-Methylpiperazin-1-yl)-1,2,3,4-tetrahydro-2-naphthyl]-2-methylsulfonyloxybenzamide A solution of 2-methanesulfonyloxybenzoic acid (0.30 g, 1.4 mmol; described in: Looker, J. H.; Hayes, C. H.; Thatcher, D. N. *J. Am. Chem. Soc.* 1957, 79, 741–4) in thionyl chloride (10 mL) was heated at 40° C. for 45 min. The excess of thionyl chloride was evaporated in vacuo, the residue was treated with toluene and again the solvent was removed in vacuo. Crude acid chloride (120 mg, 0.49 mmol) was dissolved in methylene chloride (5 mL) and added dropwise to an ice-cooled solution of (R)-2-amino-8-(4-methylpiperazin-1-yl)-1,2,3,4-tetrahydronaphthalene (120 mg, 0.47 mmol) and triethylarmine (98 µL, 0.72 mmol) in methylene chloride (20 mL). After the addition, the reaction was allowed to stir at ambient temperature for 15 min and was then washed with dilute aqueous sodium hydrogen carbonate. The phases were separated and the combined organic phases were dried (Na$_2$SO$_4$), filtered and evaporated in vacuo to give a crude product which was purified on a silica gel column using chloroform/ethanol saturated with NH$_3$ (100:3) as the eluent. Yield: 110 mg (55%) of the title compound as white crystals: mp 144–145° C.; $[\alpha]^{21}_D$ –7.1° (c 1.0, chloroform); EIMS (70 eV) m/z (relative intensity) 443 (10, M$^+$).

Example 94

(R)-2-Amino-8-bromo-5-methoxy-1,2,3,4-tetrahydronaphthalene (R)-2-Amino-5-methoxy-1,2,3,4-tetrahydronaphthalene hydrochloride (5.0 g, 23 mmol) was dissolved in acetic acid (300 mL) under nitrogen atmosphere. Sodium acetate (5.5 g, 70 mmol) was added and bromine (3.5 g, 23 mmol) was then added in one portion. The mixture was stirred for 5 minutes at room temperature. The solvent was removed in vacuo to give a solid residue which was partitioned between ethyl acetate and NaOH (2 M). The layers were separated and the aqueous phase was extracted twice with ethyl acetate. The organic layers were combined and dried (Na$_2$SO$_4$). The solvent was removed in vacuo to give a brown oily residue. The HCl salt was precipitated from diethyl etherimethylene chloride by the addition of HCl in diethyl ether (3 M): yield 7.7 g (94%). Recrystallization from methanol gave the title compound as needle crystals: mp 264–265° C.; $[\alpha]^{21}_D$ +54° (c 1, MeOH); EIMS (70 eV) m/z (relative intensity) 257 (30, M$^+$, $^{81}$Br), 255 (31, M$^+$, $^{79}$Br).

Example 95

(R)-8-Bromo-2-N,N-dibenzylamino-5-methoxy-1,2,3,4-tetrahydronaphthalene (R)-2-Amino-8-bromo-5-methoxy-1,2,3,4-tetrahydronaphthalene (4.5 g, 17.5 mmol), benzyl bromide (6.6 g, 38 mmol), potassium carbonate (9.7 g, 70 mmol) and potassium iodide (100 mg, catalytic amount) were mixed with acetonitrile (250 mL) under nitrogen atmosphere and refluxed for 18 h. The solvent was removed in vacuo and the residue was partitioned between ethyl acetate and ammonia (2 M). The layers were separated and the organic layer was dried (MgSO$_4$). The solvent was removed in vacuo to give a residue which was purified by flash chromatography on silica gel using hexane/methylene chloride 8:2 as the eluent. The title compound was obtained as an oil. Yield 7.5 g (98% ): $[\alpha]^{21}_D$ +87° (c 1, MeOH); EIMS (70 eV) m/z (relative intensity) 437 (12, M$^+$,$^{81}$Br), 435 (13, M$^+$,$^{79}$Br).

Example 96

(R)-2-N,N-Dibenzylamino-8-(1-methylpiperidin-4-yl)-5-trifluoromethanesulfonyloxy-1,2,3,4-tetrahydronaphthalene (R)-8-Bromo-2-N,N-dibenzylamino-5-methoxy-1,2,3,4-tetrahydronaphthalene (6.8 g, 16 mmol) was dissolved in anhydrous tetrahydrofuran (100 mL) under nitrogen atmosphere. The solution was cooled to −78° C. before n-butyllithium (11.7 mL, 1.6 M, 19 mmol) was added dropwise during 3 minutes. The mixture was stirred for 5 minutes and N-methyl-4-piperidone (5.4 g, 48 mmol) was added during 3 minutes. The cooling bath was removed and the temperature was allowed to rise to 0° C. before the reaction was quenched by the addition of water. The layers were separated and the organic layer was dried (MgSO$_4$). The solvent was removed in vacuo to give a residue which was purified by crystallization (ethyl acetateihexane) EIMS (70 ev) m/z (relative intensity) 470 (2, M$^+$). The crystals were dissolved in tetrahydrofuran under nitrogen atmosphere. Sodium borohydride (5.9 g, 0.16 mol) was added and the mixture was cooled to 0° C. Trifluoroacetic acid (10 mL) was added dropwise during 1 h. The cooling bath was removed and the mixture was stirred for 1 h at room temperature before it was carefully poured into a NaOH solution (40%-ig) and diluted with water and diethyl ether. The layers were separated and the organic layer was dried (MgSO$_4$). The solvent was removed in vacuo to give a solid residue [EIMS (70 ev) m/z (relative intensity) 454 (12, M$^+$)] which was suspended in hydrobromic acid (48%, 200 mL) and refluxed (everything dissolved) for 2 h. The mixture was allowed to attain room temperature. The formed crystals were filtered and partitioned between ethyl acetate and ammonia (2 M). The layers were separated and the organic layer was dried (MgSO$_4$). The solvent was removed in vacuo to give a solid residue [EIMS (70 ev) m/z (relative intensity) 440 (5, M$^+$)] which was suspended in methylene chloride (150 mL). 2,4,6-Collidine (2 g, 16 mmol) was added and the mixture was cooled to −78° C. Trifluoromethanesulfonic anhydride (4.4 g, 15 mmol) was added during 5 minutes. The cooling bath was removed and the temperature of the reaction mixture was allowed to rise to −5° C. The reaction mixture was washed with ammonia (2 M) and dried (MgSO$_4$). The solvent was removed in vacuo to give a solid residue which was purified by flash chromatography on silica gel using methylene chloride/ethanol 10:1, containing 0.5% of ammonia, as the eluent. The title compound was obtained as an oil. Yield 4 g (44%): [α]$^{21}_D$ +45° (c 1, CHCl$_3$); EIMS (70 ev) m/z (relative intensity) 572 (2, M$^+$), Example 97

(R)-2-N,N-Dibenzylamino-8-(1-methylpiperidin-4-yl)-1,2,3,4-tetrahydronaphthalene (R) -2-N,N-Dibenzylamino-8-(1-methylpiperidin-4-yl)-5-trifluoromethanesulfonyloxy-1,2,3,4-tetrahydronaphthalene (4 g, 7.0 mmol), triethylamine (2.8 g, 28 mmol), formic acid (1.3 g, 28 mmol), triphenylphosphine (0.4 g, 1.4 mmol) and palladium(II)acetate (85 mg, 0.35 mmol) were dissolved in N,N-dimethylformamide (20 mL) under nitrogen atmosphere. The solution was stirred at 60° C. for 18 h. The solvent was removed in vacuo to give a residue which was partitioned between ethyl acetate and ammonia (2 M). The layers were separated and the organic layer was dried (MgSO$_4$). The solvent was removed in vacuo to give a dark brown oily residue which was purified by flash chromatography on silica gel using chloroform/ethanol 20:1, containing 0.5% of ammonia, as the eluent. The title compound was obtained as an oil. Yield 1.7 g (57%): [α]$^{21}_D$ +53° (c 1, CHCl$_3$); EIMS (70 eV) m/z (relative intensity) 424 (1, M$^+$).

Example 98

(R)-2-Amino-8-(1-methylpiperidin-4-yl)-1,2,3,4-tetrahydronaphthalene (R)-2-N,N-Dibenzylamino-8-(1-methylpiperidin-4-yl)-1,2,3,4-tetrahydronaphthalene (1.7 g, 4.0 mmol), ammonium formate (5.0 g, 80 mmol), palladium (10% on activated carbon, 0.8 g), methanol (30 mL), water (15 mL) and tetrahydrofuran (40 mL) were mixed under nitrogen atmosphere and refluxed for 3 h (fitted with an outlet for the excess of hydrogen gas). The catalyst was filtered off and washed thoroughly with ethanol. The solvent was removed in vacuo until ca 30 mL was left. The residue was partitioned between ethyl acetate and NaOH (2 M). The layers were separated and the aqueous phase was extracted twice with ethyl acetate. The organic layers were combined and the solvent was removed in vacuo to give 0.8 g of the title compound as an oil (82% yield): [α]$^{21}_D$ +36° (c 0.5, CHCl$_3$); EIMS (70 eV) m/z (relative intensity) 244 (1, M$^+$).

Example 99

(R)-N-[8-(1-Methylpiperidine-4yl)-1,2,3,4-tetrahydro-2-naphthyl]-4-trifluoromethylbenzamide α,α,α-Trifluoro-p-toluic acid (0.15 g, 0.8 mmol) was suspended in thionyl chloride (3 mL) and refluxed for 30 minutes (everything dissolved after a few minutes). The excess of thionyl chloride was removed in vacuo with toluene. The residue was dissolved in methylene chloride (5 mL) and added dropwise to an ice cold solution of (R)-2-amino-8-(1-methylpiperidin-4-yl)-1,2,3,4-tetrahydronaphthalene (0.15 g, 0.6 mmol) and triethylamine (92 mg, 0.9 mmol) in methylene chloride (5 mL). The mixture was stirred for 15 minutes and was then diluted with ethyl acetate, washed with ammonia (2 M) and dried (MgSO$_4$). The solvent was removed in vacuo. The residue was purified by flash chromatography on silica gel using methylene chloride/ethanol 5:1, containing 0.5% of ammonia, as the eluent. The title compound was obtained as off-white crystals. Yield 140 mg (55%): mp 163–166° C.; [α]$^{21}_D$ +36° (c 0.5, CHCl$_3$); EIMS (70 eV) m/z (relative intensity) 416 (48, M$^+$).

Example 100

(R)-N-[8-(1-Methylpiperidin-4-yl)-1,2,3,4-tetrahydro-2-naphthyl]-4-butoxybenzamide 4-Butoxybenzoic acid (0.16 g, 0.8 mmol) was dissolved in thionyl chloride (3 mL) and refluxed for 30 minutes. The excess of thionyl chloride was removed in vacuo with toluene. The residue was dissolved in methylene chloride (5 mL) and added dropwise to an ice cold solution of (R)-2-amino-8-(1-methylpiperidin-4-yl)-1,2,3,4-tetrahydronaphthalene (0.15 g, 0.6 mmol) and triethylamine (92 mg, 0.9 mmol) in methylene chloride (5 mL). The mixture was stirred for 30 minutes and was then diluted with ethyl acetate, washed with ammonia (2 M) and dried (MgSO$_4$). The solvent was removed in vacuo. The residue was purified by flash chromatography on silica gel using methylene chloride/ethanol 5:1, containing 0.5% of ammonia, as the eluent. The title compound was obtained as white crystals. Yield 170 mg (50%): mp 162–164° C.; [α]$^{21}_D$ −2° (c 0.5, CHCl$_3$); EIMS (70 eV) m/z (relative intensity) 420 (40, M$^+$).

Example 101

(R)-N-[8-(1-Methylpiperidin-4-yl)-1,2,3,4-tetrahydro-2-naphthyl]-4-morpholinobenzamide 4-N-Morpholinobenzoic acid (0.4 g, 1.6 mmol) was dissolved in thionyl chloride (3 mL) under nitrogen atmosphere and stirred at room temperature for 5 minutes. The excess of thionyl chloride was removed in vacuo to give a light yellow residue. The residue was dissolved in methylene chloride (10 ml) and added dropwise to a solution of (R)-2-amino-8-(1-methylpiperidin-4-yl)-1,2,3,4-tetrahydronaphthalene (0.4 g, 1.9 mmol) and triethylamine (0.4 g, 4.0 mmol) in methylene chloride (10 mL) during 5 minutes. The mixture was stirred at room temperature for 15 minutes before washed with 2 M ammonia and dried (MgSO$_4$). The solvent was removed in vacuo to give a residue which was purified by flash chromatography on silica gel using methylene chloride/ethanol, 5:1 containing 0.5% of ammonia. Yield 100 mg (12%): mp 196–198° C.; $[\alpha]^{21}_D$ –19° (c 1, CHCl$_3$); EIMS (70 eV) m/z (relative intensity) 433 (27, M$^+$).

Example 102

(R)-2-N,N-Dibenzylamino-5-methoxy-1,2,3,4-tetrahydronaphthalene

To a solution of (R)-5-methoxy-2-amino-1,2,3,4-tetrahydronaphthalene hydrochloride (30 g, 0.14 mol) in acetonitrile (600 mL) were added potassium carbonate (68 g, 0.49 mol), potassium iodide (catalytic amount) and benzyl bromide (42 mL, 0.35 mol). The reaction mixture was stirred at reflux for a period of 48 h.

After the precipitate was filtered off and the acetonitrile removed in vacuo, the residue was partitioned between diethyl ether and water. The organic phase was separated, dried (Na$_2$SO$_4$) and evaporated in vacuo to give a crude product which was purified on a silica gel column using hexane/ethyl acetate, (3:1) as the eluent. Yield: 46 g (92%) of the title compound as white crystals: mp 112–114° C.; $[\alpha]^{21}_D$ +61° (c 1.0, chloroform); EIMS (70 eV) m/z (relative intensity) 357 (38, M$^+$).

Example 103

(S)-2-N,N-Dibenzylamino-5-methoxy-1,2,3,4-tetrahydronaphthalene

The title compound was synthesized according to the procedure of Example 102 using the (S)-form: mp 113–115° C.; $[\alpha]^{21}_D$ –59° (c 1.0, chloroform); EIMS (70 eV) m/z (relative intensity) 357 (74, M$^+$).

Example 104

(R)-6-N,N-Dibenzylamino-5,6,7,8-tetrahydro-1-naphthol (R)-2-N,N-Dibenzylamino-5-methoxy-1,2,3,4-tetrahydronaphthalene (46 g, 0.13 mol) was dissolved in diethyl ether (900 mL) and an excess of an ethereal HCl solution was added dropwise. The precipitate was filtered and dried in vacuo to give a white solid. This crude product (45 g, 0.11 mol) was dissolved in anhydrous methylene chloride (500 mL) and cooled to –60° C. To the solution was boron tribromide (14 mL, 0.15 mol), dissolved in anhydrous methylene chloride (50 mL), added dropwise. The reaction temperature was allowed to reach –5° C. and was kept there overnight.

To the ice-cooled solution was a 2 M aqueous ammonium hydroxide solution added dropwise and the mixture was extracted, twice, with methylene chloride. The combined organic phases were dried (Na$_2$SO$_4$), filtered and the solvent was removed in vacuo to give the crude residue. Chromatography on silica (eluent: methylene chloride) gave 33 g (83% yield) of the title compound as a viscous clear oil: $[\alpha]^{21}_D$ +72° (c 0.66, chloroform); EIMS (70 eV) m/z (relative intensity) 343 (11, M$^+$).

Example 105

(S)-6-N,N-Dibenzylamino-5,6,7,8-tetrahydro-1-naphthol

The title compound was synthesized according to the procedure of Example 104 using the (S)-form: $[\alpha]^{21}_D$ '71° (c 0.71, chloroform); EIMS (70 eV) m/z (relative intensity) 343 (12, M$^+$).

Example 106

(R)-2-(6-N,N-Dibenzylamino-5,6,7,8-tetrahydro-1-naphthyloxy)-2-methylpropanamide (R)-6-N,N-Dibenzylamino-5,6,7,8-tetrahydro-1-naphthol (28 g, 81 mmol) was stirred in anhydrous dioxane (500 mL) with sodium hydride (60–65% in oil, 2.2 g, 90 mmol) for 1 h. 2-Bromo-2-methylpropanamide (15 g, 90 mmol; described in: Coutts, I. G. C.; Southcott, M. R. *J. Chem. Soc. Perkin Trans.* 1 1990, 767–770) was added and the reaction mixture was heated at 80° C. for 2.5 h. After cooling, the precipitated sodium bromide was filtered off, the filtrate evaporated in vacuo and the residue was partitioned between water and methylene chloride. The organic phase was separated, dried (Na$_2$SO$_4$), filtered and evaporated in vacuo to give the title compound as a viscous oil. Yield: 24 g (70% yield). This crude product was used directly in the next step without further purification. An analytical sample (0.50 g) was purified on a silica gel column using hexane/ethyl acetate (3:1) as the eluent. Yield: 0.46 g of the title compound as a viscous oil: $[\alpha]^{21}_D$ +42° (c 1.0, chloroform); EIMS (70 eV) m/z (relative intensity) 428 (1, M$^+$).

Example 107

(S)-2-(6-N,N-Dibenzylamino-5,6,7,8-tetrahydro-1-naphthyloxy)-2-methylpropanamide The title compound was synthesized according to the procedure of Example 106 using the (S)-form: $[\alpha]^{21}_D$ –42° (c 1.0, chloroform); EIMS (70 eV) m/z (relative intensity) 428 (8, M$^+$).

Example 108

(R)-N-(6-N,N-Dibenzylamino-5,6,7,8-tetrahydro-1-naphthyl)-2-hydroxy-2-methylpropanamide To a solution of (R)-2-(6-N,N-dibenzylamino-5,6,7,8-tetrahydro-1-naphthyloxy)-2-methylpropanamide (23 g, 54 mmol) in anhydrous 1,3-dimethyl-3,4,5,6-tetrahydro-2(1H)-pyrimidone (10 mL) and dry N,N-dimethylformamide (250 mL) was added sodium hydride (60–65% in oil, 5.4 g, 135 mmol) and the reaction was heated at 130° C. for 10 h. An additional amount of anhydrous 1,3-dimethyl-3,4,5,6-tetrahydro-2(1H)-pyrimidone (15 mL) and sodium hydride (0.5 mol equiv.) was added and the reaction was heated at 130° C. for in total 21 h. The solution was poured into a mixture of ice and water and extracted three times with ethyl acetate. The combined organic phases were dried (Na$_2$SO$_4$), filtered and evaporated in vacuo to give the title compound as a viscous oil. Yield: 20 g (86% yield). This crude product was used directly in the next step without further purification. An analytical sample (0.50 g) was purified on a silica gel column using hexane/ethyl acetate (5:1) as the eluent. Yield: 0.24 g of the title compound as a viscous oil: $[\alpha]^{21}_D$ +35° (c 1.0, chloroform); EIMS (70 eV) m/z (relative intensity) 428 (1, M$^+$).

Example 109

(S)-N-(6-N,N-Dibenzylamino-5,6,7,8-tetrahydro-1-naphthyl)-2-hydroxy-2-methylpropanamide The title compound was synthesized according to the procedure of Example 108 using the (S)-form: $[\alpha]21D$ +33° (c 1.1, chloroform), EIMS (70 eV) m/z (relative intensity) 428 (4, M$^+$).

Example 110

(R)-2-N,N-Dibenzylamino-5-amino-1,2,3,4-tetrahydronaphthalene (R)-N-(6-N,N-Dibenzylamino-5,6,7,8-tetrahydro-1-naphthyl)-2-hydroxy-2-methylpropanamide (19 g, 44 mmol) was dissolved in ethanol (500 mL) and a 20% HCl aqueous solution (500 mL) and heated to reflux for 18 h. The ethanol was evaporated in vacuo and the remaining solution was washed twice with diethyl ether and cooled on ice-bath. After alkalization with a 45% aqueous solution of sodium hydroxide the mixture was extracted with methylene chloride. The combined organic phases were dried ($Na_2SO_4$), filtered and evaporated in vacuo. Purification on a silica gel column using chloroform as the eluent gave 6.1 g (40% yield) of the title compound as a light-brown viscous oil: $[\alpha]^{21}_D$ +54° (c 0.97, chloroform); EIMS (70 eV) m/z (relative intensity) 342 (19, M$^+$).

Example 111

(S)-2-N,N-Dibenzylamino-5-amino-1,2,3,4-tetrahydronaphthalene

The title compound was synthesized according to the procedure of Example 110 using the (S)-form: $[\alpha]^{21}_D$ −53° (c 1.0, chloroform); EIMS (70 eV) m/z (relative intensity) 342 (20, M$^+$).

Example 112

(R)-1-(6-N,N-Dibenzylamino-5,6,7,8-tetrahydro-1-naphthyl)-4-methylpiperazine-2,6-dione 1,1'-Carbonyldiimidazole (5.5 g, 34 mmol) was added to a stirred suspension of methyliminodiacetic acid (2.5 g, 17 mmol) in anhydrous N,N-dimethylformamide (250 mL) The reaction mixture was heated at 80° C. for 1 h. (R)-2-N,N-Dibenzylamino-5-amino-1,2,3,4-tetrahydronaphthalene (5.3 g, 15 mmol) dissolved in anhydrous N,N-dimethylformamide (75 mL) was then added and stirring at 80° C. was continued for 10 h. The solvent was evaporated in vacuo and the crude product was purified on a silica gel column using chloroform/ethanol saturated with $NH_3$ (100:0.5) as the eluent. Yield: 5.0 g (87% yield) as a viscous oil: $[\alpha]^{21}_D$ +51° (c 1.1, chloroform); EIMS (70 eV) m/z (relative intensity) 453 (16, M$^+$).

Example 113

(S)-1-(6-N,N-Dibenzylamino-5,6,7,8-tetrahydro-1-naphthyl)-4-methylpiperazine-2,6-dione The title compound was synthesized according to the procedure of Example 112 using the (S)-form: $[\alpha]^{21}_D$ −50° (c 1.0, chloroform); EIMS (70 eV) m/z (relative intensity) 453 (22, M$^+$).

Example 114

(R)-2-N,N-Dibenzylamino-5-(4-methylpiperazin-1-yl)-1,2,3,4-tetrahydronaphthalene (R)-1-(6-N,N-Dibenzylaaminо-5,6,7,8-tetrahydro-1-naphthyl)-4-methylpiperazine-2,6-dione (4.0 g, 8.8 mmol) was added to a suspension of lithium aluminum hydride (1.7 g, 44 mmol) in anhydrous tetrahydrofuran (125 mL). The reaction mixture was heated at reflux for 5 h. The reaction was quenched by the addition of water (1.7 mL), 15% aqueous sodium hydroxide (1.7 mL) and again water (5.1 ml). The mixture was filtered, dried ($Na_2SO_4$) and evaporated in vacuo. Purification on a silica gel column using chloroform/ethanol saturated with $NH_3$ (100:1) as the eluent gave 1.4 g (38% yield) of the title compound as a viscous oil: $[\alpha]^{21}_D$ +7.0° (c 1.0, chloroform); EIMS (70 eV) m/z (relative intensity) 425 (7, M$^+$).

Example 115

(S)-2-N,N-Dibenzylamino-5-(4-methylpiperazin-1-yl)-1,2,3,4-tetrahydronaphthalene The title compound was synthesized according to the procedure of Example 114 using the (S)-form: $[\alpha]^{21}_D$ −8.0° (c 1.1, chloroform); EIMS (70 eV) m/z (relative intensity) 425 (6, M$^+$).

Example 116

(R)-2-Amino-5-(4-methylpiperazin-1-yl)-1,2,3,4-tetrahydronaphthalene

To a solution of (R)-2-N,N-dibenzylamino-5-(4-methylpiperazin-1-yl)-1,2,3,4-tetrahydronaphthalene (1.3 g, 3.0 mmol) in methanol (70 mL) were added ammonium formate (4.6 g, 73 mmol) and palladium (10%) on activated carbon (0.45 g). The mixture was refluxed for 2 h and the palladium was then filtered off. The solvent was evaporated in vacuo and the residue was purified on a silica gel column using chloroform/methanol/concentrated ammonium hydroxide (95:5:05) as the eluent. Yield: 360 mg (49%) as lightbrown crystals: mp 98–99° C.; $[\alpha]^{21}_D$ +21° (c 1.1, chloroform); EIMS (70 eV) m/z (relative intensity) 245 (41, M$^+$).

Example 117

(S)-2-Amino-5(4-methylpiperazin-1-yl)-1,2,3,4-tetrahydronaphthalene

The title compound was synthesized according to the procedure of Example 116 using the (S)-form: mp 97–98° C.; $[\alpha]^{21}_D$ −21° (c 1.1, chloroform); EIMS (70 eV) m/z (relative intensity) 245 (55, M$^+$).

Example 118

(R)-N-[5-(4-Methylpiperazin-1-yl)-1,2,3,4-tetrahydro-2-naphthyl]-4-morpholinobenzamide To a solution of 4-morpholinobenzoic acid (110 mg, 0.51 mmol) in anhydrous N,N-dimethylformamide (10 mL) was added 1,1'-carbonyldiimidazole (87 mg, 0.54 mmol) and the reaction was heated at 75° C. When the carbon dioxide evolution had ceased (after 30 min), the reaction was cooled to room temperature and a solution of (R)-2-amino-5-(4-methylpiperazin-1-yl)-1,2,3,4-tetrahydronaphthalene (120 mg, 0.49 mmol) in anhydrous N,N-dimethylformamide (5 mL) was added. The reaction was allowed to stir at 70° C. for 18 h and the solvent was evaporated in vacuo. The residue was purified on a silica gel column using chloroform/ethanol saturated with $NH_3$ (100:3) as the eluent. This gave after crystallization from acetonitrile, 65 mg (30% yield) of the title compound as white crystals: mp 127–128° C.; $[\alpha]^{21}_D$ +51° (c 0.50, chloroform); EIMS (70 eV) m/z (relative intensity) 434 (14, M$^+$).

Example 119

(S)-N-[5-(4-Methylpiperazin-1-yl)-1,2,3,4-tetrahydro-2-naphthyl]-4-morpholinobenzamide The title compound was synthesized according to the procedure of Example 118 using the (S)-form: mp 129–131°

C.; [α]²¹$_D$ −52° (c 0.50, chloroform); EIMS (70 eV) m/z (relative intensity) 434 (8, M⁺).

Example 120

(R)-N-[5-(4-Methylpiperazin-1-yl)-1,2,3,4-tetrahydro-2-naphthyl]-3-phenoxybenzamide 3-Phenoxybenzoic acid (1.0 g, 4.7 mmol) was dissolved in thionyl chloride (15 mL) and heated at reflux for 30 min. The excess of thionyl chloride was evaporated in vacuo, the residue was treated with toluene and again the solvent was removed in vacuo. Crude acid chloride (70 mg, 0.30 mmol) was dissolved in methylene chloride (5 mL) and added dropwise to an ice-cooled solution of (R)-2-amino-5-(4-methylpiperazin-1-yl)-1,2,3,4-tetrahydronaphthalene (70 mg, 0.28 mmol) and triethylamine (55 μL, 0.42 mmol) in methylene chloride (25 mL). After the addition, the reaction was allowed to stir at ambient temperature for 15 min and was then washed with dilute aqueous sodium hydrogen carbonate. The phases were separated and the organic phase was dried (Na$_2$SO$_4$), filtered and evaporated in vacuo to give a crude product which was purified on a silica gel column using chloroform/ethanol saturated with NH$_3$ (100:3) as the eluent. Yield: 45 mg (36%) of the title compound as a solid foam: [α]²¹$_D$ +24° (c 1.0, chloroform); EIMS (70 eV) m/z (relative intensity) 441 (18, M⁺).

Example 121

(S)-N-[5-(4-Methylpiperazin-1-yl)-1,2,3,4-tetrahydro-2-naphthyl]-3-phenoxybenzamide The title compound was synthesized according to the procedure of Example 120 using the (S)-form: [α]²¹$_D$ −23° (c 1.0, chloroform); EIMS (70 eV) m/z (relative intensity) 441 (20, M⁺).

Example 122

(R)-N-Methyl-N-[8-(4-methylpiperazin-1-yl)-1,2,3,4-tetrahydro-2-naphthyl]-4-trifluoromethylbenzamide To an ice-cooled solution (R)-2-N-methylamino-8-(4-methylpiperazin-1-yl)-1,2,3,4-tetrahydronaphthalene (100 mg, 0.39 mmol) and triethylamine (80 μL, 0.58 mmol) in methylene chloride (25 mL) was 4-(trifluoromethyl)benzoyl chloride (90 mg, 0.43 mmol) in methylene chloride (5 mL) added dropwise. After the addition the reaction was allowed to stir at ambient temperature for 15 min and was then washed with diluted aqueous sodium hydrogen carbonate. The phases were separated and the organic phase was dried (Na$_2$SO$_4$), filtered and evaporated in vacuo to give a crude product which was purified on a silica gel column using chloroform/ethanol saturated with NH$_3$ (100:2) as the eluent. Yield: 89 mg (53%) of the title compound as a colourless crystals: mp 123–125° C.; [α]²¹$_D$ +104° (c 1.0, chloroform); EIMS (70 eV) m/z (relative intensity) 431 (13, M⁺).

Example 123

(R)-8-(4-Methylpiperazin-1-yl)-2-[N-(4-trifluoromethyl)benzylamino]-1,2,3,4-tetrahydronaphthalene To a solution of (R)-2-amino-8-(4-methylpiperazin-1-yl)-1,2,3,4-tetrahydronaphthalene (200 mg, 0.81 mmol) in acetonitrile (35 mL) were added potassium carbonate (169 mg, 1.2 mmol), potassium iodide (catalytic amount) and 4-(trifluoromethyl)benzyl bromide (194 mg, 0.81 mmol). The reaction mixture was stirred at reflux for a period of 8 h. after the precipitate was filtered off and the acetonitrile removed in vacuo, the residue was purified on a silica gel column using chloroform/methanol/concentrated ammonium hydroxide (95:5:0.5) as the eluent. Yield: 72 mg (22%) of the title compound as a colourless oil: [α]²¹$_D$ +12° (c 1.0, chloroform); EIMS (70 eV) m/z (relative intensity) 403 (1, M⁺).⁺). The oxalate salt was precipitated out of diethyl ether and light brown crystals were isolated. Yield: 81 mg (17%): mp 95° C., sinters.

Example 124

4-Thiomorpholinobenzoic Acid

To a solution of 4-thiomorpolinobenzonitrile (1 g, 4.9 mmol; described in: Beach, S. F.; Hepworth, J. D.; Sawyer, J.; Hallas, G.; Marsden, R.; Mitchell, M. M.; Ibbitson, D. A.; Jones, A. M.; Neal, G. T. *J. Chem. Soc. Perkin Trans. II*, 1984, 217–221) in glacial acetic acid (20 mL) was added a 20% aqueous hydrochloric acid solution (20 mL) and the reaction was heated at reflux for 15 h. The acetic acid was evaporated in vacuo and the remaining water solution was alkalized with 2 M aqueous sodium hydroxide solution to pH 12. The solution was washed, twice, with diethyl ether and the water phase was adjusted to pH 3 with a 20% aqueous hydrochloric acid solution. The product was filtered off and dried in vacuo to afford 1.0 g (91% yield) of the title compound as white crystals: mp 233–235° C.; EIMS (70 eV) m/z (relative intensity) 223 (50, M⁺).

Example 125

(R)-N-[8-(4-Methylpiperazin-1-yl)-1,2,3,4-tetrahydro-2-naphthyl]-4-thiomorpholinobenzamide 4-Thiomorpholinobenzoic acid (0.25 g, 1.1 mmol) was dissolved in thionyl chloride (25 mL). The excess of thionyl chloride was immediately evaporated in vacuo, the residue was treated with toluene and again the solvent was removed in vacuo. Crude acid chloride (107 mg, 0.44 mmol) was dissolved in methylene chloride (5 mL) and added dropwise to an ice-cooled solution of (R)-2-amino-8-(4-methylpiperazin-1-yl)-1,2,3,4-tetrahydronaphthalene (104 mg, 0.42 mmol) and triethylamine (68 μL, 0.87 mmol) in methylene chloride (35 mL). After the addition the reaction was allowed to stir at ambient temperature for 15 min and then washed with diluted aqueous sodium hydrogen carbonate. The phases were separated and the organic phase was dried (Na$_2$SO$_4$), filtered and evaporated in vacuo to give a crude product which was purified on a silica gel column using chloroform/methanol/concentrated ammonium hydroxide (95:5:0.5) as the eluent. Yield: 58 mg (31%) of the title compound as white crystals: mp 190–191° C.; [α]²¹$_D$ −86° (c 0.25, chloroform); EIMS (70 eV) m/z (relative intensity) 450 (2, M⁺).

Example 126

4-(4-Benzylpiperazin-1-yl)benzonitrile

To a solution of 4-fluorobenzonitrile (3.0 g, 25 mmol) in N,N-dimethylformamide (15 mL) were added 1-benzylpiperazine (4.3 mL, 25 mmol) and potassium carbonate (3.4 g, 25 mmol). The reaction mixture was stirred at 120° C. for 13 h. The solvent was evaporated and the residue was partitioned between ethyl acetate (100 mL) and water (15 mL). The aqueous phase was extracted with ethyl acetate (30 mL) and the combined organic phases were washed twice with brine (10 mL) and dried (MgSO$_4$). Evaporation of the solvent gave 7.6 g of crude product. Purification of the residue on a silica column using ethyl acetate/methylene chloride (1:9) as the eluent afforded 4.0 g (59% yield) of the title compound as a white solid: mp 104–105° C.; EIMS (70 eV) m/z (relative intensity) 277 (20, M$^+$).

Example 127

4-(4-Benzylpiperazin-1-yl)benzoic acid 4-(4-Benzylpiperazin-1-yl) benzonitrile (4.0 g, 15 mmol) was dissolved in glacial acetic acid (40 mL), 6 M hydrochloric acid (50 mL) was added and the reaction mixture was stirred at 100° C. for 17.h. The solvent was evaporated, the residue was suspended in water (10 mL) and the pH was adjusted to 3 by addition of 2 M sodium hydroxide (35 ml). The slurry was stirred at 50° C. for 2 h, cooled and the precipitate was filtered and dried in vacuo to give 4.1 g of a crude product. The solid was partitioned between methylene chloride (40 mL9 nd water (220 mL) with 2 M sodium hydroxide (8 mL). The aqueous phase was washed with methylene chloride (40 mL) and the pH was adjusted to 5 with 2 M hydrochloric acid. The aqueous phase was cooled, the precipitate was filtered and dried in vacuo to give 1.6 g (38% yield) of the title compound: mp 226° C. (dec); EIMS (70 eV) m/z (relative intensity) 296 (44, M$^+$).

Example 128

(R)-N-8-(4-Methylpiperazin-1-yl)-1,2,3,4-tetrahydro-2-naphthyl-4-(4-benzylpiperazin-1-yl) benzamide A suspension of 4-(4-benzylpiperazin-1-yl)benzoic acid (57 mg, 0.19 mmol) and 1,1'-carbonyldiimidazole (33 mg, 0.20 mmol) in N,N-dimethylformamide (2 mL) was stirred at 75° C. for 2 h. The solution was cooled and (R)-2-amino-8-(4-methylpiperazin-1-yl)-1,2,3,4-tetrahydronaphthalene (45 mg, 0.18 mmol), dissolved in N,N-dimethylformamide (1 mL), was added. The reaction mixture was stirred at ambient temperature for 40 h. The solvent was evaporated and the residue was dried in vacuo to give 149 mg of a crude product. Purification of the residue by preparative TLC (silica) eluting with chloroform/ethanol saturated with NH$_3$ (15:1) as the eluent gave 63 mg (63% yield) of the title compound as a white solid: mp 209–210° C.; [α]$^{21}_D$ –65° (c 0.5, chloroform); EIMS (70 eV) m/z (relative intensity) 523 (13, M$^+$).

Example 129

(R)-N-[8-(4-Methylpiperazin-1-yl)-1,2,3,4-tetrahydro-2-naphthyl]-4-morpholinocarbonylbenzamide 4-Morpholinocarbonylbenzoic acid (130 mg, 0.54 mmol; described in: *J. Med Chem.* 1994, 37(26), 4538–4554) was dissolved in thionyl chloride (5 mL). When the acid was dissolved, the excess of thionyl chloride was evaporated in vacuo, the residue was treated with toluene and again the solvent was removed in vacuo. The crude acid chloride was dissolved in methylene chloride (5 mL) and added dropwise to an ice-cooled solution of (R)-2-amino-8-(4-methylpiperazine-1-yl)-1,2,3,4-tetrahydronaphthalene (120 mg, 0.49 mmol) and triethylamine (100 µL, 0.73 mmol) in methylene chloride (20 mL). After the addition, the reaction was allowed to stir at ambient temperature for 15 min and was then washed with dilute aqueous sodium hydrogen carbonate. The phases were separated and the organic phase was dried (Na$_2$SO$_4$), filtered and evaporated in vacuo to give a crude product which was purified on a silica gel column using using chloroform/methanol/concentrated ammonium hydroxide (95:4:0.5) as the eluent. Yield: 160 mg (72%) of the title compound as white crystals: mp 124–127° C.; [α]$^{21}_D$ –40° (c 1.0, chloroform); EIMS (70 eV) m/z (relative intensity) 462 (2, M$^+$).

Example 130

(R)-N-[8-(4-Methylpiperazin-1-yl)-1,2,3,4-tetrahydro-2-naphthyl]-4-(N,N-dimethylaminocarbonyl)benzamide 4-(N,N-Dimethylaminocarbonyl)benzoic acid (100 mg, 0.54 mmol; described in: U.S. Pat. No. 3,607,918, 1971) was dissolved in thionyl chloride (5 mL). When the acid was dissolved, the excess of thionyl chloride was evaporated in vacuo, the residue was treated with toluene and again the solvent was removed in vacuo. The crude acid chloride was dissolved in methylene chloride (5 mL) and added dropwise to an ice-cooled solution of (R)-2-amino-8-(4-methylpiperazine-1-yl)-1,2,3,4-tetrahydronaphthalene (120 mg, 0.49 mmol) and triethylamine (100 µL, 0.73 mmol) in methylene chloride (20 mL). After the addition, the reaction was allowed to stir at ambient temperature for 15 min and was then washed with dilute aqueous sodium hydrogen carbonate. The phases were separated and the organic phase was dried (Na$_2$SO$_4$), filtered and evaporated in vacuo to give a crude product which was purified on a silica gel column using using chloroform/methanol/concentrated ammonium hydroxide (95:4:0.5) as the eluent. Yield: 160 mg (79%) of the title compound as white foam: [α]$^{21}_D$ –30° (c 1.0, chloroform); EIMS (70 eV) m/z (relative intensity) 420 (10, M$^+$).

Example 131

4-(4-Piperidon-1-yl)benzoic acid

A solution of 2 M NaOH (10 mL), 4-(8-aza-1,4-dioxaspiro[4,5]dec-8-yl)benzonitrile (820 mg, 3.4 mmol; described in: Taylor E. C.; Skotnicki J. S. *Synthesis* 1981, 8, 606–608), and ethanol (7.5 mL) was heated at reflux for 3 h. The external heating was interrupted and the reaction mixture was stirred overnight at ambient temperature. The ethanolic solvent was removed in vacuo and the remains were acidified to pH 4 with 2 M HCl followed by extraction with ethyl acetate (50 mL). The layers were separated, and the pH was adjusted to 6 with 2 M NaOH followed by another extraction with ethyl acetate (50 mL). The to combined organic layers were concentrated in vacuo, and the solid residue was dissolved in 6 M HCl (10 mL). The reaction mixture was stirred at 75° C. for 2.5 h and at 55° C. overnight. The temperature was raised to 75° C. for 2 h, and the reaction mixture was then allowed to cool. The pH was adjusted to 4 and the solution was extracted with ethyl acetate (50 mL). The layers were separated and pH was adjusted to 5 followed by another extraction with ethyl acetate. The combined organic layers were dried (MgSO$_4$) and the solvent was removed in vacuo. The crude product was recrystallized from ethyl acetate affording 300 mg (41% yield) of the title compound as yellowish crystals: mp >215° C. (sinters); EIMS (70 eV) m/z (relative intensity) 219 (M$^+$, 100)

Example 132

(R)-N-[8-(4-Methylpiperazin-1-yl)-1,2,3,4-tetrahydro-2-naphthyl]-4-(4-piperidon-1-yl) benzamide 4-(Piperidon-1-yl)benzoic acid (230 mg, 1.0 mmol) and N,N-diisopropylethylamine (180 µL, 1.0 mmol) were dissolved in dry N,N-dimethylformamide (10 mL) and cooled to −20° C. Isobutylchloroformate (130 μL, 1.0 mmol) was added and the reaction mixture was stirred for 1 h. A solution of (R)-2-amino-8-(4-methylpiperazin-1-yl)-1,2,3,4-tetrahydronaphthalene in N,N-dimethylformamide (2 mL) was added and the reaction mixture was stirred at −20° C. for 30 min and at room temperature for 1 h. The solvent was evaporated and the residue was partitioned between ethyl acetate (100 mL) and 2 M NH$_3$ (15 mL). The organic phase was washed with brine (15 mL), dried (MgSO$_4$) and the solvent was evaporated to give 390 mg of a crude product. Purification by column chromatography on silica using chloroform/methanol/conc. NH$_3$ (950:50:5) and chloroform/ethanol saturated with NH$_3$(15:1) as eluents afforded 124 mg (27% yield) of the title compound as a white solid: mp >223° C. (sinters); EIMS (70 eV) m/z (relative intensity) 446 (M$^+$, 8); [α]$^{22}$D −78° (c 0.28, chloroform).

Example 133

3',4'-Dihydro-8'-[4-methyl(piperazin-1-yl)]-spiro-[1,3-dioxolane-2,2'(1H)-naphthalene]

8'-Bromo-3',4'-dihydrospiro-[1,3-dioxolane-2,2'(1H)-naphthalene] (6.0 g, 22 mmol; described in Sunkyung L.; Stewart P. F.; David E. N. *Synth. Commun.* 1995, 25(18), 2775–2780) was dissolved in toluene (180 mL) and flushed with argon. N-Methylpiperazine (3.0 mL, 27 mmol), R(+)-bis(diphenylphosphino)-1,1'-binaphthyl (830 mg, 1.3 mmol), tetrakis(dibenzylideneacetone)dipalladium (0) (510 mg, 0.45 mmol) and sodium t-butoxide (3.0 g, 31 mmol) were added and the reaction mixture was stirred at 85° C. for 2.5 h. After cooling to room temperature ethyl acetate (400 mL) and 2 M ammonia (60 mL) were added. The phases were separated and the organic layer was washed with 2 M ammonia (30 mL), brine (40 mL) and dried (MgSO$_4$). Evaporation of the solvent gave 7.5 g of a crude product. Purification by column chromatography on silica using chloroform/methanol/conc. NH$_3$ (180:5:0.5) as eluent afforded 5.5 g (84% yield) of the title compound as a yellowish solid: mp 127–128° C.; EIMS (70 eV) m/z (relative intensity) 288 (43, M$^+$).

Example 134

8-[4-Methyl(piperazin-1-yl)]-2-tetralone

3',4'-Dihydro-8'-[4-methyl(piperazin-1-yl)]-spiro-[1,3-dioxotane-2,2'(1H)-naphthalene] (1.0 g, 3.5 mmol) was dissolved in freshly distilled tetrahydrofuran (50 mL) and the solution was cooled to 0° C. To the solution was added 2 M hydrochloric acid (10 mL) and after 5 min the cooling bath was removed. The reaction mixture was stirred at ambient temperature for 3.5 h. Tetrahydrofuran was removed in vacuo and the residue was mixed with methylene chloride (100 mL) and cooled on ice-bath. To the mixture was added 2 M sodium hydroxide (10 mL) and the phases were separated. The organic layer was washed with brine (15 mL) and dried (MgSO$_4$). The solvent was evaporated giving 810 mg (95% yield) of the title compound as a brownish crystalline solid: mp >85° C. (sinters); EIMS (70 eV) m/z (relative intensity) 244 (51, M$^+$).

Example 135

2-Cyano-3,4-dihydro-8-[4-methyl(piperazin-1-yl)]-naphthalene

8-[4-Methyl(piperazin-1-yl)]-2-tetralone (420 mg, 1.7 mmol) was dissolved in diethyl ether (50 mL) and precipitated by the addition of 3 M HCl in diethyl ether (1 mL, 3 mmol). The solvent was evaporated giving 520 mg of the salt. The precipitate was mixed with water (20 mL) and an aqueous solution of potassium cyanide (450 mg, 7.0 mmol in 15 mL) was added giving a slurry. The reaction mixture was stirred for 2.5 h, 2 M hydrochloric acid (400 μL, 0.8 mmol) was added. After an additional 30 min, the slurry (pH~10) was extracted with ethyl acetate (100 mL). The organic phase was washed with water (15 mL) and brine (15 mL) and dried (MgSO$_4$). Evaporation of the solvent gave 460 mg of the crude cyanohydrin. The crude material was dissolved in pyridine (10 mL) and cooled to 0° C. Phosphorus oxychloride (320 μL, 3.5 mmol) was added and the reaction mixture was stirred at 0° C. for 20 min. The cooling bath was removed and the reaction mixture was stirred at room temperature for 13 h. The solvent was evaporated and the residue was mixed with water (15 mL) and pH was adjusted to 11 with 2 M sodium hydroxide. Extraction with ethyl acetate (120 mL), washing the organic phase with water (15 mL) and brine (15 mL), drying (MgSO$_4$), followed by evaporation of the solvent gave 380 mg of a crude product. Purification by column chromatography on silica using chloroform/methanol/conc. NH$_3$ (180:5:0.5) as eluent gave 330 mg (75% yield) of the title compound as a yellowish solid: mp 104–105° C.; EIMS (70 eV) m/z (relative intensity) 253 (47, M$^+$).

Example 136

2-Cyano-1,2,3,4-tetrahydro-8-[4-methyl(piperazin-1-yl)]naphthalene

2-Cyano-3,4-dihydro-8-[4-methyl(piperazin-1-yl)]-naphthalene (230 mg, 0.90 mmol) was dissolved in dry methanol (15 mL) and cooled to 0° C. Magnesium turnings (440 mg, 18 mmol) were added and the reaction mixture was stirred for 45 min at 0° C. and for 4 h at room temperature. The solvent was evaporated and 2 M hydrochloric acid (20 mL) was added to the residue. The mixture was stirred for 1 h, cooled on ice-bath and alkalized to pH 10 with 2 M ammonia. The solution was extracted with ethyl acetate (60+2×30 mL) and the organic phase was washed with brine (15 mL). Drying (MgSO$_4$) and evaporation of the solvent gave 210 mg of a crude product. Purification by preparative TLC on silica using chloroform/methanol/conc. NH$_3$ (95:5:0.5) afforded 160 mg (71% yield) of the title compound as a white solid: mp 111–112° C.; EIMS (70 eV) m/z (relative intensity) 255 (34, M$^+$).

Example 137

N-(4-Morpholinocarbonylphenyl)-8-[4-(methylpiperazin-1-yl)]-1,2,3,4-tetrahydronaphthalene-2-carboxamide 2-Cyano-1,3,4-trihydro-8-[4-(methylpiperazin-1-yl)] naphthalene (170 mg, 0.67 mmol) was dissolved in methanol (2 mL) and 2 M sodium hydroxide (1.7 mL, 3.4 mmol) was added. The reaction mixture was heated at reflux for 1 h and then concentrated to about half the volume. The mixture was stirred at 100° C. for 8 h followed by cooling on ice. 2 M sodium hydroxide (1.7 mL, 3.4 mmol) was added giving a thick slurry. Water was removed by a streem of nitrogen and the solid was dried at 60° C. in vacuo. The crude product was stirred with N,N-dimethyl formamide (10 mL) at 90° C. for 10 min and insoluble material was filtered off. The solvent was evaporated and the residue was dried at 60° C. in vacuo to give 179 mg (97% yield) of the crude acid: CIMS (CH$_4$) m/z (relative intensity) 275 (100, M$^+$+1).

The acid (119 mg, 0.43 mmol) was mixed with N,N-dimethyl formamide (2 mL), 4-methylmorpholine (95 μL, 0.86 mmol) was added and the mixture was cooled to 0° C. Diphenylphosphinic chloride (91 μL, 0.43 mmol) was added and the reaction mixture was stirred for 5 min on ice-bath and for 7 h at room temperature. 4-(Morpholinocarbonyl) aniline (89 mg, 0.43 mmol; described in Delvin J. P. et al. *J. Chem. Soc. Perkin Trans.* 1. 1975 (9) 830–841) was added and the reaction mixture was stirred at room temperature for 16 h. The solvent was evaporated and the residue was partitioned between ethyl acetate (60 mL) and 2 M ammonia (5 mL). The organic phase was washed with brine (5 mL) and dried ($MgSO_4$). The solvent was evaporated giving 185 mg of a crude product. Purification by preparative TLC on silica using chloroform/methanol/conc. $NH_3$ (180:5:0.5) as eluent afforded 70 mg (35% yield) of the title compound as a white foam: EIMS (70 eV) m/z (relative intensity) 462 (49, $M^+$).

Example 138

(R)-N-[8-(4-Methylpiperazin-1-yl)-1,2,3,4-tetrahydro-2-naphthyl]-4-(4-morpholinomethyl)benzamide 4-(4-Morpholinomethyl)benzoic acid (91 mg, 0.41 mmol; described in Grabenko, A. D; Shevchenko, L. I; Pelkis, P. S. *Fiziol. Akt. Veshchestva* 1976, 8, 78–83) and 1,1'-carbonyldiimidazole (70 mg, 0.43 mmol) were dissolved in dry N,N-dimethylformamide (3 mL) and stirred at 75° C. for 2 h. The reaction mixture was cooled to 50° C. and a solution of (R)-2-amino-8-(4-methylpiperazin-1-yl)-1,2,3,4-tetrahydronaphthalene (96 mg, 0.39 mmol) in dry N,N-dimethylformamide (2 mL) was added. The reaction mixture was stirred at 50° C. for 60 h followed by evaporation of the solvent and drying in vacuo giving 290 mg of a crude product. Purification by column chromatography on silica using chloroform/methanol/conc. $NH_3$ (95:5:0.5) as the eluent followed by recrystallization from ethyl acetate (3 mL) and diethyl ether (2 mL) afforded 40 mg (23% yield) of the title compound as a white solid: mp 173–174° C.; EIMS (70 eV) m/z (relative intensity) 448 (18, $M^+$), $[\alpha]^{21}_D$ −0.8° (c 0.20, chloroform).

Pharmacology

Potassium($K^+$) or Electrical Field Stimulation of [$^3$H]-5-HT Release from Occipital Cortex of Guinea Pigs

[$^3$H]-5-HT is released by electrical field stimulation from slices of occipital cortex of guinea pigs which have been pre-incubated with [$^3$H]-5-HT. This release is similar to that caused by nerve stimulation, i.e.exocytotic release from serotoninergic nerve terminals, depending on the presence of $Ca^{2+}$ in the incubation medium. In the guinea pigs (like in humans) the 5-HT release is regulated at the level of the nerve terminals by autoreceptors, belonging to the 5-$HT_{1D}$ receptor subtype. Thus, agonists of 5-$HT_{1D}$ receptors reduce the amount of [$^3$H]-5-HT released by ($K^+$) or field stimulation whereas the release is increased by antagonists of this receptor type. Testing compounds with this method is accordingly a convenient screening technique for determining the potency and functional effect of new 5-$HT_{1D}$ receptor agonists and antagonists.

Methods and Materials

Buffer composition (mM) $NaHCO_3$ (25), $NaH_2PO_4 \cdot H_2O$ (1.2), NaCl (117), Kcl(6), $MgSO_4$, $7H_2O$(1.2), $CaCl_2$(1.3), EDTA $Na_2$(0.03). The buffer is gassed for at least 30 min before use. The pH of the buffer is about 7.2 of room temperature but it rises to about 7.4 at 37° C.

Preparation of Occipital Cortical Slices

Guinea pigs (200–250 g) were decapitated and the whole brains were removed. The occipital cortices were dissected and cut into slices 0.4×4 mm with a McIlwain chopper machine. The white part of the tissue was removed carefully with a tweezers before slicing. The slices were incubated in 5 ml buffer in the presence of 5 mM pargyline chloride. After incubation with 0.1 mM [$^3$H]-5-HT for another 30 min the slices were transferred to a test tube and washed three times with the same volume of buffer. The slices were transferred to the superfusion chambers with a plastic pipette and were washed for 40 min. with the buffer in the presence of the uptake inhibitor citalopram (2.5 μM) with a flow of 0.5 ml/min.

Electrical Stimulation of 5-HT Release

The superfused buffer was collected in 2 ml fractions. The slices were stimulated by electricity with a train of pulses of frequency 3 Hz, duration 2 ms and current 30 mA for 3 min at the 4th and 13th fractions. The tested drugs were added from the 8th fraction to the end of the experiment.

Results

A first electrical (or $K^+$) stimulation resulted in a standard amount of [$^3$H]5-HT released ($S_1$). Between the first and second stimulation the 5-$HT_{1D}$ antagonist was added to the media which resulted in a dose-dependent increase of the release($S_2$) after the second stimulation. See FIG. 1

The $S_2/S_1$ ratio, which is the percent of released [$^3$H]5-HT after the second stimulation ($S_2$) divided by that after the first stimulation ($S_1$), was used to estimate drug effects on transmitter release.

Compounds of the invention may also have the advantages that they may be less toxic, be longer acting, be more potent, have a broader range of activity, produce fewer side effects, be more easily absorbed or have other useful pharmacological properties.

What is claimed is:

1. A compound having the formula (I)

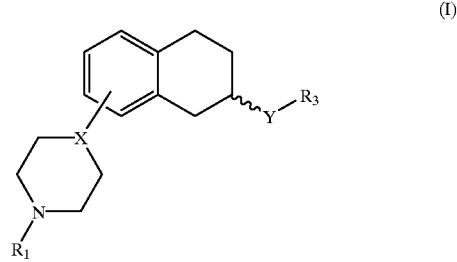

wherein

X is CH;

Y is $NR_2CH_2$, $CH_2$—$NR_2$, $NR_2$—CO, CO—$NR_2$ or $NR_2SO_2$;

$R_1$ is H, $C_1$–$C_6$ alkyl or $C_3$–$C_6$ cycloalkyl;

$R_2$ is H or $C_1$–$C_6$ alkyl;

$R_3$ is $C_1$–$C_6$ alkyl, $C_3$–$C_6$ cycloalkyl or $(CH_2)_n$— aromatic ring, wherein the aromatic ring is phenyl or a heteroaromatic ring containing one or two heteroatoms selected from N, O and S and wherein the aromatic ring may be mono- or di-substituted with $R_4$ and/or $R_5$;

$R_4$ is H, $C_1$–$C_6$ alkyl, $C_3$–$C_6$ cycloalkyl, halogen, CN, $CF_3$, OH, $C_1$–$C_6$ alkoxy, $NR_6R_7$, $OCF_3$, $SO_3CH_3$, $SO_3CF_3$, $SO_2NR_6R_7$, phenyl, phenyl-$C_1$–$C_6$ alkyl, phenoxy, $C_1$–$C_6$ alkyl phenyl, $C_1$–$C_6$ alkyl-heterocyclic ring containing one or two heteroatoms or substituted heteroatoms selected from N, O, S, SO and SO$_2$, an optionally substituted heterocyclic or heteroaromatic ring containing one or two heteroatoms or substituted heteroatoms selected from N, O, S, SO and SO$_2$ wherein the optional substituent(s) may be selected from C$_1$–C$_6$ alkyl, C$_3$–C$_6$ cycloalkyl and phenyl-C$_1$–C$_6$ alkyl; or COR$_8$;

R$_5$ is H, OH, CF$_3$, OCF$_3$, halogen, C$_1$–C$_6$ alkyl or C$_1$–C$_6$ alkoxy;

R$_6$ is H, C$_1$–C$_6$ alkyl or C$_3$–C$_6$ cycloalkyl;

R$_7$ is H, C$_1$–C$_6$ alkyl or C$_3$–C$_6$ cycloalkyl;

R$_8$ is C$_1$–C$_6$ alkyl, C$_3$–C$_6$ cycloalkyl, CF$_3$, NR$_6$R$_7$, phenyl, or a heterocyclic ring containing one or two heteroatoms or substituted heteroatoms selected from N, O, S, SO and SO$_2$;

n is 0–4;

as (R)-enantiomer, (S)-enantiomer or a racemate in the form of the free base or a pharmaceutically acceptable salt or hydrate thereof.

2. A compound according to claim 1 in the form of the (R)-enantiomer.

3. A compound according to claim 1 or 2 wherein the piperidinyl moiety is in the 8 position.

4. A compound according to claim 1 or 2 wherein the piperidinyl moiety is in the 5 position.

5. A compound according to claim 1 or 2 wherein Y is NR$_2$CO and R$_2$ is H or CH$_3$.

6. A compound according to claim 1 or 2 wherein Y is CONR$_2$ and R$_2$ is H or CH$_3$.

7. A compound according to claim 1 or 2 wherein R$_3$ is (CH$_2$)$_n$-phenyl wherein phenyl is para-substituted with R$_4$ and n is 0.

8. A compound according to claim 1 or 2 wherein R$_4$ is C$_1$–C$_6$ alkyl, phenyl, phenyl-C$_1$–C$_6$ alkyl, cyclohexyl, piperidino, morpholino, CF$_3$, 4-piperidon-1-yl, 1-pyrrolyl, C$_1$–C$_6$ alkoxy or COR$_8$ wherein R$_8$ is phenyl, cyclohexyl, piperidino, 1-piperazinyl, morpholino, CF$_3$ or 4-piperidon-1-yl.

9. A compound according to claim 1 wherein Y is NHCO, R$_1$ is H or C$_1$–C$_6$ alkyl, R$_2$ is H, R$_3$ is (CH$_2$)$_n$-phenyl wherein phenyl is para-substituted with R$_4$ and n is 0, where R$_4$ is piperidino, morpholino, thiomorpholino, 4-piperidon-1-yl or n-butoxy.

10. A compound according to claim 3 wherein Y is NR$_2$CO and R$_2$ is H or CH$_3$.

11. A compound according to claim 4 wherein Y is NR$_2$CO and R$_2$ is H or CH$_3$.

12. A compound according to claim 3 wherein Y is CONR$_2$ and R$_2$ is H or CH$_3$.

13. A compound according to claim 4 wherein Y is CONR$_2$ and R$_2$ is H or CH$_3$.

14. A compound according to claim 3 wherein R$_3$ is (CH$_2$)$_n$-phenyl wherein phenyl is para-substituted with R$_4$ and n is 0.

15. A compound according to claim 4 wherein R$_3$ is (CH$_2$)$_n$-phenyl wherein phenyl is para-substituted with R$_4$ and n is 0.

16. A compound according to claim 5 wherein R$_3$ is (CH$_2$)$_n$-phenyl wherein phenyl is para-substituted with R$_4$ and n is 0.

17. A compound according to claim 6 wherein R$_3$ is (CH$_2$)$_n$-phenyl wherein phenyl is para-substituted with R$_4$ and n is 0.

18. A compound according to claim 3 wherein R$_4$ is C$_1$–C$_6$ alkyl, phenyl, phenyl-C$_1$–C$_6$ alkyl, cyclohexyl, piperidino, morpholino, CF$_3$, 4-piperidon-1-yl, 1-pyrrolyl, C$_1$–C$_6$ alkoxy or COR$_8$ wherein R$_8$ is phenyl, cyclohexyl, piperidino, 1-piperazinyl, morpholino, CF$_3$ or 4-piperidon-1-yl.

19. A compound according to claim 4 wherein R$_4$ is C$_1$–C$_6$ alkyl, phenyl, phenyl-C$_1$–C$_6$ alkyl, cyclohexyl, piperidino, morpholino, CF$_3$, 4-piperidon-1-yl, 1-pyrrolyl, C$_1$–C$_6$ alkoxy or COR$_8$ wherein R$_8$ is phenyl, cyclohexyl, piperidino, 1-piperazinyl, morpholino, CF$_3$ or 4-piperidon-1-yl.

20. A compound according to claim 5 wherein R$_4$ is C$_1$–C$_6$ alkyl, phenyl, phenyl-C$_1$–C$_6$ alkyl, cyclohexyl, piperidino, morpholino, CF$_3$, 4-piperidon-1-yl, 1-pyrrolyl, C$_1$–C$_6$ alkoxy or COR$_8$ wherein R$_8$ is phenyl, cyclohexyl, piperidino, 1-piperazinyl, morpholino, CF$_3$ or 4-piperidon-1-yl.

21. A compound according to claim 6 wherein R$_4$ is C$_1$–C$_6$ alkyl, phenyl, phenyl-C$_1$–C$_6$ alkyl, cyclohexyl, piperidino, morpholino, CF$_3$, 4-piperidon-1-yl, 1-pyrrolyl, C$_1$–C$_6$ alkoxy or COR$_8$ wherein R$_8$ is phenyl, cyclohexyl, piperidino, 1-piperazinyl, morpholino, CF$_3$ or 4-piperidon-1-yl.

22. A compound according to claim 7 wherein R$_4$ is C$_1$–C$_6$ alkyl, phenyl, phenyl-C$_1$–C$_6$ alkyl, cyclohexyl, piperidino, morpholino, CF$_3$, 4-piperidon-1-yl, 1-pyrrolyl, C$_1$–C$_6$ alkoxy or COR$_8$ wherein R$_8$ is phenyl, cyclohexyl, piperidino, 1-piperazinyl, morpholino, CF$_3$ or 4-piperidon-1-yl.

23. A compound which is (R)-N-[8-(1-Methylpiperidin-4-yl)-1,2,3,4-tetrahydro-2-naphthyl]-4-morpholinobenzamide;

(R)-N-[8-(1-Methylpiperidin-4-yl)-1,2,3,4-tetrahydro-2-naphthyl]-4-trifluoromethylbenzamide or (R)-N-[8-(1-Methylpiperidin-4-yl)-1,2,3,4-tetrahydro-2-naphthyl]-4-butoxybenzamide;

in the form of a free base or a pharmaceutically acceptable salt or hydrate thereof.

24. A pharmaceutical formulation comprising as active ingredient a therapeutically effective amount of the compound of claim 1 or 2 as an enantiomer or racemate in the form of a free base or a pharmaceutically acceptable salt or hydrate thereof optionally in association with diluents, excipients or inert carriers.

25. A process for the preparation of the compound of formula (I) according to claim 1 which comprises A(i). acylation, in the case when R$_1$ is C$_1$–C$_6$ alkyl or C$_3$–C$_6$ cycloalkyl, Y is NR$_2$CO, R$_2$ is hydrogen, X is N or CH and R$_3$ is as defined in general formula (I) in claim 1, of a compound of formula (XII) or (XXVIII)

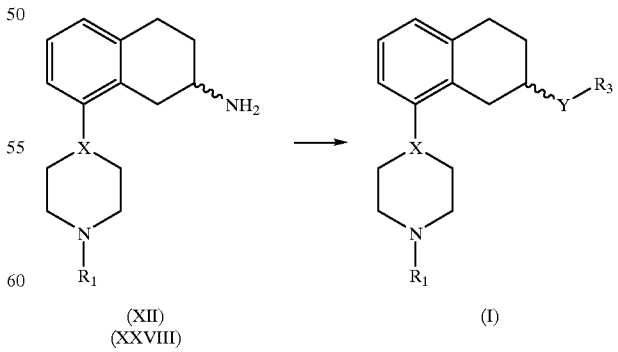

with an activated carboxylic acid R$_3$—COL where L is a leaving group; or by using a carboxylic acid R$_3$—COOH with an activating agent;

A(ii). acylation, in the case when $R_1$ is hydrogen, Y is $NR_2CO$, $R_2$ is hydrogen, X is N or CH and $R_3$ is as defined in general formula (I) in claim 1, of a compound of formula (XIVa) where $R_d$ is a protecting group

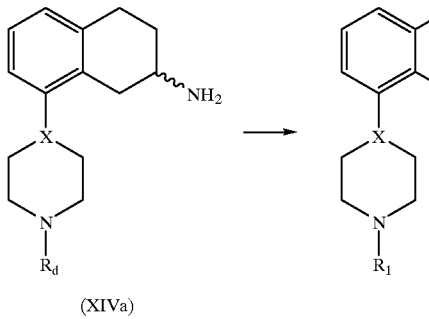

(XIVa)      (I)

with an activated carboxylic acid $R_3$—COL where L is a leaving group, or by using a carboxylic acid $R_3$—COOH with an activating agent followed by the removal of the protecting group $R_d$;

A(iii) acylation, in the case when $R_1$ is $C_1$–$C_6$ alkyl or $C_3$–$C_6$ cycloalkyl, Y is $NR_2CO$, $R_2$ is $C_1$–$C_6$ alkyl, X is N or CH and $R_3$ is as defined in general formula (I) in claim 1, of a compound of formula (XLIIIa)

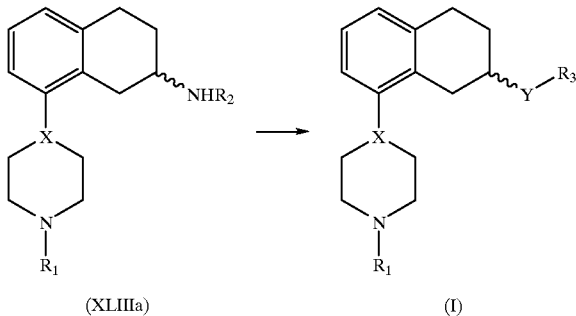

(XLIIIa)      (I)

with an activated carboxylic acid $R_3$—COL where L is a leaving group, or by using a carboxylic acid $R_3$—COOH with an activating agent;

B(i). reacting, in the case when $R_1$ is $C_1$–$C_6$ alkyl or $C_3$–$C_6$ cycloalkyl, Y is $CONR_2$, $R_2$ is hydrogen or $C_1$–$C_6$ alkyl, and X and $R_3$ are as defined in formula (I) in claim 1, an activated carboxylic acid of a compound of formula (XXXVa)

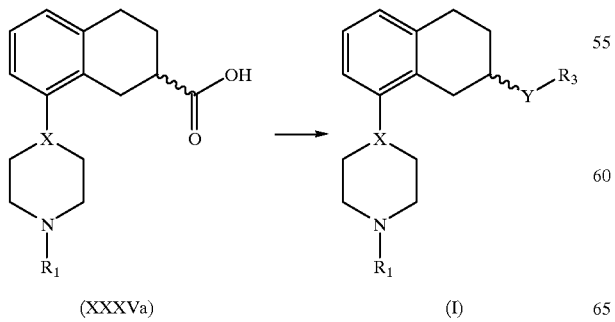

(XXXVa)      (I)

with an aniline or amine $HNR_2R_3$;

B(ii). reacting, in the case when $R_1$ is hydrogen, Y is $CONR_2$, $R_2$ is hydrogen or $C_1$–$C_6$ alkyl, $R_d$ is a protecting group and $R_3$ and X are as defined in formula (I) in claim 1, an activated carboxylic acid of a compound of formula (XLIIa)

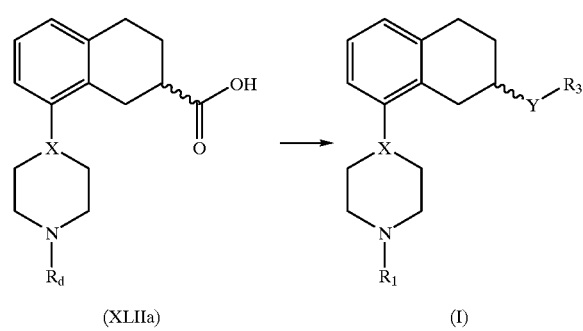

(XLIIa)      (I)

with an aniline or amine $HNR_2R_3$, followed by removal of the protecting group $R_d$;

C. reacting, in the case when $R_1$ is $C_1$–$C_6$ alkyl or $C_3$–$C_6$ cycloalkyl, Y is $NR_2SO_2$, $R_2$ is hydrogen, and X and $R_3$ are as defined in formula (I) in claim 1, a compound of formula (XIIa)

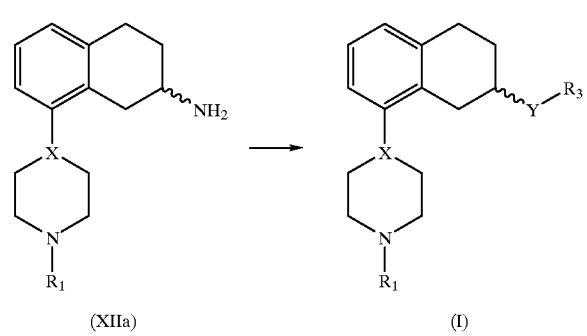

(XIIa)      (I)

with an activated sulfonic acid $R_3$—$SO_2L$ where L is a leaving group;

D. reducing a compound of formula (I) obtained from
  (i) method A(i), A(ii) or A(iii) to a compound of formula (I), where $R_1$ is hydrogen, $C_1$–$C_6$ alkyl or $C_3$–$C_6$ cycloalkyl, Y is $NR_2CH_2$, $R_2$ is hydrogen or $C_1$–$C_6$ alkyl, and X and $R_3$ are as defined in formula (I) in claim 1;
  (ii) method B(i) or B(ii) to a compound of formula (I), where R1 is hydrogen, $C_1$–$C_6$ alkyl or $C_3$–$C_6$ cycloalkyl, Y is $CH_2NR_2$, $R_2$ is hydrogen or $C_1$–$C_6$ alkyl, and X and $R_3$ are as defined in formula (I) in claim 1;

E. alkylation, in the case when $R_1$ is $C_1$–$C_6$ alkyl or $C_3$–$C_6$ cycloalkyl, Y is $NR_2CH_2$, $R_2$ is hydrogen or $C_1$–$C_6$ alkyl, and X and $R_3$ are as defined in formula (I) in claim 1, of a compound of formula (XIIa), (XIVa) or (XLIIIa)

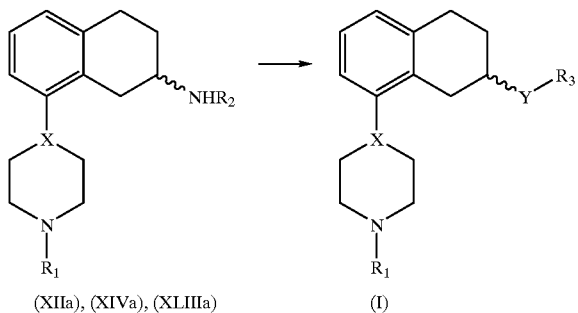

(XIIa), (XIVa), (XLIIIa)     (I)

with a compound $R_3CH_2$—L where L is a leaving group selected from the group consisting of a halogen, an alkylsulfonyloxy group and an arylsulfonyloxy group, optionally followed by removal of protecting groups;

F. alkylation, in the case when $R_1$ is $C_1$–$C_6$ alkyl, Y is $NR_2CO$, $R_2$ is hydrogen or $C_1$–$C_6$ alkyl, and X and $R_3$ are as defined in formula (I) in claim 1, of a compound of formula (Ie)

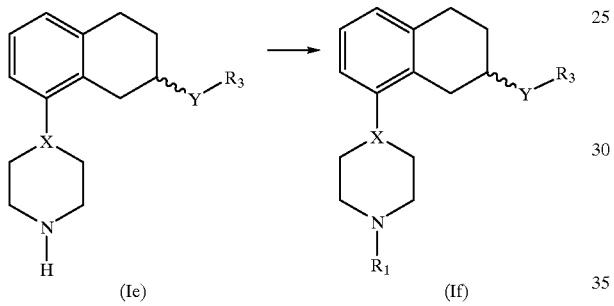

(Ie)     (If)

with a compound $R_1$—L where L is a leaving group selected from the group consisting of a halogen, an alkylsulfonyloxy group and an arylsulfonyloxy group.

26. A method for the treatment of 5-hydroxytryptamine-mediated disorders in the central nervous system, which comprises administering to a patient in need of such treatment a therapeutically effective amount of a compound defined in claim 1 or 2.

27. A method for the treatment of 5-hydroxytryptamine-mediated disorders in the central nervous system which require treatment with a 5-$HT_{1D}$ antagonist, which comprises administering to a patient in need of such treatment a therapeutically effective amount of a compound defined in claim 1 or 2.

28. A method according to claim 26 for the treatment of mood disorders, anxiety disorders, personality disorders, obesity, anorexia, bulimia, premenstrual syndrome, sexual disturbances, alcoholism, tobacco abuse, autism, attention deficit, hyperactivity disorder, migraine, memory disorders, pathological aggression, schizophrenia, endocrine disorders, stroke, dyskinesia, Parkinson's disease, thermoregulatory disorders, pain or hypertension.

29. A method according to claim 26 for the treatment of 5-hydroxytryptamine-mediated urinary incontinence or vasospasm or for inhibition of tumor growth.

30. A compound having the formula

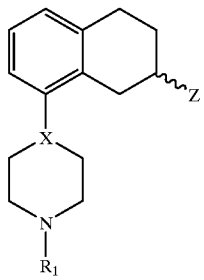

wherein

Z is $NH_2$ or COOH;

X is CH or N; and $R_1$ is H, $C_1$–$C_6$ akyl or $C_3$–$C_6$ cycloalkyl.

* * * * *